(12) United States Patent
Aponte et al.

(10) Patent No.: US 10,041,087 B2
(45) Date of Patent: *Aug. 7, 2018

(54) PLANTS HAVING INCREASED TOLERANCE TO HERBICIDES

(71) Applicant: BASF AGRO B.V., EA Arnheim (NL)

(72) Inventors: Raphael Aponte, Mannheim (DE); Stefan Tresch, Kirchheim (DE); Matthias Witschel, Bad Duerkheim (DE); Jens Lerchl, Golm (DE); Jill Marie Paulik, Cary, NC (US); Chad Brommer, Raleigh, NC (US)

(73) Assignee: BASF AGRO B.V., Arnheim (NL)

( * ) Notice: Subject to any disclaimer, the term of this patent is extended or adjusted under 35 U.S.C. 154(b) by 454 days.

This patent is subject to a terminal disclaimer.

(21) Appl. No.: 13/918,212

(22) Filed: Jun. 14, 2013

(65) Prior Publication Data

US 2014/0123340 A1    May 1, 2014

Related U.S. Application Data

(60) Provisional application No. 61/661,364, filed on Jun. 19, 2012.

(51) Int. Cl.
*C12N 15/82* (2006.01)
*C12N 15/52* (2006.01)
*C12N 9/00* (2006.01)
*A01H 5/10* (2018.01)
*A01H 5/00* (2018.01)
*G01N 33/50* (2006.01)
*C12N 9/02* (2006.01)
*A01N 43/84* (2006.01)

(52) U.S. Cl.
CPC ......... *C12N 15/8274* (2013.01); *A01N 43/84* (2013.01); *C12N 9/0059* (2013.01); *G01N 33/5097* (2013.01); *G01N 2333/90206* (2013.01)

(58) Field of Classification Search
None
See application file for complete search history.

(56) References Cited

U.S. PATENT DOCUMENTS

| | | |
|---|---|---|
| 5,169,770 A | 12/1992 | Chee et al. |
| 5,198,013 A | 3/1993 | Hirai et al. |
| 5,322,783 A | 6/1994 | Tomes et al. |
| 5,366,892 A | 11/1994 | Foncerrada et al. |
| 5,376,543 A | 12/1994 | Chee et al. |
| 5,380,831 A | 1/1995 | Adang et al. |
| 5,436,391 A | 7/1995 | Fujimoto et al. |
| 5,485,192 A | 1/1996 | Nagahata et al. |
| 5,593,881 A | 1/1997 | Thompson et al. |
| 5,723,756 A | 3/1998 | Peferoen et al. |
| 5,747,450 A | 5/1998 | Ohba et al. |
| 5,767,373 A | 6/1998 | Ward et al. |
| 5,773,702 A | 6/1998 | Penner et al. |
| 5,859,348 A | 1/1999 | Penner et al. |
| 5,939,360 A | 8/1999 | Adachi et al. |
| 5,939,602 A | 8/1999 | Volrath et al. |
| 5,948,917 A | 9/1999 | Adachi et al. |
| 5,990,387 A | 11/1999 | Tomes et al. |
| 6,018,105 A | 1/2000 | Johnson et al. |
| 6,027,945 A | 2/2000 | Smith et al. |
| 6,084,155 A | 7/2000 | Volrath et al. |
| 6,160,206 A | 12/2000 | Sato et al. |
| 6,368,800 B1 | 4/2002 | Smith et al. |
| 6,653,529 B2 | 11/2003 | Peng et al. |
| 6,905,852 B1 | 6/2005 | Horikoshi et al. |
| 7,250,561 B1 * | 7/2007 | Pallett .................. C12N 9/0069 435/320.1 |
| 7,671,254 B2 * | 3/2010 | Tranel .................... C12N 9/001 435/320.1 |
| 7,705,200 B2 | 4/2010 | Dam et al. |
| 7,745,699 B2 | 6/2010 | Nakajima et al. |
| 7,842,856 B2 | 11/2010 | Tranel et al. |
| 8,097,774 B2 | 1/2012 | Hawkes et al. |
| 8,129,589 B2 | 3/2012 | Tanaka et al. |
| 8,338,337 B2 | 12/2012 | Song et al. |
| 2003/0236208 A1 | 12/2003 | Kmiec et al. |

(Continued)

FOREIGN PATENT DOCUMENTS

| | | |
|---|---|---|
| CA | 2382090 | 2/2001 |
| CA | 2807035 A1 | 2/2012 |

(Continued)

OTHER PUBLICATIONS

Patzoldt et al, PNAS (2006) 103:12329-12334.*
Dayan et al, Biochim. Biophys. Acta (2010) 1548-1556.*
GenBank Accession No. DQ386114, Submitted on Jan. 31, 2006.*
Lyga et al, Pesticide Sci. (1999) 55:281-287.*
Macias et al, J. Acric. Food Chem. (2006) 54:9357-9365.*
Arnould and Comadro, "The Domain Structure of Protoporphyrinogen Oxidase, the Molecular Target of Diphenyl Ether-Type Herbicides," Proc. Natl. Acad. Sci. USA, vol. 95, (1998), pp. 10553-10558.

(Continued)

*Primary Examiner* — Mykola V Kovalenko
(74) *Attorney, Agent, or Firm* — Marshall, Gerstein & Borun LLP

(57) ABSTRACT

The present invention refers to a method for controlling undesired vegetation at a plant cultivation site, the method comprising the steps of providing, at said site, a plant that comprises at least one nucleic acid comprising a nucleotide sequence encoding a wild-type or a mutated protoporphyrinogen oxidase (PPO) which is resistant or tolerant to a benzoxazinone-derivative herbicide by applying to said site an effective amount of said herbicide. The invention further refers to plants comprising wild-type or mutated PPO enzymes, and methods of obtaining such plants.

48 Claims, 4 Drawing Sheets

(56) References Cited

U.S. PATENT DOCUMENTS

| | | | |
|---|---|---|---|
| 2004/0082770 A1* | 4/2004 | Castle | C12N 9/1029 536/23.2 |
| 2005/0084859 A1 | 4/2005 | Nakajima et al. | |
| 2007/0021515 A1 | 1/2007 | Glenn et al. | |
| 2007/0050863 A1 | 3/2007 | Tranel et al. | |
| 2009/0049567 A1 | 2/2009 | Olhoft et al. | |
| 2010/0100988 A1 | 4/2010 | Tranel et al. | |
| 2011/0201501 A1 | 8/2011 | Song et al. | |
| 2012/0122223 A1 | 5/2012 | Gocal et al. | |
| 2013/0184155 A1 | 7/2013 | Newton et al. | |
| 2014/0123340 A1 | 5/2014 | Aponte et al. | |
| 2014/0189906 A1 | 7/2014 | Gocal et al. | |

FOREIGN PATENT DOCUMENTS

| | | |
|---|---|---|
| CN | 1036571 | 10/1989 |
| CN | 1150820 A | 5/1997 |
| CN | 1212724 A | 3/1999 |
| CN | 1175107 C | 11/2004 |
| CN | 1894408 A | 1/2007 |
| CN | 101215289 A | 7/2008 |
| CN | 101437844 A | 5/2009 |
| CN | 101998988 A | 3/2011 |
| DE | 19505995 | 8/1996 |
| EP | 0397687 | 6/1989 |
| EP | 0424047 | 4/1991 |
| EP | 0900795 | 4/2004 |
| WO | WO 1993007256 | 4/1993 |
| WO | WO 1996026202 | 8/1996 |
| WO | WO-1997/004088 A1 | 2/1997 |
| WO | WO 1997032011 | 9/1997 |
| WO | WO 1997041116 | 11/1997 |
| WO | WO 1997041117 | 11/1997 |
| WO | WO 1997041118 | 11/1997 |
| WO | WO-1998/029554 A1 | 7/1998 |
| WO | WO-1998/033927 A1 | 8/1998 |
| WO | WO 2001012815 | 2/2001 |
| WO | WO-2001/068826 A2 | 9/2001 |
| WO | WO 2001083459 | 11/2001 |
| WO | WO 2002068607 | 9/2002 |
| WO | WO 2005107437 | 11/2005 |
| WO | WO 2006024820 | 3/2006 |
| WO | WO 2006037945 | 4/2006 |
| WO | WO 2007024739 | 3/2007 |
| WO | WO 2007071900 | 6/2007 |
| WO | WO 2007096576 | 8/2007 |
| WO | WO 2008124495 | 10/2008 |
| WO | WO 2008141154 | 11/2008 |
| WO | WO 2010049269 | 5/2010 |
| WO | WO 2010049270 | 5/2010 |
| WO | WO 2010145992 | 12/2010 |
| WO | WO 2011018486 | 2/2011 |
| WO | WO 2012018862 | 2/2012 |
| WO | WO 2012041789 | 4/2012 |
| WO | WO 2012080975 | 6/2012 |
| WO | WO-2013/189984 A2 | 12/2013 |
| WO | WO-2015/022636 A2 | 2/2015 |
| WO | WO-2015/022639 A2 | 2/2015 |
| WO | WO-2015/092706 A1 | 6/2015 |

OTHER PUBLICATIONS

Che et al., "Localization of Target-Site of the Protoporphyrinogen Oxidase-Inhibiting Herbicide, S-23142, in *Spinacia oleracea* L.," Z. Naturforsch., vol. 48c, (1993), pp. 350-355.

Che et al., "Molecular Characterization and Subcellular Localization of Protoporphyrinogen Oxidase in Spinach Chloroplasts," Plant Physiology, vol. 124, (2000), pp. 59-70.

Choi et al., "Generation of Resistance to the Diphenyl Ether Herbicide, Oxyfluorfen, via Expression of the *Bacillus subtilis* Protoporphyrinogen Oxidase Gene in Transgenic Tobacco Plants," Biosci. Biotechnol. Biochem., vol. 62, No. 3, (1998), pp. 558-560.

Cole-Strauss et al., "Targeted Gene Repair Directed by the Chimeric RNA/DNA Oligonucleotide in a Mammalian Cell-Free Extract," Nucleic Acids Research, vol. 27, No. 5, (1999), pp. 1323-1330.

Corradi et al., "Crystal Structure of Protoporphyrinogen Oxidase from *Myxococcus xanthus* and it Complex with the Inhibitor Acifluorfen," J Biol Chem., vol. 281, No. 50, (2006), pp. 38625-38633.

Dailey et al., "Expression of a Cloned Protoporphyrinogen Oxidase," The Journal of Biological Chemistry, vol. 269, No. 2, (1994), pp. 813-815.

Dayan and Duke, "Phytotoxicity of Protoporphyrinogen Oxidase Inhibitors: Phenomenology, Mode of Action and Mechanisms of Resistance," Herbicide Activity: Toxicology, Biochemistry and Molecular Biology, eds. Roe et al., (1997), pp. 11-35.

Dayan et al., "Biochemical and Structural Consequences of a Glycine Deletion in the α-8 Helix of Protoporphyrinogen Oxidase," Biochimica et Biophysica Acta, vol. 1804, (2010), pp. 1548-1556.

Duke et al., "Protoporphyrinogen Oxidase-Inhibiting Herbicides," Weed Science, vol. 39, (1991), pp. 465-473.

Geiser et al., "The Hypervariable Region in the Genes Coding for Entomopathogenic Crystal Proteins of *Bacillus thuringiensis*: Nucleotide Sequence of the kurhd1 Gene of subsp. *kurstaki* HD1," Gene, vol. 48, (1986), pp. 109-118.

Ha et al., The Plastidic *Arabidopsis* Protoporphyrinogen IX Oxidase Gene, with or without the Transit Sequence, Confers Resistance to the Diphenyl Ether Herbicide in Rice, Plant, Cell and Environment, vol. 27, (2003), pp. 79-88.

Hao et al., "Protoporphyrinogen Oxidase Inhibitor: An Ideal Target for Herbicide Discovery," Chimia, vol. 65, No. 12, (2011), pp. 961-969.

Heinemann et al., "Functional Definition of the Tobacco Protoporphyrinogen IX Oxidase Substrate-Binding Site," Biochem. J., vol. 402, (2007), pp. 575-580.

Holmberg, "A Fine Line: New Herbicide-Tolerant Crops Blur the Fine Line between Weed Control and Crop Injury," Successful Farming, vol. 98, No. 5, (2000), pp. 25-27.

Huang et al., "Synthesis and Herbicidal Activity of Isoindoline-1,3-dione Substituted Benzoxazinone Derivatives Containing a Carboxylic Ester Group," J. Agric. Food Chem., vol. 57, (2009), pp. 9585-9592.

International Search Report, issued in co-assigned PCT/IB2011/055701, dated May 3, 2012.

Jacobs and Jacobs, "Assay for Enzymatic Protoporphyrinogen Oxidation, a Late Step in Heme Synthesis," Enzyme, vol. 28, (1982), pp. 206-219.

Jung and Kuk, "Resistance Mechanisms in Protoporphyrinogen Oxidase (PROTOX) Inhibitor-Resistant Transgenic Rice," Journal of Plant Biology, vol. 50, No. 3, (2007), pp. 586-594.

Jung et al., "Dual Targeting of *Myxococcus xanthus* Protoporphyrinogen Oxidase into Chloroplasts and Mitochondria and High Level Oxyfluorfen Resistance," Plant, Cell and Environment, vol. 27, (2004), pp. 1436-1446.

Kataoka et al., "Isolation and Partial Characterization of Mutant *Chlamydomonas reinhardtii* Resistant to Herbicide S-23142," J. Pesticide Sci., vol. 15, (1990), pp. 449-451.

Koch et al., "Crystal Structure of Protoporphyrinogen IX Oxidase: A Key Enzyme in Haem and Chlorophyll Biosynthesis," The EMBO Journal, vol. 23, (2004), pp. 1720-1728.

Layer et al., "Structure and Function of Enzymes in Heme Biosynthesis," Protein Science, vol. 19, (2010), pp. 1137-1161.

Lee et al., "Cellular Localization of Protoporphyrinogen—Oxidizing Activity of Etiolated Barley (*Hordeum volgare* L.) Leaves," Plant Physiol., vol. 102, (1993), pp. 881-889.

Lee et al., "Expression of Human Protoporphyrinogen Oxidase in Transgenic Rice Induces Both a Photodynamic Response and Oxyfluorfen Resistance," Pesticide Biochemistry and Physiology, vol. 80, (2004), pp. 65-74.

Lee et al., "Transgenic Rice Plants Expressing a *Bacillus subtilis* Protoporphyrinogen Oxidase Gene are Resistant to Diphenyl Ether Herbicide Oxyfluorfen," Plant Cell Physiol., vol. 41, No. 6, (2000), pp. 743-749.

Lermontova and Grimm, "Overexpression of Plastidic Protoporphyrinogen IX Oxidase Leads to Resistance to the Diphenyl-Ether Herbicide Acifluorfen," Plant Physiology, vol. 122, (2000), pp. 75-83.

(56) References Cited

OTHER PUBLICATIONS

Lermontova et al., "Cloning and Characterization of a Plastidal and a Mitochondrial Isoform of Tobacco Protoporphyrinogen IX Oxidase," Proc. Natl. Acad. Sci. USA, vol. 94, (1997), pp. 8895-8900.

Li and Nicholl, "Development of PPO Inhibitor-Resistant Cultures and Crops," Pest Manag Sci, vol. 61, (2005), pp. 277-285.

Li et al., "Development of Protoporphyrinogen Oxidase as an Efficient Selection Marker for *Agrobacterium tumefaciens*—Mediated Transformation of Maize," Plant Physiology, vol. 133, (2003), pp. 736-747.

Loppes, "A New Class of Arginine-Requiring Mutants in *Chlamydomonas reinhardi*," Molec. Gen. Genetics, vol. 104, (1969), pp. 172-177.

Matringe et al., "Protoporphyrinogen Oxidase as a Molecular Target for Diphenyl Ether Berbicides," Biochem. J., vol. 260, (1989), pp. 231-235.

Matringe et al., "Protoporphyrinogen Oxidase Inhibition by Three Peroxidizing Herbicides: Oxadiazon, LS 82-556 and M&B 39279," FEBS Lett., vol. 245, Nos. 1, 2, (1989), pp. 35-38.

Mulwa and Mwanza, "Biotechnology Approaches to Developing Herbicide Tolerance/Selectivity in Crops," African Journal of Biotechnology, vol. 5, No. 5, (2006), pp. 396-404.

Murray et al., "Codon Usage in Plant Genes," Nucleic Acids Research, vol. 17, No. 2, (1989), pp. 477-498.

Nandihalli et al., "Quantitative Structure-Activity Relationships of Protoporphyrinogen Oxidase-Inhibiting Diphenyl Ether Herbicides," Pesticide Biochemistry and Physiology, vol. 43, (1992), pp. 193-211.

Oshio et al., "Isolation and Characterization of a *Chlamydomonas reinhardtii* Mutant Resistant to Photobleaching Herbicides," Z. Naturforsch., vol. 48c, (1993), pp. 339-344.

Patzoldt et al., "A Codon Deletion Confers Resistance to Herbicides Inhibiting Protoporphyrinogen Oxidase," PNAS, vol. 103, No. 33, (2006), pp. 12329-12334.

Säsärman et al., "Mapping of a New hem Gene in *Escherichia coli* K12," Journal of General Microbiology, vol. 113, (1979), pp. 297-303.

Säsärman et al., "Nucleotide Sequence of the hemG Gene Involved in the Protoporphyrinogen Oxidase Activity of *Escherichia coli* K12," Can. J. Microbiol., vol. 39, (1993), pp. 1155-1159.

Shibata et al., "Isolation and Characterization of a *Chlamydomonas reinhardtii* Mutant Resistant to an Experimental Herbicide S-23142, which Inhibits Chlorophyll Synthesis," Research in Photosynthesis, vol. III, (1992), pp. 567-570.

Watanabe et al., "Molecular Characterization of Photomixotrophic Tobacco Cells Resistant to Protoporphyrinogen Oxidase-lnhibiting Herbicides," Plant Physiol., vol. 118, (1998), pp. 751-758.

Yanase and Andoh, "Porphyrin Synthesis Involvement in Diphenyl Ether-like Mode of Action of TNPP-Ethyl, a Novel Phenylpyrazole Herbicide," Pesticide Biochemistry and Physiology, vol. 35, (1989), pp. 70-80.

Hao et al., "Protoporphyrinogen Oxidase Inhibitor: An Ideal Target for Herbicide Discovery", *CHIMIA*, 65(12): 961-969 (2011).

International Search Report for International Application No. PCT/EP2013/062744, dated Dec. 10, 2014.

Extended European Search Report, issued in co-assigned application No. 11848519.2, dated Apr. 23, 2014.

GenBank Accession No. ACF78832, unknown [*Zea mays*], Jul. 30, 2008.

GenBank Accession No. AX084732, submitted on Mar. 9, 2001.

GenBank Accession No. XM_004975973, Predicted: Setaria italica protoporphyrinogen oxidase, mitochondrial (LOC101781148), mRNA, Nov. 30, 2015.

GenBank Accession No. XP_004976030.1, Predicted: Protoporhyrinogen oxidase, mitochondrial [Setaria italica], Nov. 30, 2015.

Hanin et al., Gene targeting in *Arabidopsis*. Plant J. 28: 671-7 (2001).

International Search Report and Written Opinion, International Application No. PCT/IB2014/063873, dated Feb. 9, 2015.

International Preliminary Report on Patentability, International Application No. PCT/IB2014/063873, dated Feb. 16, 2016.

International Search Report and Written Opinion, International Application No. PCT/IB2014/063876, dated Jan. 28, 2015.

International Preliminary Report on Patentability, International Application No. PCT/IB2014/063876, dated Feb. 16, 2016.

International Search Report and Written Opinion, International Application No. PCT/IB2014/063877, dated Feb. 10, 2015.

International Preliminary Report on Patentability, International Application No. PCT/IB2014/063877, dated Feb. 16, 2016.

Lewis et al., Interactions between redox partners in various cytochrome P450 systems: Functional and structural aspects. *Biochim. Biophys. Acta*, 1460(2-3): 353-74 (2000).

Randolph-Anderson et al., Isolation and characterization of a mutant protoporphyrinogen oxidase gene from Chlamydomonas reinhardtii conferring resistance to porphyric herbicides. *Plant Mol. Biol.* 38(5): 839-59 (1998).

Rousonelos, S., Master's Thesis, University of Illinois, published Aug. 2010.

Su et al., The development of protoporphyrinogen oxidase inhibiting herbicides, *Agrochem. Res. Appl.* 15(1): 1-5 (2011)—English abstract only.

\* cited by examiner

SEQUENCE LISTING

<160> NUMBER OF SEQ ID NOS: 48

<210> SEQ ID NO 1
<211> LENGTH: 1605
<212> TYPE: DNA
<213> ORGANISM: Amaranthus tuberculatus

<400> SEQUENCE: 1

-continued

| | |
|---|---|
| atggtaattc aatccattac ccacctttca ccaaaccttg cattgccatc gccattgtca | 60 |
| gtttcaacca agaactaccc agtagctgta atgggcaaca tttctgagcg ggaagaaccc | 120 |
| acttctgcta aaagggttgc tgttgttggt gctggagtta gtggacttgc tgctgcatat | 180 |
| aagctaaaat cccatggttt gagtgtgaca ttgtttgaag ctgattctag agctggaggc | 240 |
| aaacttaaaa ctgttaaaaa agatggtttt atttgggatg agggggcaaa tactatgaca | 300 |
| gaaagtgagg cagaggtctc gagtttgatc gatgatcttg gcttcgtga agcaacag | 360 |
| ttgccaattt cacaaaataa agatacata gctagagacg tcttcctgt gctactacct | 420 |
| tcaaatcccg ctgcactact cacgagcaat atcctttcag caaaatcaaa gctgcaaatt | 480 |
| atgttggaac catttctctg gagaaaacac aatgctactg aactttctga tgagcatgtt | 540 |
| caggaaagcg ttggtgaatt ttttgagcga cattttggga agagtttgt tgattatgtt | 600 |
| atcgacccctt ttgttgcggg tacatgtggt ggagatcctc aatcgctttc catgcaccat | 660 |
| acatttccag aagtatggaa tattgaaaaa aggtttggct ctgtgtttgc tggactaatt | 720 |
| caatcaacat tgttatctaa gaaggaaaag ggtggagaaa atgcttctat taagaagcct | 780 |
| cgtgtacgtg gttcattttc atttcaaggt ggaatgcaga cacttgttga cacaatgtgc | 840 |
| aaacagcttg gtgaagatga actcaaactc agtgtgagg tgctgtcctt gtcatataac | 900 |
| cagaagggga tccctcatt agggaattgg tcagtctctt ctatgtcaaa taataccagt | 960 |
| gaagatcaat cttatgatgc tgtggttgtc actgctccaa ttcgcaatgt caagaaatg | 1020 |
| aagattatga aatttggaaa tccattttca cttgacttta ttccagaggt gacgtacgta | 1080 |
| cccctttccg ttatgattac tgcattcaaa aaggataaag tgaagagacc tcttgagggc | 1140 |
| ttcggagttc ttatcccctc taaagagcaa cataatggac tgaagactct tggtacttta | 1200 |
| ttttcctcca tgatgtttcc tgatcgtgct ccatctgaca tgtgtctctt tactacattt | 1260 |
| gtcggaggaa gcagaaatag aaaacttgca aacgcttcaa cggatgaatt gaagcaaata | 1320 |
| gtttcttctg accttcagca gctgttgggc actgaggacg aaccttcatt tgtcaatcat | 1380 |
| ctcttttgga gcaacgcatt cccattgtat ggacacaatt acgattctgt tttgagagcc | 1440 |
| atagacaaga tggaaaagga tcttcctgga ttttttatg caggtaacca taagggtgga | 1500 |
| ctttcagtgg gaaaagcgat ggcctccgga tgcaaggctg cggaacttgt aatatcctat | 1560 |
| ctggactctc atatatacgt gaagatggat gagaagaccg cgtaa | 1605 |

<210> SEQ ID NO 2
<211> LENGTH: 534
<212> TYPE: PRT
<213> ORGANISM: Amaranthus tuberculatum

<400> SEQUENCE: 2

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
            130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
            195                 200                 205

Cys Gly Gly Asp Pro Gln Ser Leu Ser Met His His Thr Phe Pro Glu
210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
            275                 280                 285

Lys Leu Gln Cys Glu Val Leu Ser Leu Ser Tyr Asn Gln Lys Gly Ile
            290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
            355                 360                 365

Phe Lys Lys Asp Lys Val Lys Arg Pro Leu Glu Gly Phe Gly Val Leu
            370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
            435                 440                 445

Leu Gly Thr Glu Asp Glu Pro Ser Phe Val Asn His Leu Phe Trp Ser
            450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 3
<211> LENGTH: 1605
<212> TYPE: DNA
<213> ORGANISM: Amaranthus tuberculatus

<400> SEQUENCE: 3

| | | | | | |
|---|---|---|---|---|---|
| atggtaattc | aatccattac | ccacctttca | ccaaaccttg | cattgccatc | gccattgtca | 60 |
| gtttcaacca | agaactaccc | agtagctgta | atgggcaaca | tttctgagcg | ggaagaaccc | 120 |
| acttctgcta | aaagggttgc | tgttgttggt | gctggagtta | gtggacttgc | tgctgcatat | 180 |
| aagctaaaat | cccatggttt | gagtgtgaca | ttgtttgaag | ctgattctag | agctggaggc | 240 |
| aaacttaaaa | ctgttaaaaa | agatggtttt | atttgggatg | aggggcaaa | tactatgaca | 300 |
| gaaagtgagg | cagaggtctc | gagtttgatc | gatgatcttg | gcttcgtga | aagcaacag | 360 |
| ttgccaattt | cacaaaataa | aagatacata | gctagagccg | tcttcctgt | gctactacct | 420 |
| tcaaatcccg | ctgcactact | cacgagcaat | atcctttcag | caaaatcaaa | gctgcaaatt | 480 |
| atgttggaac | catttctctg | gagaaaacac | aatgctactg | aactttctga | tgagcatgtt | 540 |
| caggaaagcg | ttggtgaatt | ttttgagcga | catttgga | aagagtttgt | tgattatgtt | 600 |
| attgacccctt | tgttgcggg | tacatgtggt | ggagatcctc | aatcgctttc | catgcaccat | 660 |
| acatttccag | aagtatggaa | tattgaaaaa | aggtttggct | ctgtgtttgc | cggactaatt | 720 |
| caatcaacat | tgttatctaa | gaaggaaaag | ggtggagaaa | atgcttctat | taagaagcct | 780 |
| cgtgtacgtg | ttcatttc | atttcaaggt | ggaatgcaga | cacttgttga | cacaatgtgc | 840 |
| aaacagcttg | gtgaagatga | actcaaactc | cagtgtgagg | tgctgtcctt | gtcatataac | 900 |
| cagaagggga | tcccctcact | agggaattgg | tcagtctctt | ctatgtcaaa | taataccagt | 960 |
| gaagatcaat | cttatgatgc | tgtggttgtc | actgctccaa | ttcgcaatgt | caaagaaatg | 1020 |
| aagattatga | aatttggaaa | tccatttca | cttgacttta | ttccagaggt | gacgtacgta | 1080 |
| cccctttccg | ttatgattac | tgcattcaaa | aaggataaag | tgaagagacc | tcttgagggc | 1140 |
| ttcggagttc | ttatccctc | taaagagcaa | cataatggac | tgaagactct | tggtacttta | 1200 |
| tttttcctcca | tgatgtttcc | tgatcgtgct | ccatctgaca | tgtgtctctt | tactacattt | 1260 |
| gtcgaggaa | gcagaaatag | aaaacttgca | aacgcttcaa | cggatgaatt | gaagcaaata | 1320 |
| gtttcttctg | accttcagca | gctgttgggc | actgaggacg | aaccttcatt | tgtcaatcat | 1380 |
| ctctttttgga | gcaacgcatt | cccattgtat | ggacacaatt | acgattctgt | tttgagagcc | 1440 |
| atagacaaga | tggaaaagga | tcttcctgga | tttttttatg | caggtaacca | taagggtgga | 1500 |
| ctttcagtgg | gaaaagcgat | ggcctccgga | tgcaaggctg | cggaacttgt | aatatcctat | 1560 |
| ctggactctc | atatatacgt | gaagatggat | gagaagaccg | cgtaa | | 1605 |

<210> SEQ ID NO 4
<211> LENGTH: 534
<212> TYPE: PRT
<213> ORGANISM: Amaranthus tuberculatum

<400> SEQUENCE: 4

Met Val Ile Gln Ser Ile Thr His Leu Ser Pro Asn Leu Ala Leu Pro
1               5                   10                  15

```
Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
                100                 105                 110

Leu Gly Leu Arg Glu Lys Gln Gln Leu Pro Ile Ser Gln Asn Lys Arg
            115                 120                 125

Tyr Ile Ala Arg Ala Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
210                 215                 220

Val Trp Asn Ile Glu Lys Arg Phe Gly Ser Val Phe Ala Gly Leu Ile
225                 230                 235                 240

Gln Ser Thr Leu Leu Ser Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
```

```
                435                 440                 445
Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 5
<211> LENGTH: 1602
<212> TYPE: DNA
<213> ORGANISM: Amaranthus tuberculatus

<400> SEQUENCE: 5
atggtaattc aatccattac ccacctttca ccaaaccttg cattgccatc gccattgtca     60
gtttccacca gaactaccc agtagctgta atgggcaaca tttctgagcg agaagaaccc    120
acttctgcta aaaggttgc tgttgttggt gctggagtta gtggacttgc tgctgcatat    180
aagctaaaat cccatggttt gagtgtgaca ttgtttgaag ctgattctag agctggaggc    240
aaacttaaaa ctgttaaaaa agatggtttt atttgggatg agggggcaaa tactatgaca    300
gaaagtgagg cagaggtctc gagtttgatc gatgatcttg gcttcgtga aagcaacag     360 ttgccaattt cacaaaataa agatacata gctagagacg tcttcctgt gctactacct    420 tcaaatcccg ctgcactact cacgagcaat atcctttcag caaaatcaaa gctgcaaatt    480
atgttggaac catttctctg gagaaaacac aatgctactg aactttctga tgagcatgtt    540
caggaaagcg ttggtgaatt ttttgagcga cattttggga aagagtttgt tgattatgtt    600
attgaccctt tgttgcggg tacatgtgga gatcctcaat cgctttccat gcaccataca    660
tttccagaag tatggaatat tgaaaaaagg tttggctctg tgtttgctgg actaattcaa    720
tcaacattgt tatctaagaa ggaaaagggt ggagaaaatg cttctattaa gaagcctcgt    780
gtacgtggtt cattttcatt tcaaggtgga atgcagacac ttgttgacac aatgtgcaaa    840
cagcttggtg aagatgaact caaactccag tgtgaggtgc tgtccttgtc atataaccag    900 aagggggatcc cctcattagg gaattggtca gtctcttcta tgtcaaataa taccagtgaa    960
gatcaatctt atgatgctgt ggttgtcact gctccaattc gcaatgtcaa agaaatgaag   1020
attatgaaat ttggaaatcc attttcactt gactttattc cagaggtgac gtacgtaccc   1080
ctttccgtta tgattactgc attcaaaaag gataaagtga agagacctct tgagggcttc   1140
ggagttctta tccctctaa agagcaacat aatggactga agactcttgg tactttattt   1200
tcctccatga tgtttcctga tcgtgctcca tctgacatgt gtctctttac tacatttgtc   1260
ggaggaagca gaaatagaaa acttgcaaac gcttcaacgg atgaattgaa gcaaatagtt   1320
tcttctgacc ttcagcagct gttgggcact gaggacgaac cttcatttgt caatcatctc   1380
ttttggagca acgcattccc attgtatgga cacaattacg attgtgtttt gagagccata   1440
gacaagatgg aaaaggatct tcctggattt ttttatgcag gtaaccataa gggtggactt   1500
tcagtgggaa aagcgatggc ctccggatgc aaggctgcgg aacttgtaat atcctatctg   1560
```
gactctcata tatacgtgaa gatggatgag aagaccgcgt aa    1602

<210> SEQ ID NO 6
<211> LENGTH: 533
<212> TYPE: PRT
<213> ORGANISM: Amaranthus tuberculatum

<400> SEQUENCE: 6

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
                420                 425                 430

Thr Asp Glu Leu Lys Gln Ile Val Ser Ser Asp Leu Gln Gln Leu Leu
            435                 440                 445

Gly Thr Glu Asp Glu Pro Ser Phe Val Asn His Leu Phe Trp Ser Asn
        450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
                500                 505                 510

Ala Glu Leu Val Ile Ser Tyr Leu Asp Ser His Ile Tyr Val Lys Met
            515                 520                 525

Asp Glu Lys Thr Ala
    530

<210> SEQ ID NO 7
<211> LENGTH: 1602
<212> TYPE: DNA
<213> ORGANISM: Amaranthus tuberculatus

<400> SEQUENCE: 7
atggtaattc aatccattac ccacctttca ccaaaccttg cattgccatc gccattgtca      60
gtttccacca agaactaccc agtagctgta atgggcaaca tttctgagcg ggaagaaccc     120
acttctgcta aagggttgc tgttgttggt gctggagtta gtggacttgc tgctgcatat     180
aagctaaaat cccatggttt gagtgtgaca ttgtttgaag ctaattctag agctggaggc     240
aaacttaaaa ctgttaaaaa gatggttttt atttgggatg aggggggcaaa tactatgaca     300
gaaagtgagg cagaggtctc gagtttgatc gatgatcttg gcttcgtga agcaacag      360
ttgccaattt cacaaaataa agatacata gctagagacg tcttcctgt gctactacct     420
tcaaatcccg ctgcactact cacgagcaat atcctttcag caaaatcaaa gctgcaaatt     480
atgttggaac catttctctg gagaaaacac aatgctactg aactttctga tgagcatgtt     540
caggaaagcg ttggtgaatt ttttgagcga cattttggga aagagtttgt tgattatgtt     600
attgacccgt tgttgcggg tacatgtgga gatcctcaat cgctttccat gtaccataca     660
tttccagaag tatggaatat tgaaaaaaag tttggctctg tgtttgctgg actaattcaa     720
tcaacattgt tatctaagaa ggaaaagggt ggagaaaatg cttctattaa gaagcctcgt     780
gtacgtggtt catttcattt tcaaggtgga atgcagacac ttgttgacac aatgtgcaaa     840
cagcttggtg aagatgaact caaactccag tgtgaggtgc tgtccttgtc atataaccag     900
aaggggatcc cctcattagg gaattggtca gtctcttcta tgtcaaataa taccagtgaa     960
gatcaatctt atgatgctgt ggttgtcact gctccaattc gcaatgtcaa agaaatgaag    1020
attatgaaat ttggaaatcc attttcactt gactttattc cagaggtgac gtacgtaccc    1080
cttttccgtta tgattactgc attcaaaaag gataaagtga agagacctct tgagggcttc    1140

```
ggagttctta tcccctctaa agagcaacat aatggactga agactcttgg tactttattt    1200
tcctccatga tgtttcctga tcgtgctcca tctgacatgt gtctctttac tacatttgtc    1260
ggaggaagca gaaatagaaa acttgcaaac gcttcaacgg atgaattgaa gcaaatagtt    1320
tcttctgacc ttcagcagct gttgggcact gaggacgaac cttcatttgt caatcatctc    1380
ttttggagca acgcattccc attgtatgga cacaattacg attctgtttt gagagccata    1440
gacaagatgg aaaaggatct tcctggatttt ttatgcag gtaaccataa gggtggactt    1500
tcagtgggaa aagcgatggc ctccggatgc aaggctgcgg aacttgtaat atcctatctg    1560
gactctcata tatacgtgaa gatggatgag aagaccgcgt aa                      1602
```

<210> SEQ ID NO 8
<211> LENGTH: 533
<212> TYPE: PRT
<213> ORGANISM: Amaranthus tuberculatum

<400> SEQUENCE: 8

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met Tyr His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285
```

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Thr Ala Pro Ile Arg Asn Val
                325                 330                 335

Lys Glu Met Lys Ile Met Lys Phe Gly Asn Pro Phe Ser Leu Asp Phe
                340                 345                 350

Ile Pro Glu Val Thr Tyr Val Pro Leu Ser Val Met Ile Thr Ala Phe
            355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
                420                 425                 430

Thr Asp Glu Leu Lys Gln Ile Val Ser Ser Asp Leu Gln Gln Leu Leu
            435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
    515                 520                 525

Asp Glu Lys Thr Ala
    530

<210> SEQ ID NO 9
<211> LENGTH: 1644
<212> TYPE: DNA
<213> ORGANISM: Arabidopsis thaliana

<400> SEQUENCE: 9
atgggcctga ttaaaaacgg tacccttat tgtcgttttg ggataagctg gaattttgcc      60
gctgtgtttt tttctactta tttccgtcac tgctttcgac tggtcagaga ttttgactct     120
gaattgttgc agatagcaat ggcgtctgga gcagtagcag atcatcaaat tgaagcggtt     180
tcaggaaaaa gagtcgcagt cgtaggtgca ggtgtaagtg acttgcggc ggcttacaag      240 ttgaaatcga ggggtttgaa tgtgactgtg tttgaagctg atggaagagt aggtgggaag     300
ttgagaagtg ttatgcaaaa tggtttgatt tgggatgaag agcaaacac catgactgag      360 gctgagccag aagttgggag tttacttgat gatcttgggc ttcgtgagaa caacaatttt     420
ccaatttcac agaaaaagcg gtatattgtg cggaatggtg tacctgtgat gctacctacc     480
aatcccatag agctggtcac aagtagtgtg ctctctaccc aatctaagtt tcaaatcttg     540
ttggaaccat ttttatggaa gaaaaagtcc tcaaaagtct cagatgcatc tgctgaagaa     600
agtgtaagcg agttctttca cgccattttt ggacaagagg ttgttgacta tctcatcgac     660
ccttttgttg gtggaacaag tgctgcggac cctgattccc tttcaatgaa gcattctttc     720

```
ccagatctct ggaatagttt tggctctatt atagtcggtg caatcagaac aaagtttgct    780
gctaaaggtg gtaaaagtag agacacaaag agttctcctg cacaaaaaa gggttcgcgt    840 gggtcattct cttttaaggg gggaatgcag attcttcctg atacgttgtg caaaagtctc    900
tcacatgatg agatcaattt agactccaag gtactctctt tgtcttacaa ttctggatca    960
agacaggaga actggtcatt atcttgtgtt tcgcataatg aaacgcagag acaaaacccc   1020
cattatgatg ctgctcctct gtgcaatgtg aaggagatga aggttatgaa aggaggacaa   1080 cccctttcagc taaactttct ccccgagatt aattacatgc ccctctcggt tttaatcacc   1140
acattcacaa aggagaaagt aaagagacct cttgaaggct ttggggtact cattccatct   1200
aaggagcaaa agcatggttt caaaactcta ggtacacttt tttcatcaat gatgtttcca   1260
gatcgttccc ctagtgacgt tcatctatat acaactttta ttggtgggag taggaaccag   1320
gaactagcca aagcttccac tgacgaatta aaacaagttg tgacttctga ccttcagcga   1380
ctgttggggg ttgaaggtga acccgtgtct gtcaaccatt actattggag gaaagcattc   1440
ccgttgtatg acagcagcta tgactcagtc atggaagcaa ttgacaagat ggagaatgat   1500
ctacctgggt tcttctatgc aggtaatcat cgagggggc tctctgttgg gaaatcaata   1560
gcatcaggtt gcaaagcagc tgaccttgtg atctcatacc tggagtcttg ctcaaatgac   1620
aagaaaccaa atgacagctt ataa                                         1644
```

```
<210> SEQ ID NO 10
<211> LENGTH: 547
<212> TYPE: PRT
<213> ORGANISM: Arabidopsis thaliana

<400> SEQUENCE: 10

Met Gly Leu Ile Lys Asn Gly Thr Leu Tyr Cys Arg Phe Gly Ile Ser
1               5                   10                  15

Trp Asn Phe Ala Ala Val Phe Ser Thr Tyr Phe Arg His Cys Phe
            20                  25                  30

Arg Leu Val Arg Asp Phe Asp Ser Glu Leu Leu Gln Ile Ala Met Ala
        35                  40                  45

Ser Gly Ala Val Ala Asp His Gln Ile Glu Ala Val Ser Gly Lys Arg
    50                  55                  60

Val Ala Val Val Gly Ala Gly Val Ser Gly Leu Ala Ala Ala Tyr Lys
65                  70                  75                  80

Leu Lys Ser Arg Gly Leu Asn Val Thr Val Phe Glu Ala Asp Gly Arg
                85                  90                  95

Val Gly Gly Lys Leu Arg Ser Val Met Gln Asn Gly Leu Ile Trp Asp
            100                 105                 110

Glu Gly Ala Asn Thr Met Thr Glu Ala Glu Pro Glu Val Gly Ser Leu
        115                 120                 125

Leu Asp Asp Leu Gly Leu Arg Glu Lys Gln Gln Phe Pro Ile Ser Gln
    130                 135                 140

Lys Lys Arg Tyr Ile Val Arg Asn Gly Val Pro Val Met Leu Pro Thr
145                 150                 155                 160

Asn Pro Ile Glu Leu Val Thr Ser Ser Val Leu Ser Thr Gln Ser Lys
                165                 170                 175

Phe Gln Ile Leu Leu Glu Pro Phe Leu Trp Lys Lys Ser Ser Lys
            180                 185                 190

Val Ser Asp Ala Ser Ala Glu Glu Ser Val Ser Glu Phe Phe Gln Arg
        195                 200                 205
```

His Phe Gly Gln Glu Val Val Asp Tyr Leu Ile Asp Pro Phe Val Gly
                210                 215                 220
Gly Thr Ser Ala Ala Asp Pro Asp Ser Leu Ser Met Lys His Ser Phe
225                 230                 235                 240
Pro Asp Leu Trp Asn Ser Phe Gly Ser Ile Ile Val Gly Ala Ile Arg
                245                 250                 255
Thr Lys Phe Ala Ala Lys Gly Gly Lys Ser Arg Asp Thr Lys Ser Ser
                260                 265                 270
Pro Gly Thr Lys Lys Gly Ser Arg Gly Ser Phe Ser Phe Lys Gly Gly
                275                 280                 285
Met Gln Ile Leu Pro Asp Thr Leu Cys Lys Ser Leu Ser His Asp Glu
                290                 295                 300
Ile Asn Leu Asp Ser Lys Val Leu Ser Leu Ser Tyr Asn Ser Gly Ser
305                 310                 315                 320
Arg Gln Glu Asn Trp Ser Leu Ser Cys Val Ser His Asn Glu Thr Gln
                325                 330                 335
Arg Gln Asn Pro His Tyr Asp Ala Ala Pro Leu Cys Asn Val Lys Glu
                340                 345                 350
Met Lys Val Met Lys Gly Gly Gln Pro Phe Gln Leu Asn Phe Leu Pro
                355                 360                 365
Glu Ile Asn Tyr Met Pro Leu Ser Val Leu Ile Thr Thr Phe Thr Lys
                370                 375                 380
Glu Lys Val Lys Arg Pro Leu Glu Gly Phe Gly Val Leu Ile Pro Ser
385                 390                 395                 400
Lys Glu Gln Lys His Gly Phe Lys Thr Leu Gly Thr Leu Phe Ser Ser
                405                 410                 415
Met Met Phe Pro Asp Arg Ser Pro Ser Asp Val His Leu Tyr Thr Thr
                420                 425                 430
Phe Ile Gly Gly Ser Arg Asn Gln Glu Leu Ala Lys Ala Ser Thr Asp
                435                 440                 445
Glu Leu Lys Gln Val Val Thr Ser Asp Leu Gln Arg Leu Leu Gly Val
450                 455                 460
Glu Gly Glu Pro Val Ser Val Asn His Tyr Tyr Trp Arg Lys Ala Phe
465                 470                 475                 480
Pro Leu Tyr Asp Ser Ser Tyr Asp Ser Val Met Glu Ala Ile Asp Lys
                485                 490                 495
Met Glu Asn Asp Leu Pro Gly Phe Phe Tyr Ala Gly Asn His Arg Gly
                500                 505                 510
Gly Leu Ser Val Gly Lys Ser Ile Ala Ser Gly Cys Lys Ala Ala Asp
                515                 520                 525
Leu Val Ile Ser Tyr Leu Glu Ser Cys Ser Asn Asp Lys Lys Pro Asn
530                 535                 540
Asp Ser Leu
545

<210> SEQ ID NO 11
<211> LENGTH: 1647
<212> TYPE: DNA
<213> ORGANISM: Nicotiana tabacum

<400> SEQUENCE: 11
atgacaacaa ctcccatcgc caatcatcct aatattttca ctcaccagtc gtcgtcatcg      60
ccattggcat tcttaaaccg tacgagtttc atcccttcct cttcaatctc caagcgcaat     120

```
agtgtcaatt gcaatggctg agaacacga tgctccgttg ccaaagatta cacagttcct      180
tcctcagcgg tcgacggcgg acccgccgcg gagctggact gtgttatagt tggagcagga      240
attagtggcc tctgcattgc gcaggtgatg tccgctaatt accccaattt gatggtaacc      300
gaggcgagag atcgtgccgg tggcaacata cgactgtgg aaagagacgg ctatttgtgg       360
gaagaaggtc ccaacagttt ccagccgtcc gatcctatgt tgactatggc agtagattgt      420
ggattgaagg atgatttggt gttgggagat cctaatgcgc cccgtttcgt tttgtggaag      480
ggtaaattaa ggcccgtccc ctcaaaactc actgatcttc ccttttttga tttgatgagc      540
attcctggca agttgagagc tggttttggt gccattggcc tccgcccttc acctccaggt      600
catgaggaat cagttgagca gttcgtgcgt cgtaatcttg gtggcgaagt ctttgaacgc      660
ttgatagaac cattttgttc tggtgtttat gctggtgatc cctcaaaact gagtatgaaa      720
gcagcatttg ggaaagtttg aagttggaa gaaactggtg gtagcattat ggaggaacc       780
tttaaagcaa taaggagag atccagtaca cctaaagcgc cccgcgatcc gcgtttacct      840
aaaccaaaag gacagacagt tggatcattc aggaagggtc tcagaatgct gccggatgca      900
atcagtgcaa gattgggaag caaattaaaa ctatcatgga agctttctag cattactaag      960
tcagaaaaag gaggatatca cttgacatac gagacaccag aaggagtagt ttctcttcaa     1020
agtcgaagca ttgtcatgac tgtgccatcc tatgtagcaa gcaacatatt acgtcctctt     1080
tcggttgccg cagcagatgc actttcaaat ttctactatc ccccagttgg agcagtcaca     1140
atttcatatc ctcaagaagc tattcgtgat gagcgtctgg ttgatggtga actaaaggga     1200
tttgggcagt tgcatccacg tacacaggga gtggaaacac taggaacgat atatagttca     1260
tcactcttcc ctaaccgtgc cccaaaaggt cgggtgctac tcttgaacta cattggagga     1320
gcaaaaaatc ctgaaatttt gtctaagacg gagagccaac ttgtggaagt agttgatcgt     1380
gacctcagaa aaatgcttat aaaacccaaa gctcaagatc tcttgttgt gggtgtgcga      1440
gtatggccac aagctatccc acagtttttg gttggtcatc tggatacgct aagtactgca     1500
aaagctgcta tgaatgataa tgggcttgaa gggctgtttc ttgggggtaa ttatgtgtca     1560
ggtgtagcat tggggaggtg tgttgaaggt gcttatgaag ttgcatccga ggtaacagga     1620
tttctgtctc ggtatgcata caaatga                                        1647
```

<210> SEQ ID NO 12
<211> LENGTH: 548
<212> TYPE: PRT
<213> ORGANISM: Nicotiana tabacum

<400> SEQUENCE: 12

```
Met Thr Thr Thr Pro Ile Ala Asn His Pro Asn Ile Phe Thr His Gln
1               5                   10                  15

Ser Ser Ser Ser Pro Leu Ala Phe Leu Asn Arg Thr Ser Phe Ile Pro
            20                  25                  30

Phe Ser Ser Ile Ser Lys Arg Asn Ser Val Asn Cys Asn Gly Trp Arg
        35                  40                  45

Thr Arg Cys Ser Val Ala Lys Asp Tyr Thr Val Pro Ser Ser Ala Val
    50                  55                  60

Asp Gly Gly Pro Ala Ala Glu Leu Asp Cys Val Ile Val Gly Ala Gly
65                  70                  75                  80

Ile Ser Gly Leu Cys Ile Ala Gln Val Met Ser Ala Asn Tyr Pro Asn
                85                  90                  95

Leu Met Val Thr Glu Ala Arg Asp Arg Ala Gly Gly Asn Ile Thr Thr
```

```
            100                 105                 110
Val Glu Arg Asp Gly Tyr Leu Trp Glu Glu Gly Pro Asn Ser Phe Gln
        115                 120                 125

Pro Ser Asp Pro Met Leu Thr Met Ala Val Asp Cys Gly Leu Lys Asp
        130                 135                 140

Asp Leu Val Leu Gly Asp Pro Asn Ala Pro Arg Phe Val Leu Trp Lys
145                 150                 155                 160

Gly Lys Leu Arg Pro Val Pro Ser Lys Leu Thr Asp Leu Pro Phe Phe
                165                 170                 175

Asp Leu Met Ser Ile Pro Gly Lys Leu Arg Ala Gly Phe Gly Ala Ile
            180                 185                 190

Gly Leu Arg Pro Ser Pro Gly His Glu Glu Ser Val Glu Gln Phe
        195                 200                 205

Val Arg Arg Asn Leu Gly Gly Glu Val Phe Glu Arg Leu Ile Glu Pro
        210                 215                 220

Phe Cys Ser Gly Val Tyr Ala Gly Asp Pro Ser Lys Leu Ser Met Lys
225                 230                 235                 240

Ala Ala Phe Gly Lys Val Trp Lys Leu Glu Glu Thr Gly Gly Ser Ile
                245                 250                 255

Ile Gly Gly Thr Phe Lys Ala Ile Lys Glu Arg Ser Ser Thr Pro Lys
            260                 265                 270

Ala Pro Arg Asp Pro Arg Leu Pro Lys Pro Lys Gly Gln Thr Val Gly
        275                 280                 285

Ser Phe Arg Lys Gly Leu Arg Met Leu Pro Asp Ala Ile Ser Ala Arg
        290                 295                 300

Leu Gly Ser Lys Leu Lys Leu Ser Trp Lys Leu Ser Ser Ile Thr Lys
305                 310                 315                 320

Ser Glu Lys Gly Gly Tyr His Leu Thr Tyr Glu Thr Pro Glu Gly Val
                325                 330                 335

Val Ser Leu Gln Ser Arg Ser Ile Val Met Thr Val Pro Ser Tyr Val
            340                 345                 350

Ala Ser Asn Ile Leu Arg Pro Leu Ser Val Ala Ala Asp Ala Leu
        355                 360                 365

Ser Asn Phe Tyr Tyr Pro Pro Val Gly Ala Val Thr Ile Ser Tyr Pro
        370                 375                 380

Gln Glu Ala Ile Arg Asp Glu Arg Leu Val Asp Gly Glu Leu Lys Gly
385                 390                 395                 400

Phe Gly Gln Leu His Pro Arg Thr Gln Gly Val Glu Thr Leu Gly Thr
                405                 410                 415

Ile Tyr Ser Ser Ser Leu Phe Pro Asn Arg Ala Pro Lys Gly Arg Val
            420                 425                 430

Leu Leu Leu Asn Tyr Ile Gly Gly Ala Lys Asn Pro Glu Ile Leu Ser
        435                 440                 445

Lys Thr Glu Ser Gln Leu Val Glu Val Asp Arg Asp Leu Arg Lys
        450                 455                 460

Met Leu Ile Lys Pro Lys Ala Gln Asp Pro Leu Val Val Gly Val Arg
465                 470                 475                 480

Val Trp Pro Gln Ala Ile Pro Gln Phe Leu Val Gly His Leu Asp Thr
                485                 490                 495

Leu Ser Thr Ala Lys Ala Ala Met Asn Asp Asn Gly Leu Glu Gly Leu
            500                 505                 510

Phe Leu Gly Gly Asn Tyr Val Ser Gly Val Ala Leu Gly Arg Cys Val
        515                 520                 525
```

Glu Gly Ala Tyr Glu Val Ala Ser Glu Val Thr Gly Phe Leu Ser Arg
    530                 535                 540

Tyr Ala Tyr Lys
545

<210> SEQ ID NO 13
<211> LENGTH: 1668
<212> TYPE: DNA
<213> ORGANISM: Cichorium intybus

<400> SEQUENCE: 13

| | | | | | |
|---|---|---|---|---|---|
| atgacatctc | tcacagacgt | ttgttccctc | aactgttgcc | gtagctggtc | ttcccttccg | 60 |
| ccaccggttt | ctggtgggtc | gttgacgtca | agaatccta | ggtacctaat | cacgtatagt | 120 |
| ccggcgcatc | gcaaatgcaa | taggtggagg | ttccgctgct | ctatagccaa | ggattcccca | 180 |
| attactcctc | ccatttcaaa | tgagttcaac | tctcagccat | tgttggactg | tgtcattgtg | 240 |
| ggcgccggca | ttagcggcct | ttgcattgcg | caggccctag | cgactaaaca | cgcctccgtc | 300 |
| tctccggatg | tgatcgtcac | cgaggcacga | gacagagtcg | ggggtaatat | atcaacggtt | 360 |
| gaaagggatg | gctatctctg | gaagaaggt | cctaacagct | tccagccatc | tgatgccatg | 420 |
| ctcaccatgg | tggtggatag | tgggttgaag | gatgatttgg | tgttaggtga | cccaacagca | 480 |
| ccccgctttg | tattatgggg | aggtgatttg | aaaccggttc | cttccaaacc | ggctgacctc | 540 |
| cctttctttg | acctcatgag | ctttcctgga | aaactcagag | ccggttttgg | tgctcttgga | 600 |
| ttccgtcctt | cacctccaga | tcgcgaagaa | tcggttgagg | agtttgttag | acgtaatctt | 660 |
| ggagatgaag | ttttcgaacg | cttgatagaa | ccttttttgct | caggtgttta | tgctggtgat | 720 |
| ccatcaaaac | ttagtatgaa | agcagcattt | gggaaggtct | ggaatctgga | gcaaaatggt | 780 |
| ggtagcattg | ttggtggagc | cttcaaggct | attcaggaca | gaaagaatag | tcaaaagcct | 840 |
| ccacgggacc | cgaggttacc | gaaaccaaag | ggccaaactg | ttggatcttt | taggaaagga | 900 |
| caagcgatgt | tgcctaatgc | aatctcaacg | aggttaggta | gcagagtgaa | attgtgttgg | 960 |
| aagctcacga | gtatttcaaa | attggagaat | agaggttata | atttgacata | tgaaacacca | 1020 |
| caaggatttg | aaagtctgca | gactaaaact | atcgtgatga | ctgttccatc | ctacgtggcg | 1080 |
| agtgacttgt | tgcgtccgct | ttcgttgggt | gcagcagatg | cattgtcaaa | attttattat | 1140 |
| cctccggttg | cagctgtatc | aatttcatat | ccaaaagacg | caattcgtgc | tgaccggctg | 1200 |
| attgatggtc | aactcaaagg | ttttgggcaa | ttgcatccac | gaagtcaagg | ggtggaaact | 1260 |
| ttaggtacga | tctacagttc | atctcttttc | cctaaccgag | cgccacctgg | aagggttctg | 1320 |
| ctcttgaact | acatcggagg | ggctacaaat | cctgaaattc | tatcaaagac | ggagggcgaa | 1380 |
| attgtggatg | cggtggaccg | ggacctacgg | acgatgctga | taaggcgtga | tgcggaagat | 1440 |
| ccattgacgt | tgggggtgcg | ggtgtggcct | cgagcaatcc | cgcagtttct | gatcggtcat | 1500 |
| tatgacattc | tagattctgc | aaaagctgct | ctgagtagcg | tggattcca | aggtatgttt | 1560 |
| cttggtggca | actatgtgtc | tggtgtggct | ttaggtaaat | gtgtcgaggc | tgcttatgat | 1620 |
| gttgccgctg | aggtaatgaa | cttttttgtcg | caaggggtgt | acaagtga | | 1668 |

<210> SEQ ID NO 14
<211> LENGTH: 555
<212> TYPE: PRT
<213> ORGANISM: Cichorium

<400> SEQUENCE: 14

-continued

```
Met Thr Ser Leu Thr Asp Val Cys Ser Leu Asn Cys Cys Arg Ser Trp
 1               5                  10                  15

Ser Ser Leu Pro Pro Val Ser Gly Gly Ser Leu Thr Ser Lys Asn
            20                  25                  30

Pro Arg Tyr Leu Ile Thr Tyr Ser Pro Ala His Arg Lys Cys Asn Arg
            35                  40                  45

Trp Arg Phe Arg Cys Ser Ile Ala Lys Asp Ser Pro Ile Thr Pro Pro
 50                  55                  60

Ile Ser Asn Glu Phe Asn Ser Gln Pro Leu Leu Asp Cys Val Ile Val
 65                  70                  75                  80

Gly Ala Gly Ile Ser Gly Leu Cys Ile Ala Gln Ala Leu Ala Thr Lys
                 85                  90                  95

His Ala Ser Val Ser Pro Asp Val Ile Val Thr Glu Ala Arg Asp Arg
            100                 105                 110

Val Gly Gly Asn Ile Ser Thr Val Glu Arg Asp Gly Tyr Leu Trp Glu
            115                 120                 125

Glu Gly Pro Asn Ser Phe Gln Pro Ser Asp Ala Met Leu Thr Met Val
            130                 135                 140

Val Asp Ser Gly Leu Lys Asp Asp Leu Val Leu Gly Asp Pro Thr Ala
145                 150                 155                 160

Pro Arg Phe Val Leu Trp Gly Gly Asp Leu Lys Pro Val Pro Ser Lys
                165                 170                 175

Pro Ala Asp Leu Pro Phe Asp Leu Met Ser Phe Pro Gly Lys Leu
                180                 185                 190

Arg Ala Gly Phe Gly Ala Leu Gly Phe Arg Pro Ser Pro Asp Arg
                195                 200                 205

Glu Glu Ser Val Glu Glu Phe Val Arg Arg Asn Leu Gly Asp Glu Val
            210                 215                 220

Phe Glu Arg Leu Ile Glu Pro Phe Cys Ser Gly Val Tyr Ala Gly Asp
225                 230                 235                 240

Pro Ser Lys Leu Ser Met Lys Ala Ala Phe Gly Lys Val Trp Asn Leu
                245                 250                 255

Glu Gln Asn Gly Gly Ser Ile Val Gly Gly Ala Phe Lys Ala Ile Gln
            260                 265                 270

Asp Arg Lys Asn Ser Gln Lys Pro Pro Arg Asp Pro Arg Leu Pro Lys
            275                 280                 285

Pro Lys Gly Gln Thr Val Gly Ser Phe Arg Lys Gly Gln Ala Met Leu
            290                 295                 300

Pro Asn Ala Ile Ser Thr Arg Leu Gly Ser Arg Val Lys Leu Cys Trp
305                 310                 315                 320

Lys Leu Thr Ser Ile Ser Lys Leu Glu Asn Arg Gly Tyr Asn Leu Thr
                325                 330                 335

Tyr Glu Thr Pro Gln Gly Phe Glu Ser Leu Gln Thr Lys Thr Ile Val
            340                 345                 350

Met Thr Val Pro Ser Tyr Val Ala Ser Asp Leu Leu Arg Pro Leu Ser
            355                 360                 365

Leu Gly Ala Ala Asp Ala Leu Ser Lys Phe Tyr Tyr Pro Pro Val Ala
            370                 375                 380

Ala Val Ser Ile Ser Tyr Pro Lys Asp Ala Ile Arg Ala Asp Arg Leu
385                 390                 395                 400

Ile Asp Gly Gln Leu Lys Gly Phe Gly Gln Leu His Pro Arg Ser Gln
                405                 410                 415

Gly Val Glu Thr Leu Gly Thr Ile Tyr Ser Ser Ser Leu Phe Pro Asn
```

```
                420              425              430
Arg Ala Pro Pro Gly Arg Val Leu Leu Asn Tyr Ile Gly Gly Ala
            435              440              445

Thr Asn Pro Glu Ile Leu Ser Lys Thr Glu Gly Ile Val Asp Ala
        450              455              460

Val Asp Arg Asp Leu Arg Thr Met Leu Ile Arg Asp Ala Glu Asp
465              470              475              480

Pro Leu Thr Leu Gly Val Arg Val Trp Pro Arg Ala Ile Pro Gln Phe
                485              490              495

Leu Ile Gly His Tyr Asp Ile Leu Asp Ser Ala Lys Ala Ala Leu Ser
            500              505              510

Ser Gly Gly Phe Gln Gly Met Phe Leu Gly Gly Asn Tyr Val Ser Gly
        515              520              525

Val Ala Leu Gly Lys Cys Val Glu Ala Ala Tyr Asp Val Ala Ala Glu
            530              535              540

Val Met Asn Phe Leu Ser Gln Gly Val Tyr Lys
545              550              555

<210> SEQ ID NO 15
<211> LENGTH: 1689
<212> TYPE: DNA
<213> ORGANISM: Spinacia oleracea

<400> SEQUENCE: 15
atgagcgcta tggcgttatc gagtacaatg gcccttttcgt tgccgcaatc ttctatgtca    60
ttatcccatt gtaggcacaa ccgtatcacc attttgattc catcttcgtc gcttcgaaga   120
cgaggaggaa gctctatccg ctgctctaca atctcaacct ctaattccgc ggctgcagcc   180
aattaccaga acaaaaacat aggcacaaac ggagttgacg gcggcggagg cggaggaggt   240
gtgttagact gtgtgattgt aggaggtgga atcagtggac tttgcattgc acaggctcta   300
tctactaaat actccaacct ctccacgaat tcattgtca ccgaggctaa ggatcgagtt   360
ggcgggaaca tcactaccat ggaagctgat gggtatttat gggaagaggg tcctaatagc   420
tttcagccat ctgatgcagt gctcaccatg gctgttgaca gtggtttgaa agaggaattg   480
gtgctgggag atcccaattc gcctcgcttt gtgctgtgga atggcaaatt aaggcctgta   540
ccttccaagc tcactgacct cccttttcttt gatctcatga gcttccctgg aaagattagg   600
gctggtcttg gtgctcttgg cttacgacca tctcctccgg ctcatgagga atccgttgaa   660
caatttgtcc gtcgtaatct tggtgatgag gtctttgaac gcttgatcga accttttgt    720 tcaggtgtgt atgctggtga tccttccaag ttgagtatga aagctgcttt tggcagggtt   780
tgggtcttgg agcaaaaggg tggtagtatc attggtggca ccctcaaaac aatccaggaa   840
agaaaggata tcctaagcc acctcgagac ccgcgcctcc ccaaaccaaa gggccagaca   900
gttggatcct tcaggaaagg actgagtatg ttgccaaccg ccatttctga aaggcttggc   960
aacaaagtga agtatcatg gaccctttct ggtattgcta agtcgtcgaa cggagagtat  1020
aatctgactt atgaaacacc agatggactg gtttccgtta ggaccaaaag tgttgtgatg  1080
actgtcccgt catatgttgc aagtagcctc cttcgtccac tttcagatgt cgccgcagaa  1140
tctctttcaa aatttcatta tccaccagtt gcagctgtgt cactttccta tcctaaagaa  1200
gcaattagat cagagtgctt gattgacggt gaacttaaag gattcgggca attacattcc  1260
cgcagtcaag gtgtggaaac cttgggaaca atttatagtt catctctttt ccctgggcga  1320
gcaccacctg gtaggacctt gattttgaac tacattggag gtgatactaa ccctggcata  1380
```

-continued

```
ttagacaaga cgaaagatga actagctgaa gcagttgaca gggatttgag aagaattctc   1440 ataaaccota atgcaaaagc tccccgggtt ttgggtgtga gagtatggcc acaagcaatt   1500
ccccaatttt taattggcca ctttgatctg ctcgatgcag caaaagctgc tttgactgat   1560
ggtggacaca aaggattgtt tcttggtgga aactatgtat caggtgttgc tttgggccga   1620
tgtatagagg gtgcttatga atctgcagcc gaggttgtag attttctgtc acagtactcg   1680
gataaatag                                                           1689
```

<210> SEQ ID NO 16
<211> LENGTH: 562
<212> TYPE: PRT
<213> ORGANISM: Spinacia

<400> SEQUENCE: 16

| | | | | | | | | | | | | | | |
|---|---|---|---|---|---|---|---|---|---|---|---|---|---|---|
| Met | Ser | Ala | Met | Ala | Leu | Ser | Ser | Thr | Met | Ala | Leu | Ser | Leu | Pro | Gln |
| 1 | | | | 5 | | | | | 10 | | | | | 15 | |
| Ser | Ser | Met | Ser | Leu | Ser | His | Cys | Arg | His | Asn | Arg | Ile | Thr | Ile | Leu |
| | | | 20 | | | | | 25 | | | | | 30 | | |
| Ile | Pro | Ser | Ser | Ser | Leu | Arg | Arg | Gly | Gly | Ser | Ser | Ile | Arg | Cys | |
| | | 35 | | | | | 40 | | | | | 45 | | | |
| Ser | Thr | Ile | Ser | Thr | Ser | Asn | Ser | Ala | Ala | Ala | Asn | Tyr | Gln | Asn | |
| | 50 | | | | | 55 | | | | | 60 | | | | |
| Lys | Asn | Ile | Gly | Thr | Asn | Gly | Val | Asp | Gly | Gly | Gly | Gly | Gly | Gly | |
| 65 | | | | | 70 | | | | | 75 | | | | | 80 |
| Val | Leu | Asp | Cys | Val | Ile | Val | Gly | Gly | Gly | Ile | Ser | Gly | Leu | Cys | Ile |
| | | | | 85 | | | | | 90 | | | | | 95 | |
| Ala | Gln | Ala | Leu | Ser | Thr | Lys | Tyr | Ser | Asn | Leu | Ser | Thr | Asn | Phe | Ile |
| | | | 100 | | | | | 105 | | | | | 110 | | |
| Val | Thr | Glu | Ala | Lys | Asp | Arg | Val | Gly | Gly | Asn | Ile | Thr | Thr | Met | Glu |
| | | 115 | | | | | 120 | | | | | 125 | | | |
| Ala | Asp | Gly | Tyr | Leu | Trp | Glu | Glu | Gly | Pro | Asn | Ser | Phe | Gln | Pro | Ser |
| | 130 | | | | | 135 | | | | | 140 | | | | |
| Asp | Ala | Val | Leu | Thr | Met | Ala | Val | Asp | Ser | Gly | Leu | Lys | Glu | Glu | Leu |
| 145 | | | | | 150 | | | | | 155 | | | | | 160 |
| Val | Leu | Gly | Asp | Pro | Asn | Ser | Pro | Arg | Phe | Val | Leu | Trp | Asn | Gly | Lys |
| | | | | 165 | | | | | 170 | | | | | 175 | |
| Leu | Arg | Pro | Val | Pro | Ser | Lys | Leu | Thr | Asp | Leu | Pro | Phe | Phe | Asp | Leu |
| | | | 180 | | | | | 185 | | | | | 190 | | |
| Met | Ser | Phe | Pro | Gly | Lys | Ile | Arg | Ala | Gly | Leu | Gly | Ala | Leu | Gly | Leu |
| | | 195 | | | | | 200 | | | | | 205 | | | |
| Arg | Pro | Ser | Pro | Pro | Ala | His | Glu | Glu | Ser | Val | Glu | Gln | Phe | Val | Arg |
| | 210 | | | | | 215 | | | | | 220 | | | | |
| Arg | Asn | Leu | Gly | Asp | Glu | Val | Phe | Glu | Arg | Leu | Ile | Glu | Pro | Phe | Cys |
| 225 | | | | | 230 | | | | | 235 | | | | | 240 |
| Ser | Gly | Val | Tyr | Ala | Gly | Asp | Pro | Ser | Lys | Leu | Ser | Met | Lys | Ala | Ala |
| | | | | 245 | | | | | 250 | | | | | 255 | |
| Phe | Gly | Arg | Val | Trp | Val | Leu | Glu | Gln | Lys | Gly | Gly | Ser | Ile | Ile | Gly |
| | | | 260 | | | | | 265 | | | | | 270 | | |
| Gly | Thr | Leu | Lys | Thr | Ile | Gln | Glu | Arg | Lys | Asp | Asn | Pro | Lys | Pro | Pro |
| | | 275 | | | | | 280 | | | | | 285 | | | |
| Arg | Asp | Pro | Arg | Leu | Pro | Lys | Pro | Lys | Gly | Gln | Thr | Val | Gly | Ser | Phe |
| | 290 | | | | | 295 | | | | | 300 | | | | |
| Arg | Lys | Gly | Leu | Ser | Met | Leu | Pro | Thr | Ala | Ile | Ser | Glu | Arg | Leu | Gly |

```
                305                 310                 315                 320
Asn Lys Val Lys Val Ser Trp Thr Leu Ser Gly Ile Ala Lys Ser Ser
                    325                 330                 335

Asn Gly Glu Tyr Asn Leu Thr Tyr Glu Thr Pro Asp Gly Leu Val Ser
                340                 345                 350

Val Arg Thr Lys Ser Val Val Met Thr Val Pro Ser Tyr Val Ala Ser
                355                 360                 365

Ser Leu Leu Arg Pro Leu Ser Asp Val Ala Ala Glu Ser Leu Ser Lys
            370                 375                 380

Phe His Tyr Pro Pro Val Ala Ala Val Ser Leu Ser Tyr Pro Lys Glu
385                 390                 395                 400

Ala Ile Arg Ser Glu Cys Leu Ile Asp Gly Glu Leu Lys Gly Phe Gly
                405                 410                 415

Gln Leu His Ser Arg Ser Gln Gly Val Glu Thr Leu Gly Thr Ile Tyr
                420                 425                 430

Ser Ser Ser Leu Phe Pro Gly Arg Ala Pro Pro Gly Arg Thr Leu Ile
            435                 440                 445

Leu Asn Tyr Ile Gly Gly Asp Thr Asn Pro Gly Ile Leu Asp Lys Thr
        450                 455                 460

Lys Asp Glu Leu Ala Glu Ala Val Asp Arg Asp Leu Arg Arg Ile Leu
465                 470                 475                 480

Ile Asn Pro Asn Ala Lys Ala Pro Arg Val Leu Gly Val Arg Val Trp
                485                 490                 495

Pro Gln Ala Ile Pro Gln Phe Leu Ile Gly His Phe Asp Leu Leu Asp
                500                 505                 510

Ala Ala Lys Ala Ala Leu Thr Asp Gly Gly His Lys Gly Leu Phe Leu
            515                 520                 525

Gly Gly Asn Tyr Val Ser Gly Val Ala Leu Gly Arg Cys Ile Glu Gly
        530                 535                 540

Ala Tyr Glu Ser Ala Ala Glu Val Val Asp Phe Leu Ser Gln Tyr Ser
545                 550                 555                 560

Asp Lys

<210> SEQ ID NO 17
<211> LENGTH: 1596
<212> TYPE: DNA
<213> ORGANISM: Spinacia oleracea

<400> SEQUENCE: 17
atggtaatac taccggtttc ccagctatca actaatctgg gtttatcgct ggtttcaccc    60
accaagaaca acccagttat gggcaacgtt tctgagcgaa atcaagtcaa tcaacccatt   120
tctgctaaaa gggttgctgt tgttggtgct ggtgttagtg gacttgctgc ggcgtataag   180
ctaaaatcga atggcttgaa tgtgacattg tttgaagctg atagtagagc tggtgggaaa   240
ctcaaaactg ttgtaaagga tggtttgatt tgggatgaag gggcaaatac catgacagag   300
agcgatgagg aggtcacgag tttgtttgat gatctcggga ttcgtgagaa gctacagcta   360
ccaatttcac aaaacaaaag atacattgcc agagatggtc ttcctgtgct gttaccttca   420
aatccagttg cgctcctgaa gagcaatatc ctttcagcaa atctaagct acaaattatg    480 ttggaaccctt tcttttggaa aaaacacaat ggtgctaagg tttctgacga gaatgcccaa   540
gaaagtgtgg ctgagttttt tgagcggcat tttgggaaag agtttgttga ttatttaatt   600
gatccttttg tcgcgggtac aagtggtgga gatcctcaat ctctttctat gcgtcatgca   660
```

```
tttccagaat tatggaatat tgagaacagg tttggttcag tgatttctgg attcattcag    720
tctaaactgt catccaagaa ggaaaagggt ggagaaaagc aatcttctaa taagaagcca    780
cgtgtacgtg gttcgttttc ttttcagggt ggaatgcaga cactagttga cactatatgc    840
aaagagtttg gtgaagatga actcaaactc cagtctgagg ttctttcatt gtcatacagc    900
cataatggaa gccttacatc agagaattgg tcagtgtctt ctatgtcaaa cagcaccatc    960
caagatcaac catatgatgc tgtcgttgtg accgccccaa tcaataatgt caaagaactg   1020
aagattatga aagtggaaaa cccatttttct cttgacttca ttccagaggt gagctgtcta   1080
cccctctctg ttattattac tacattcaag aagaccaatg tgaagagacc tcttgagggt   1140
tttggtgttc ttgtaccctc taatgagcaa cataatgggc tgaagactct tggtactttg   1200
ttttcctcaa tgatgtttcc tgatcgtgct ccctctgatg tgtatctata cactaccttt   1260
gttggaggta gcagaaatag agaacttgca aaagcttcaa cggatgaact gaagcaaata   1320
gtttcttctg acctccagca gctgttgggc accgagggcg aacctacttt tgtgaatcat   1380
ttttactgga gcaaagcatt ccctctttat ggacgcaatt acgactcagt tcttagagca   1440
atagagaaga tggaaaggga ccttcctgga cttttttacg caggtaacca taagggtgga   1500
ctgtctgtgg gaaagtcaat agcctctgga tacaaagctg ccgagcttgc gatatcctat   1560
ctcgagtcta acaagatgac cgaggagact atataa                             1596
```

<210> SEQ ID NO 18
<211> LENGTH: 531
<212> TYPE: PRT
<213> ORGANISM: Spinacia

<400> SEQUENCE: 18

```
Met Val Ile Leu Pro Val Ser Gln Leu Ser Thr Asn Leu Gly Leu Ser
1               5                   10                  15

Leu Val Ser Pro Thr Lys Asn Asn Pro Val Met Gly Asn Val Ser Glu
            20                  25                  30

Arg Asn Gln Val Asn Gln Pro Ile Ser Ala Lys Arg Val Ala Val Val
        35                  40                  45

Gly Ala Gly Val Ser Gly Leu Ala Ala Ala Tyr Lys Leu Lys Ser Asn
    50                  55                  60

Gly Leu Asn Val Thr Leu Phe Glu Ala Asp Ser Arg Ala Gly Gly Lys
65                  70                  75                  80

Leu Lys Thr Val Val Lys Asp Gly Leu Ile Trp Asp Glu Gly Ala Asn
                85                  90                  95

Thr Met Thr Glu Ser Asp Glu Glu Val Thr Ser Leu Phe Asp Asp Leu
            100                 105                 110

Gly Ile Arg Glu Lys Leu Gln Leu Pro Ile Ser Gln Asn Lys Arg Tyr
        115                 120                 125

Ile Ala Arg Asp Gly Leu Pro Val Leu Leu Pro Ser Asn Pro Val Ala
    130                 135                 140

Leu Leu Lys Ser Asn Ile Leu Ser Ala Lys Ser Lys Leu Gln Ile Met
145                 150                 155                 160

Leu Glu Pro Phe Leu Trp Lys Lys His Asn Gly Ala Lys Val Ser Asp
                165                 170                 175

Glu Asn Ala Gln Glu Ser Val Ala Glu Phe Phe Glu Arg His Phe Gly
            180                 185                 190

Lys Glu Phe Val Asp Tyr Leu Ile Asp Pro Val Ala Gly Thr Ser
        195                 200                 205
```

Gly Gly Asp Pro Gln Ser Leu Ser Met Arg His Ala Phe Pro Glu Leu
     210                 215                 220

Trp Asn Ile Glu Asn Arg Phe Gly Ser Val Ile Ser Gly Phe Ile Gln
225                 230                 235                 240

Ser Lys Leu Ser Ser Lys Lys Glu Lys Gly Gly Glu Lys Gln Ser Ser
                245                 250                 255

Asn Lys Lys Pro Arg Val Arg Gly Ser Phe Ser Phe Gln Gly Gly Met
            260                 265                 270

Gln Thr Leu Val Asp Thr Ile Cys Lys Glu Phe Gly Glu Asp Glu Leu
        275                 280                 285

Lys Leu Gln Ser Glu Val Leu Ser Leu Ser Tyr Ser His Asn Gly Ser
290                 295                 300

Leu Thr Ser Glu Asn Trp Ser Val Ser Ser Met Ser Asn Ser Thr Ile
305                 310                 315                 320

Gln Asp Gln Pro Tyr Asp Ala Val Val Val Thr Ala Pro Ile Asn Asn
                325                 330                 335

Val Lys Glu Leu Lys Ile Met Lys Val Glu Asn Pro Phe Ser Leu Asp
            340                 345                 350

Phe Ile Pro Glu Val Ser Cys Leu Pro Leu Ser Val Ile Ile Thr Thr
        355                 360                 365

Phe Lys Lys Thr Asn Val Lys Arg Pro Leu Glu Gly Phe Gly Val Leu
370                 375                 380

Val Pro Ser Asn Glu Gln His Asn Gly Leu Lys Thr Leu Gly Thr Leu
385                 390                 395                 400

Phe Ser Ser Met Met Phe Pro Asp Arg Ala Pro Ser Asp Val Tyr Leu
                405                 410                 415

Tyr Thr Thr Phe Val Gly Gly Ser Arg Asn Arg Glu Leu Ala Lys Ala
            420                 425                 430

Ser Thr Asp Glu Leu Lys Gln Ile Val Ser Ser Asp Leu Gln Gln Leu
        435                 440                 445

Leu Gly Thr Glu Gly Glu Pro Thr Phe Val Asn His Phe Tyr Trp Ser
450                 455                 460

Lys Ala Phe Pro Leu Tyr Gly Arg Asn Tyr Asp Ser Val Leu Arg Ala
465                 470                 475                 480

Ile Glu Lys Met Glu Arg Asp Leu Pro Gly Leu Phe Tyr Ala Gly Asn
                485                 490                 495

His Lys Gly Gly Leu Ser Val Gly Lys Ser Ile Ala Ser Gly Tyr Lys
            500                 505                 510

Ala Ala Glu Leu Ala Ile Ser Tyr Leu Glu Ser Asn Lys Met Thr Glu
        515                 520                 525

Glu Thr Ile
    530

<210> SEQ ID NO 19
<211> LENGTH: 1674
<212> TYPE: DNA
<213> ORGANISM: Solanum tuberosum

<400> SEQUENCE: 19
atgacaacaa cggccgtcgc caaccatcct agcattttca ctcaccggtc gccgctgccg      60
tcgccgtcgt cctcctcctc atcgccgtca ttttttattt taaaccgtac gaatttcatt     120
ccttactttt ccacctccaa gcgcaatagt gtcaattgca atggctggag aacacgatgt     180
tccgttgcca aggattatac agttcctccc tcggaagtcg acggtaatca gttcccggag     240

```
ctggattgtg tggtagttgg agcaggaatt agtggactct gcattgctaa ggtgatttcg    300
gctaattatc ccaatttgat ggtgacggag gcgagggatc gtgccggtgg aaacataacg    360
acggtggaaa gagatggata cttatgggaa gaaggtccta acagtttcca gccttcggat    420
cctatgttga caatggctgt agattgtgga ttgaaggatg atttggtgtt gggagatcct    480
gatgcgcctc gctttgtctt gtggaaggat aaactaaggc ctgttcccgg caagctcact    540
gatcttccct tctttgattt gatgagtatc cctggcaagc tcagagctgg ttttggtgcc    600
attggccttc gcccttcacc tccaggttat gaggaatcag ttgagcagtt cgtgcgtcgt    660
aatcttggtg cagaagtctt tgaacgtttg attgaaccat tttgttctgg tgtttacgcc    720
ggtgacccct caaaattgat tatgaaagca gcatttggga agtgtggaa gctagaacaa    780
actggtggta gcattattgg gggaaccttt aaagcaatta aggagagatc cagtaaccct    840
aaaccgcctc gtgatccgcg tttaccaaca ccaaaaggac aaactgttgg atcatttagg    900
aagggtctga aatgctgcc ggatgcaatt tgtgaaagac tgggaagcaa agtaaaacta    960
tcatggaagc tttctagcat tacaaagtca gaaaaaggag atatctctt gacatacgag   1020
acaccagaag gagtagtttc tctgcgaagt cgaagcattg tcatgactgt tccatcctat   1080
gtagcaagca acatattacg ccctctttcg gtcgctgcag cagatgcact ttcaagtttc   1140
tactatcccc cagtagcagc agtgacaatt tcatatcctc aagaggctat tcgtgatgag   1200
cgtctggttg atggtgaact aaagggattt ggcagttgc atccacgttc acagggagtg   1260
gaaacactag gaacaatata tagttcatca ctctttccta accgtgctcc aaatggccgg   1320
gtgctactct tgaactacat tggaggagca acaaatactg aaattgtgtc taagacggag   1380
agccaacttg tggaagcagt tgaccgtgac ctcagaaaaa tgcttataaa acccaaagca   1440
caagatccct ttgttacggg tgtgcgagta tggccacaag ctatcccaca gtttttggtc   1500
ggacatctgg atacactagg tactgcaaaa actgctctaa gtgataatgg gcttgacggg   1560
ctattccttg ggggtaatta tgtgtctggt gtagcattgg gaaggtgtgt tgaaggtgct   1620
tatgaaatag catctgaggt aactggattt ctgtctcagt atgcatacaa atga         1674
```

<210> SEQ ID NO 20  
<211> LENGTH: 557  
<212> TYPE: PRT  
<213> ORGANISM: Solanum tuberosum

<400> SEQUENCE: 20

```
Met Thr Thr Thr Ala Val Ala Asn His Pro Ser Ile Phe Thr His Arg
1               5                   10                  15

Ser Pro Leu Pro Ser Pro Ser Ser Ser Ser Ser Pro Ser Phe Leu
            20                  25                  30

Phe Leu Asn Arg Thr Asn Phe Ile Pro Tyr Phe Ser Thr Ser Lys Arg
            35                  40                  45

Asn Ser Val Asn Cys Asn Gly Trp Arg Thr Arg Cys Ser Val Ala Lys
        50                  55                  60

Asp Tyr Thr Val Pro Pro Ser Glu Val Asp Gly Asn Gln Phe Pro Glu
65                  70                  75                  80

Leu Asp Cys Val Val Gly Ala Gly Ile Ser Gly Leu Cys Ile Ala
                85                  90                  95

Lys Val Ile Ser Ala Asn Tyr Pro Asn Leu Met Val Thr Glu Ala Arg
                100                 105                 110

Asp Arg Ala Gly Gly Asn Ile Thr Thr Val Glu Arg Asp Gly Tyr Leu
            115                 120                 125
```

```
Trp Glu Glu Gly Pro Asn Ser Phe Gln Pro Ser Asp Pro Met Leu Thr
130                 135                 140
Met Ala Val Asp Cys Gly Leu Lys Asp Asp Leu Val Leu Gly Asp Pro
145                 150                 155                 160
Asp Ala Pro Arg Phe Val Leu Trp Lys Asp Lys Leu Arg Pro Val Pro
                165                 170                 175
Gly Lys Leu Thr Asp Leu Pro Phe Phe Asp Leu Met Ser Ile Pro Gly
                180                 185                 190
Lys Leu Arg Ala Gly Phe Gly Ala Ile Gly Leu Arg Pro Ser Pro Pro
            195                 200                 205
Gly Tyr Glu Glu Ser Val Glu Gln Phe Val Arg Arg Asn Leu Gly Ala
        210                 215                 220
Glu Val Phe Glu Arg Leu Ile Glu Pro Phe Cys Ser Gly Val Tyr Ala
225                 230                 235                 240
Gly Asp Pro Ser Lys Leu Ile Met Lys Ala Ala Phe Gly Lys Val Trp
                245                 250                 255
Lys Leu Glu Gln Thr Gly Gly Ser Ile Ile Gly Thr Phe Lys Ala
                260                 265                 270
Ile Lys Glu Arg Ser Ser Asn Pro Lys Pro Pro Arg Asp Pro Arg Leu
            275                 280                 285
Pro Thr Pro Lys Gly Gln Thr Val Gly Ser Phe Arg Lys Gly Leu Arg
290                 295                 300
Met Leu Pro Asp Ala Ile Cys Glu Arg Leu Gly Ser Lys Val Lys Leu
305                 310                 315                 320
Ser Trp Lys Leu Ser Ser Ile Thr Lys Ser Lys Gly Gly Tyr Leu
                325                 330                 335
Leu Thr Tyr Glu Thr Pro Glu Gly Val Val Ser Leu Arg Ser Arg Ser
            340                 345                 350
Ile Val Met Thr Val Pro Ser Tyr Val Ala Ser Asn Ile Leu Arg Pro
            355                 360                 365
Leu Ser Val Ala Ala Ala Asp Ala Leu Ser Ser Phe Tyr Tyr Pro Pro
    370                 375                 380
Val Ala Ala Val Thr Ile Ser Tyr Pro Gln Glu Ala Ile Arg Asp Glu
385                 390                 395                 400
Arg Leu Val Asp Gly Glu Leu Lys Gly Phe Gly Gln Leu His Pro Arg
                405                 410                 415
Ser Gln Gly Val Glu Thr Leu Gly Thr Ile Tyr Ser Ser Leu Phe
            420                 425                 430
Pro Asn Arg Ala Pro Asn Gly Arg Val Leu Leu Leu Asn Tyr Ile Gly
    435                 440                 445
Gly Ala Thr Asn Thr Glu Ile Val Ser Lys Thr Glu Ser Gln Leu Val
450                 455                 460
Glu Ala Val Asp Arg Asp Leu Arg Lys Met Leu Ile Lys Pro Lys Ala
465                 470                 475                 480
Gln Asp Pro Phe Val Thr Gly Val Arg Val Trp Pro Gln Ala Ile Pro
                485                 490                 495
Gln Phe Leu Val Gly His Leu Asp Thr Leu Gly Thr Ala Lys Thr Ala
            500                 505                 510
Leu Ser Asp Asn Gly Leu Asp Gly Leu Phe Leu Gly Gly Asn Tyr Val
        515                 520                 525
Ser Gly Val Ala Leu Gly Arg Cys Val Glu Gly Ala Tyr Glu Ile Ala
530                 535                 540
```

Ser Glu Val Thr Gly Phe Leu Ser Gln Tyr Ala Tyr Lys
545                 550                 555

<210> SEQ ID NO 21
<211> LENGTH: 1608
<212> TYPE: DNA
<213> ORGANISM: Zea mays

<400> SEQUENCE: 21

```
atggtcgccg ccacagccac cgccatggcc accgctgcat cgccgctact caacgggacc      60
cgaatacctg cgcggctccg ccatcgagga ctcagcgtgc gctgcgctgc tgtggcgggc     120
ggcgcggccg aggcaccggc atccaccggc gcgcggctgt ccgcggactg cgtcgtggtg     180
ggcggaggca tcagtggcct ctgcaccgcg caggcgctgg ccacgcggca cggcgtcggg     240
gacgtgcttg tcacggaggc ccgcgcccgc ccggcggca  acattaccac cgtcgagcgc     300
cccgaggaag ggtacctctg gaggagggt cccaacagct tccagccctc cgaccccgtt     360
ctcaccatgg ccgtggacag cggactgaag gatgacttgg ttttgggga  cccaaaacgcg    420
ccgcgtttcg tgctgtggga gggaagctg  aggcccgtgc catccaagcc cgccgaccctc    480
ccgttcttcg atctcatgag catcccaggg aagctcaggg ccggtctagg cgcgcttggc     540
atccgccgc  ctcctccagg ccgcgaagag tcagtggagg agttcgtgcg ccgcaacctc     600
ggtgctgagg tctttgagcg cctcattgag cctttctgct caggtgtcta tgctggtgat     660
ccttctaagc tcagcatgaa ggctgcattt gggaaggttt ggcggttgga agaaactgga     720
ggtagtatta ttgggtggaac catcaagaca attcaggaga ggagcaagaa tccaaaacca    780
ccgagggatg cccgccttcc gaagccaaaa gggcagacag ttgcatctt  caggaagggt     840
cttgccatgc ttccaaatgc cattacatcc agcttgggta gtaaagtcaa actatcatgg     900
aaactcacga gcattacaaa atcagatgac aagggatatg ttttggagta tgaaacgcca     960
gaaggggttg tttcggtgca ggctaaaagt gttatcatga ctattccatc atatgttgct    1020
agcaacattt tgcgtccact ttcaagcgat gctgcagatg ctctatcaag attctattat    1080
ccaccggttg ctgctgtaac tgtttcgtat ccaaaggaag caattagaaa agaatgctta    1140
attgatgggg aactccaggg cttttggccag ttgcatccac gtagtcaagg agttgagaca   1200
ttaggaacaa tatacagttc ctcactcttt ccaaatcgtg ctcctgacgg tagggtgtta   1260
cttctaaact acataggagg tgctacaaac acaggaattt tttccaagac tgaaagtgag   1320
ctggtcgaag cagttgaccg tgacctccga aaaatgctta taaattctac agcagtggac   1380
cctttagtcc ttggtgttcg agtttggcca caagccatac ctcagttcct ggtaggacat   1440
cttgatcttc tggaagccgc aaaagctgcc ctggaccgag gtgctacga  tgggctgttc   1500
ctaggaggga actatgttgc aggagttgcc ctgggcagat gcgttgaggg cgcgtatgaa   1560
agtgcctcgc aaatatctga cttcttgacc aagtatgcct acaagtga              1608
```

<210> SEQ ID NO 22
<211> LENGTH: 535
<212> TYPE: PRT
<213> ORGANISM: Zea mays

<400> SEQUENCE: 22

Met Val Ala Ala Thr Ala Thr Ala Met Ala Thr Ala Ala Ser Pro Leu
1               5                   10                  15

Leu Asn Gly Thr Arg Ile Pro Ala Arg Leu Arg His Arg Gly Leu Ser
            20                  25                  30

-continued

```
Val Arg Cys Ala Ala Val Ala Gly Ala Ala Glu Ala Pro Ala Ser
         35                  40                  45

Thr Gly Ala Arg Leu Ser Ala Asp Cys Val Val Gly Gly Gly Ile
 50                  55                  60

Ser Gly Leu Cys Thr Ala Gln Ala Leu Ala Thr Arg His Gly Val Gly
 65                  70                  75                  80

Asp Val Leu Val Thr Glu Ala Arg Ala Arg Pro Gly Gly Asn Ile Thr
                 85                  90                  95

Thr Val Glu Arg Pro Glu Gly Tyr Leu Trp Glu Gly Pro Asn
                100                 105                 110

Ser Phe Gln Pro Ser Asp Pro Val Leu Thr Met Ala Val Asp Ser Gly
            115                 120                 125

Leu Lys Asp Asp Leu Val Phe Gly Asp Pro Asn Ala Pro Arg Phe Val
130                 135                 140

Leu Trp Glu Gly Lys Leu Arg Pro Val Pro Ser Lys Pro Ala Asp Leu
145                 150                 155                 160

Pro Phe Phe Asp Leu Met Ser Ile Pro Gly Lys Leu Arg Ala Gly Leu
                165                 170                 175

Gly Ala Leu Gly Ile Arg Pro Pro Pro Gly Arg Glu Glu Ser Val
            180                 185                 190

Glu Glu Phe Val Arg Arg Asn Leu Gly Ala Glu Val Phe Glu Arg Leu
        195                 200                 205

Ile Glu Pro Phe Cys Ser Gly Val Tyr Ala Gly Asp Pro Ser Lys Leu
210                 215                 220

Ser Met Lys Ala Ala Phe Gly Lys Val Trp Arg Leu Glu Glu Thr Gly
225                 230                 235                 240

Gly Ser Ile Ile Gly Gly Thr Ile Lys Thr Ile Gln Glu Arg Ser Lys
                245                 250                 255

Asn Pro Lys Pro Pro Arg Asp Ala Arg Leu Pro Lys Pro Lys Gly Gln
            260                 265                 270

Thr Val Ala Ser Phe Arg Lys Gly Leu Ala Met Leu Pro Asn Ala Ile
        275                 280                 285

Thr Ser Ser Leu Gly Ser Lys Val Lys Leu Ser Trp Lys Leu Thr Ser
290                 295                 300

Ile Thr Lys Ser Asp Asp Lys Gly Tyr Val Leu Glu Tyr Glu Thr Pro
305                 310                 315                 320

Glu Gly Val Val Ser Val Gln Ala Lys Ser Val Ile Met Thr Ile Pro
                325                 330                 335

Ser Tyr Val Ala Ser Asn Ile Leu Arg Pro Leu Ser Ser Asp Ala Ala
            340                 345                 350

Asp Ala Leu Ser Arg Phe Tyr Tyr Pro Pro Val Ala Ala Val Thr Val
        355                 360                 365

Ser Tyr Pro Lys Glu Ala Ile Arg Lys Glu Cys Leu Ile Asp Gly Glu
370                 375                 380

Leu Gln Gly Phe Gly Gln Leu His Pro Arg Ser Gln Gly Val Glu Thr
385                 390                 395                 400

Leu Gly Thr Ile Tyr Ser Ser Leu Phe Pro Asn Arg Ala Pro Asp
                405                 410                 415

Gly Arg Val Leu Leu Asn Tyr Ile Gly Gly Ala Thr Asn Thr Gly
            420                 425                 430

Ile Val Ser Lys Thr Glu Ser Glu Leu Val Glu Ala Val Asp Arg Asp
        435                 440                 445

Leu Arg Lys Met Leu Ile Asn Ser Thr Ala Val Asp Pro Leu Val Leu
```

```
                450            455            460
Gly Val Arg Val Trp Pro Gln Ala Ile Pro Gln Phe Leu Val Gly His
465                 470                 475                 480

Leu Asp Leu Leu Glu Ala Ala Lys Ala Ala Leu Asp Arg Gly Gly Tyr
                485                 490                 495

Asp Gly Leu Phe Leu Gly Gly Asn Tyr Val Ala Gly Val Ala Leu Gly
                500                 505                 510

Arg Cys Val Glu Gly Ala Tyr Glu Ser Ala Ser Gln Ile Ser Asp Phe
        515                 520                 525

Leu Thr Lys Tyr Ala Tyr Lys
    530                 535

<210> SEQ ID NO 23
<211> LENGTH: 1635
<212> TYPE: DNA
<213> ORGANISM: Zea mays

<400> SEQUENCE: 23
atgctcgctt tgactgcctc agcctcatcc gcttcgtccc atccttatcg ccacgcctcc      60
gcgcacactc gtcgccccg cctacgtgcg gtcctcgcga tggcgggctc cgacgacccc     120
cgtgcagcgc ccgccagatc ggtcgccgtc gtcggcgccg gggtcagcgg gctcgcggcg     180
gcgtacaggc tcagacagag cggcgtgaac gtaacggtgt cgaagcggc cgacagggcg     240 ggaggaaaga tacggaccaa ttccgagggc gggtttgtct gggatgaagg agctaacacc     300
atgacagaag gtgaatggga ggccagtaga ctgattgatg atcttggtct acaagacaaa     360
cagcagtatc ctaactccca acacaagcgt tacattgtca agatggagc accagcactg     420 attccttcgg atcccatttc gctaatgaaa agcagtgttc tttcgacaaa atcaaagatt     480
gcgttatttt ttgaaccatt tctctacaag aaagctaaca aagaaactc tggaaaagtg     540 tctgaggagc acttgagtga gagtgttggg agcttctgtg aacgccactt tggaagagaa     600
gttgttgact attttgttga tccatttgta gctggaacaa gtgcaggaga tccagagtca     660
ctatctattc gtcatgcatt cccagcattg tggaatttgg aaagaaagta tggttcagtt     720
attgttggtg ccatcttgtc taagctagca gctaaaggtg atccagtaaa gacaagacat     780
gattcatcag ggaaaagaag gaatagacga gtgtcgtttt catttcatgg tggaatgcag     840
tcactaataa atgcacttca caatgaagtt ggagatgata atgtgaagct tggtacagaa     900
gtgttgtcat ggcatgtac atttgatgga gttcctgcac taggcaggtg gtcaatttct     960
gttgattcga aggatagcgg tgacaaggac cttgctagta ccaaaccctt tgatgctgtt    1020
ataatgacag ctccattgtc aaatgtccgg aggatgaagt tcaccaaagg tggagctccg    1080
gttgttcttg actttcttcc taagatggat tatctaccac tatctctcat ggtgactgct    1140
tttaagaagg atgatgtcaa gaaacctctg gaaggatttg gggtcttaat accttacaag    1200
gaacagcaaa aacatggtct gaaaacccct gggactctct tttcctcaat gatgttccca    1260
gatcgagctc ctgatgacca atatttatat acaacatttg ttggggtag ccacaataga    1320 gatcttgctg gagctccaac gtctattctg aaacaacttg tgacctctga ccttaaaaaa    1380
ctcttgggcg tagagggca accaactttt gtcaagcatg tatactgggg aaatgctttt    1440
cctttgtatg gccatgatta tagttctgta ttggaagcta tagaaaagat ggagaaaaac    1500
cttccagggt tcttctacgc aggaaatagc aaggatgggc ttgctgttgg aagtgttata    1560
gcttcaggaa gcaaggctgc tgaccttgca atctcatatc ttgaatctca caccaagcat    1620
```
aataattcac attga                                              1635

<210> SEQ ID NO 24
<211> LENGTH: 544
<212> TYPE: PRT
<213> ORGANISM: Zea mays

<400> SEQUENCE: 24

Met Leu Ala Leu Thr Ala Ser Ala Ser Ala Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Ala Ala Ala Tyr Arg Leu
        50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
        355                 360                 365

```
Met Asp Tyr Leu Pro Leu Ser Leu Met Val Thr Ala Phe Lys Lys Asp
    370                 375                 380
Asp Val Lys Lys Pro Leu Glu Gly Phe Gly Val Leu Ile Pro Tyr Lys
385                 390                 395                 400
Glu Gln Gln Lys His Gly Leu Lys Thr Leu Gly Thr Leu Phe Ser Ser
                405                 410                 415
Met Met Phe Pro Asp Arg Ala Pro Asp Gln Tyr Leu Tyr Thr Thr
                420                 425                 430
Phe Val Gly Gly Ser His Asn Arg Asp Leu Ala Gly Ala Pro Thr Ser
                435                 440                 445
Ile Leu Lys Gln Leu Val Thr Ser Asp Leu Lys Leu Leu Gly Val
    450                 455                 460
Glu Gly Gln Pro Thr Phe Val Lys His Val Tyr Trp Gly Asn Ala Phe
465                 470                 475                 480
Pro Leu Tyr Gly His Asp Tyr Ser Ser Val Leu Glu Ala Ile Glu Lys
                485                 490                 495
Met Glu Lys Asn Leu Pro Gly Phe Phe Tyr Ala Gly Asn Ser Lys Asp
                500                 505                 510
Gly Leu Ala Val Gly Ser Val Ile Ala Ser Gly Ser Lys Ala Ala Asp
                515                 520                 525
Leu Ala Ile Ser Tyr Leu Glu Ser His Thr Lys His Asn Asn Ser His
    530                 535                 540
```

<210> SEQ ID NO 25
<211> LENGTH: 1692
<212> TYPE: DNA
<213> ORGANISM: Chlamydomonas reinhardtii

<400> SEQUENCE: 25

```
atgatgttga cccagactcc tgggaccgcc acggcttcta gccggcggtc gcagatccgc    60
tcggctgcgc acgtctccgc caaggtcgcg cctcggccca cgccattctc ggtcgcgagc   120
cccgcgaccg ctgcgagccc cgcgaccgcg gcggcccgcc gcacactcca ccgcactgct   180
gcggcggcca ctggtgctcc cacggcgtcc ggagccggcg tcgccaagac gctcgacaat   240
gtgtatgacg tgatcgtggt cggtggaggt ctctcgggcc tggtgaccgg ccaggccctg   300
gcggctcagc acaaaattca gaacttcctt gttacggagg ctcgcgagcg cgtcggcggc   360
aacattacgt ccatgtcggg cgatggctac gtgtgggagg agggcccgaa cagcttccag   420
cccaacgata gcatgctgca gattgcggtg gactctggct gcgagaagga ccttgtgttc   480
ggtgaccccca cggctccccg cttcgtgtgg tgggagggca agctgcgccc cgtgccctcg   540
ggcctggacg ccttcacctt cgacctcatg tccatccccg gcaagatccg ccgcgggctg   600
ggcgccatcg gcctcatcaa cggagccatg ccctccttcg aggagagtgt ggagcagttc   660
atccgccgca acctgggcga tgaggtgttc ttccgcctga tcgagcccct ctgctccggc   720
gtgtacgcgg cgaccccctc caagctgtcc atgaaggcgg ccttcaacag gatctggatt   780
ctggagaaga acggcggcag cctggtggga ggtgccatca gctgttccca ggaacgccag   840
tccaacccgg ccccgccgcg ggacccgcgc ctgccgccca gcccaagggg ccagacggtg   900
ggctcgttcc gcaagggcct gaagatgctg ccggacgcca ttgagcgcaa catccccgac   960
aagatccgcg tgaactggaa gctggtgtct ctgggccgcg aggcggacgg gcggtacggg  1020
ctggtgtacg acacgcccga gggccgtgtc aaggtgtttg cccgcgccgt ggctctgacc  1080
gcgcccagct acgtggtggc ggacctggtc aaggagcagg cgcccgccgc cgccgaggcc  1140
```

-continued

```
ctgggctcct tcgactaccc gccggtgggc gccgtgacgc tgtcgtaccc gctgagcgcc    1200
gtgcgggagg agcgcaaggc ctcggacggg tccgtgccgg gcttcggtca gctgcacccg    1260
cgcacgcagg gcatcaccac tctgggcacc atctacagct ccagcctgtt ccccggccgc    1320
gcgcccgagg ccacatgct gctgctcaac tacatcggcg gcaccaccaa ccgcggcatc     1380
gtcaaccaga ccaccgagca gctggtggag caggtggaca aggacctgcg caacatggtc    1440
atcaagcccg acgcgcccaa gcccgtgtg gtgggcgtgc gcgtgtggcc gcgcgccatc     1500
ccgcagttca acctgggcca cctggagcag ctggacaagg cgcgcaaggc gctggacgcg    1560
gcggggctgc agggcgtgca cctgggggc aactacgtca gcggtgtggc cctgggcaag    1620
gtggtggagc acggctacga gtccgcagcc aacctggcca agagcgtgtc caaggccgca    1680
gtcaaggcct aa                                                         1692
```

<210> SEQ ID NO 26
<211> LENGTH: 563
<212> TYPE: PRT
<213> ORGANISM: Chlamydomonas

<400> SEQUENCE: 26

```
Met Met Leu Thr Gln Thr Pro Gly Thr Ala Thr Ala Ser Ser Arg Arg
1               5                   10                  15

Ser Gln Ile Arg Ser Ala Ala His Val Ser Ala Lys Val Ala Pro Arg
            20                  25                  30

Pro Thr Pro Phe Ser Val Ala Ser Pro Ala Thr Ala Ala Ser Pro Ala
        35                  40                  45

Thr Ala Ala Arg Arg Thr Leu His Arg Thr Ala Ala Ala Thr
    50                  55                  60

Gly Ala Pro Thr Ala Ser Gly Ala Gly Val Ala Lys Thr Leu Asp Asn
65                  70                  75                  80

Val Tyr Asp Val Ile Val Gly Gly Leu Ser Gly Leu Val Thr
                85                  90                  95

Gly Gln Ala Leu Ala Ala Gln His Lys Ile Gln Asn Phe Leu Val Thr
            100                 105                 110

Glu Ala Arg Glu Arg Val Gly Gly Asn Ile Thr Ser Met Ser Gly Asp
            115                 120                 125

Gly Tyr Val Trp Glu Glu Gly Pro Asn Ser Phe Gln Pro Asn Asp Ser
        130                 135                 140

Met Leu Gln Ile Ala Val Asp Ser Gly Cys Glu Lys Asp Leu Val Phe
145                 150                 155                 160

Gly Asp Pro Thr Ala Pro Arg Phe Val Trp Trp Glu Gly Lys Leu Arg
                165                 170                 175

Pro Val Pro Ser Gly Leu Asp Ala Phe Thr Phe Asp Leu Met Ser Ile
            180                 185                 190

Pro Gly Lys Ile Arg Ala Gly Leu Gly Ala Ile Gly Leu Ile Asn Gly
        195                 200                 205

Ala Met Pro Ser Phe Glu Glu Ser Val Glu Gln Phe Ile Arg Arg Asn
    210                 215                 220

Leu Gly Asp Glu Val Phe Phe Arg Leu Ile Glu Pro Phe Cys Ser Gly
225                 230                 235                 240

Val Tyr Ala Gly Asp Pro Ser Lys Leu Ser Met Lys Ala Ala Phe Asn
                245                 250                 255

Arg Ile Trp Ile Leu Glu Lys Asn Gly Gly Ser Leu Val Gly Gly Ala
            260                 265                 270
```

```
Ile Lys Leu Phe Gln Glu Arg Gln Ser Asn Pro Ala Pro Pro Arg Asp
            275                 280                 285

Pro Arg Leu Pro Pro Lys Pro Lys Gly Gln Thr Val Gly Ser Phe Arg
            290                 295                 300

Lys Gly Leu Lys Met Leu Pro Asp Ala Ile Glu Arg Asn Ile Pro Asp
305                 310                 315                 320

Lys Ile Arg Val Asn Trp Lys Leu Val Ser Leu Gly Arg Glu Ala Asp
                    325                 330                 335

Gly Arg Tyr Gly Leu Val Tyr Asp Thr Pro Glu Gly Arg Val Lys Val
                340                 345                 350

Phe Ala Arg Ala Val Ala Leu Thr Ala Pro Ser Tyr Val Val Ala Asp
            355                 360                 365

Leu Val Lys Glu Gln Ala Pro Ala Ala Glu Ala Leu Gly Ser Phe
            370                 375                 380

Asp Tyr Pro Pro Val Gly Ala Val Thr Leu Ser Tyr Pro Leu Ser Ala
385                 390                 395                 400

Val Arg Glu Glu Arg Lys Ala Ser Asp Gly Ser Val Pro Gly Phe Gly
                    405                 410                 415

Gln Leu His Pro Arg Thr Gln Gly Ile Thr Thr Leu Gly Thr Ile Tyr
                420                 425                 430

Ser Ser Ser Leu Phe Pro Gly Arg Ala Pro Glu Gly His Met Leu Leu
            435                 440                 445

Leu Asn Tyr Ile Gly Gly Thr Thr Asn Arg Gly Ile Val Asn Gln Thr
            450                 455                 460

Thr Glu Gln Leu Val Glu Gln Val Asp Lys Asp Leu Arg Asn Met Val
465                 470                 475                 480

Ile Lys Pro Asp Ala Pro Lys Pro Arg Val Val Gly Val Arg Val Trp
                    485                 490                 495

Pro Arg Ala Ile Pro Gln Phe Asn Leu Gly His Leu Glu Gln Leu Asp
                500                 505                 510

Lys Ala Arg Lys Ala Leu Asp Ala Ala Gly Leu Gln Gly Val His Leu
            515                 520                 525

Gly Gly Asn Tyr Val Ser Gly Val Ala Leu Gly Lys Val Val Glu His
            530                 535                 540

Gly Tyr Glu Ser Ala Ala Asn Leu Ala Lys Ser Val Ser Lys Ala Ala
545                 550                 555                 560

Val Lys Ala

<210> SEQ ID NO 27
<211> LENGTH: 1734
<212> TYPE: DNA
<213> ORGANISM: Polytomella sp

<400> SEQUENCE: 27
atgtcgagtt ccgcactaag gctattatgc gggcgaacaa gtttctttaa tttatgccaa      60
aaatatcctc cttcctttct gtcacaattg tcgaccttaa atttctcaac ccattcgcct     120
ttcgatagca cttatgatgt cgtcgtcgtt ggtgccggaa tctctgggtt gtctactgcc     180
caagcactta gcattcaaca taagatcgat aatgttctgg ttactgaagc tgatcatcgt     240
gtaggcggta aaattacgac gaaaaggaat aaagatttcc tgtgggagga gggtccaaat     300
agttgcctaa tgaacgacgc tttatatcgc gctgcccgag atgccggcgt ggaatccaaa     360
attctatcgg cggatccaaa attaccacgt tggattctgt ggggtcgtcg tttgcgtgtg     420 gccccccattg gaagctacgc tttaaaatcc gaccttttat ctacccaagg cctactccgt     480
```

```
gccatccgag gagtcacagg ttttggtgtg tcaccggctc cacctaaggg tcaggaggag    540
agcgtggagg gctttgttcg acggacctta ggagacgaga tttttgagcg actcgttgag    600
cccttttgct ccggggttta tgcgggggat cctagcaaat tgtccatgcg tgctgctttc    660
ggaaaacttg tggaattcga agagacgggt gatggtagct tacttcgcgg cgtctttcgt    720
tacgtaatga acaaacgacg cgaaagaagg acgggcgggg cgaaagacgg ggacacggtc    780
cctttgaacg agacggccaa ggcacccaaa tcatcctctg gcccaacagt atcgtctttc    840
gagggggggaa tcgagatcct gcccaaggcc attgcgcaaa agctgggtga tcgagttcgt    900
cttggcctac gactcgtgcg catcgatccc acgcagctcg cggatggtac gacagcgtac    960
cgtctgtcgt accgtcggat gagtcatcaa ggcgatgacg actcgagtcg tacggcaggt   1020
gctgtaccgc gtacggcgga gggggatgtc gcggcggggg acgaggacgc cgtggtggag   1080
gtggtggcga agaaggtcgt gctgacgacg ccggcattcg acgccgcgga catcttgtcg   1140
cgttccggct tggtggcggc ggcgaacccg ttgaaggagg tggattaccc gccagtagcg   1200
ttggtcgttc tttcgtacga cgtcgactcg atttccgcca tacaccgcgt gagtcacgtg   1260
gctcatggcc tcagcggctt tggccaactc caccctcgcc cagagggtct ccgtacatta   1320
ggaaccattt acggcagtac attatttccc aaccgttccc ccgtagctcg tacgacgctt   1380
ttaaatttcg ttggtggatc caccgaccgt gcagtgggt ccgcgatcc aatggctttg    1440
gcgatggagg tggatctgga tctgaaaaag agcgggttga tccgagaggg agctgcgaag   1500
ccagaagtcc tcggggtgaa agtatatcca aaggctattc ctcagtttga tattggtcat   1560
ttggatcgag tggaaaaggc caaaatgatg ttaaagaacg aaaggggggg tgcagattgg   1620
agtggggtca aattggcggg aaattatgtg tgcggcgtcg cagtgggcag atgcatagaa   1680
tttggattcg aaattgcgga gaacttggcg caggaattgg cgagaaaaaa atag         1734
```

<210> SEQ ID NO 28
<211> LENGTH: 577
<212> TYPE: PRT
<213> ORGANISM: Polytomella

<400> SEQUENCE: 28

```
Met Ser Ser Ser Ala Leu Arg Leu Leu Cys Gly Arg Thr Ser Phe Phe
1               5                   10                  15

Asn Leu Cys Gln Lys Tyr Pro Pro Ser Phe Leu Ser Gln Leu Ser Thr
                20                  25                  30

Leu Asn Phe Ser Thr His Ser Pro Phe Asp Ser Thr Tyr Asp Val Val
            35                  40                  45

Val Val Gly Ala Gly Ile Ser Gly Leu Ser Thr Ala Gln Ala Leu Ser
        50                  55                  60

Ile Gln His Lys Ile Asp Asn Val Leu Val Thr Glu Ala Asp His Arg
65                  70                  75                  80

Val Gly Gly Lys Ile Thr Thr Lys Arg Asn Lys Asp Phe Leu Trp Glu
                85                  90                  95

Glu Gly Pro Asn Ser Cys Leu Met Asn Asp Ala Leu Tyr Arg Ala Ala
            100                 105                 110

Arg Asp Ala Gly Val Glu Ser Lys Ile Leu Ser Ala Asp Pro Lys Leu
        115                 120                 125

Pro Arg Trp Ile Leu Trp Gly Arg Arg Leu Arg Val Ala Pro Ile Gly
    130                 135                 140

Ser Tyr Ala Leu Lys Ser Asp Leu Leu Ser Thr Gln Gly Leu Leu Arg
```

```
            145                 150                 155                 160
        Ala Ile Arg Gly Val Thr Gly Phe Gly Val Ser Pro Ala Pro Pro Lys
                        165                 170                 175
        Gly Gln Glu Glu Ser Val Glu Gly Phe Val Arg Arg Thr Leu Gly Asp
                        180                 185                 190
        Glu Ile Phe Glu Arg Leu Val Glu Pro Phe Cys Ser Gly Val Tyr Ala
                        195                 200                 205
        Gly Asp Pro Ser Lys Leu Ser Met Arg Ala Ala Phe Gly Lys Leu Val
                        210                 215                 220
        Glu Phe Glu Glu Thr Gly Asp Gly Ser Leu Leu Arg Gly Val Phe Arg
        225                 230                 235                 240
        Tyr Val Met Asn Lys Arg Glu Arg Thr Gly Gly Ala Lys Asp
                                245                 250                 255
        Gly Asp Thr Val Pro Leu Asn Glu Thr Ala Lys Ala Pro Lys Ser Ser
                        260                 265                 270
        Ser Gly Pro Thr Val Ser Ser Phe Glu Gly Gly Ile Glu Ile Leu Pro
                        275                 280                 285
        Lys Ala Ile Ala Gln Lys Leu Gly Asp Arg Val Arg Leu Gly Leu Arg
                        290                 295                 300
        Leu Val Arg Ile Asp Pro Thr Gln Leu Ala Asp Gly Thr Thr Ala Tyr
        305                 310                 315                 320
        Arg Leu Ser Tyr Arg Arg Met Ser His Gln Gly Asp Asp Ser Ser
                                325                 330                 335
        Arg Thr Ala Gly Ala Val Pro Arg Thr Ala Glu Gly Asp Val Ala Ala
                        340                 345                 350
        Gly Asp Glu Asp Ala Val Val Glu Val Ala Lys Lys Val Val Leu
                        355                 360                 365
        Thr Thr Pro Ala Phe Asp Ala Asp Ile Leu Ser Arg Ser Gly Leu
                        370                 375                 380
        Val Ala Ala Ala Asn Pro Leu Lys Glu Val Asp Tyr Pro Pro Val Ala
        385                 390                 395                 400
        Leu Val Val Leu Ser Tyr Asp Val Asp Ser Ile Ser Ala Ile His Arg
                        405                 410                 415
        Val Ser His Val Ala His Gly Leu Ser Gly Phe Gly Gln Leu His Pro
                        420                 425                 430
        Arg Pro Glu Gly Leu Arg Thr Leu Gly Thr Ile Tyr Gly Ser Thr Leu
                        435                 440                 445
        Phe Pro Asn Arg Ser Pro Val Ala Arg Thr Thr Leu Leu Asn Phe Val
                        450                 455                 460
        Gly Gly Ser Thr Asp Arg Ala Val Gly Ser Ala Asp Pro Met Ala Leu
        465                 470                 475                 480
        Ala Met Glu Val Asp Leu Asp Leu Lys Lys Ser Gly Leu Ile Arg Glu
                        485                 490                 495
        Gly Ala Ala Lys Pro Glu Val Leu Gly Val Lys Val Tyr Pro Lys Ala
                        500                 505                 510
        Ile Pro Gln Phe Asp Ile Gly His Leu Asp Arg Val Glu Lys Ala Lys
                        515                 520                 525
        Met Met Leu Lys Asn Glu Arg Gly Gly Ala Asp Trp Ser Gly Val Lys
                        530                 535                 540
        Leu Ala Gly Asn Tyr Val Cys Gly Val Ala Val Gly Arg Cys Ile Glu
        545                 550                 555                 560
        Phe Gly Phe Glu Ile Ala Glu Asn Leu Ala Gln Glu Leu Ala Arg Lys
                        565                 570                 575
```

Lys

<210> SEQ ID NO 29
<211> LENGTH: 1635
<212> TYPE: DNA
<213> ORGANISM: Sorghum bicolor

<400> SEQUENCE: 29

```
atgctcgctc ggactgccac ggtctcctcc acttcgtccc actcccatcc ttatcgcccc      60
acctccgctc gcagtctccg cctacgtccg gtcctcgcga tggcgggctc cgacgactcc     120
cgcgcagctc ccgccaggtc ggtcgccgtc gtcggcgccg gggtcagcgg gctcgtggcg     180
gcgtacaggc tcaggaagag cggcgtgaat gtgacggtgt cgaggcggc cgacagggcg      240
ggaggaaaga tacggaccaa ttccgagggc gggtttctct gggatgaagg agcgaacacc     300
atgacagaag gtgaattgga ggccagtaga ctgatagatg atctcggtct acaagacaaa     360
cagcagtatc ctaactccca acacaagcgt tacattgtca agatggagc accagcactg     420
attccttcgg atcccatttc gctgatgaaa agcagtgttc tttctacaaa atcaaagatt     480
gcgttatttt ttgaaccatt tctctacaag aaagctaaca caagaaaccc tggaaaagta     540
tctgatgagc atttgagtga gagtgttggg agcttctttg aacgccactt cggaagagaa     600
gttgttgact atcttattga tccatttgta gctggaacaa gtgcaggaga tccagagtca     660
ctatctatt gtcatgcatt cccagcactg tggaatttgg aaagaaaata tggttcagtt     720
gttgttggtg ccatcttgtc taagctaaca gctaaaggtg atccagtaaa gacaagacgt     780
gattcatcag cgaaaagaag gaatagacgc gtgtcgtttt catttcatgg tggaatgcag     840
tcactaataa atgcacttca caatgaagtt ggagatgata atgtgaagct tggtacagaa     900
gtgttgtcat tggcgtgtac attagatgga gcccctgcac caggcgggtg gtcaatttct     960
gatgattcga aggatgctag tgcaaggac cttgctaaaa accaaacctt tgatgctgtt    1020
ataatgacag ctccattgtc aaatgtccag aggatgaagt tcacaaaagg tggagctcct    1080
tttgttctag actttcttcc taaggtggat tatctaccac tatctctcat ggtgactgct    1140
tttaagaagg aagatgtcaa gaaacctctg gaaggatttg gcgtcttaat accctacaag    1200
gaacagcaaa aacatggtct aaaaaccctt gggactctct tctcctcaat gatgttccca    1260
gatcgagctc ctgacgacca atatttatat acaacatttg ttgggggtag ccacaataga    1320
gatcttgctg gagctccaac gtctattctg aaacaacttg tgacctctga ccttaaaaaa    1380
ctcttaggcg tacaggggca accaactttt gtcaagcata tatactgggg aaatgcttt    1440
cctttgtatg gtcatgatta caattctgta ttggaagcta tagaaaagat ggagaaaaat    1500
cttccagggt tcttctacgc aggaaataac aaggatgggc ttgctgttgg gagtgttata    1560
gcttcaggaa gcaaggctgc tgaccttgca atctcgtatc ttgaatctca caccaagcat    1620
aataatttac attga                                                    1635
```

<210> SEQ ID NO 30
<211> LENGTH: 544
<212> TYPE: PRT
<213> ORGANISM: Sorghum

<400> SEQUENCE: 30

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu

```
            20                  25                  30
Ala Met Ala Gly Ser Asp Asp Ser Arg Ala Ala Pro Ala Arg Ser Val
            35                  40                  45
Ala Val Val Gly Ala Gly Val Ser Gly Leu Val Ala Ala Tyr Arg Leu
50                      55                  60
Arg Lys Ser Gly Val Asn Val Thr Val Phe Glu Ala Ala Asp Arg Ala
65                  70                  75                  80
Gly Gly Lys Ile Arg Thr Asn Ser Glu Gly Phe Leu Trp Asp Glu
                85                  90                  95
Gly Ala Asn Thr Met Thr Glu Gly Leu Glu Ala Ser Arg Leu Ile
            100                 105                 110
Asp Asp Leu Gly Leu Gln Asp Lys Gln Gln Tyr Pro Asn Ser Gln His
        115                 120                 125
Lys Arg Tyr Ile Val Lys Asp Gly Ala Pro Ala Leu Ile Pro Ser Asp
    130                 135                 140
Pro Ile Ser Leu Met Lys Ser Ser Val Leu Ser Thr Lys Ser Lys Ile
145                 150                 155                 160
Ala Leu Phe Phe Glu Pro Phe Leu Tyr Lys Lys Ala Asn Thr Arg Asn
                165                 170                 175
Pro Gly Lys Val Ser Asp Glu His Leu Ser Glu Ser Val Gly Ser Phe
            180                 185                 190
Phe Glu Arg His Phe Gly Arg Glu Val Val Asp Tyr Leu Ile Asp Pro
        195                 200                 205
Phe Val Ala Gly Thr Ser Ala Gly Asp Pro Glu Ser Leu Ser Ile Cys
    210                 215                 220
His Ala Phe Pro Ala Leu Trp Asn Leu Glu Arg Lys Tyr Gly Ser Val
225                 230                 235                 240
Val Val Gly Ala Ile Leu Ser Lys Leu Thr Ala Lys Gly Asp Pro Val
                245                 250                 255
Lys Thr Arg Arg Asp Ser Ser Ala Lys Arg Arg Asn Arg Arg Val Ser
            260                 265                 270
Phe Ser Phe His Gly Gly Met Gln Ser Leu Ile Asn Ala Leu His Asn
        275                 280                 285
Glu Val Gly Asp Asp Asn Val Lys Leu Gly Thr Glu Val Leu Ser Leu
    290                 295                 300
Ala Cys Thr Leu Asp Gly Ala Pro Ala Pro Gly Gly Trp Ser Ile Ser
305                 310                 315                 320
Asp Asp Ser Lys Asp Ala Ser Gly Lys Asp Leu Ala Lys Asn Gln Thr
                325                 330                 335
Phe Asp Ala Val Ile Met Thr Ala Pro Leu Ser Asn Val Gln Arg Met
            340                 345                 350
Lys Phe Thr Lys Gly Gly Ala Pro Phe Val Leu Asp Phe Leu Pro Lys
        355                 360                 365
Val Asp Tyr Leu Pro Leu Ser Leu Met Val Thr Ala Phe Lys Lys Glu
    370                 375                 380
Asp Val Lys Lys Pro Leu Glu Gly Phe Gly Val Leu Ile Pro Tyr Lys
385                 390                 395                 400
Glu Gln Gln Lys His Gly Leu Lys Leu Thr Leu Thr Leu Phe Ser Ser
                405                 410                 415
Met Met Phe Pro Asp Arg Ala Pro Asp Asp Gln Tyr Leu Tyr Thr Thr
            420                 425                 430
Phe Val Gly Gly Ser His Asn Arg Asp Leu Ala Gly Ala Pro Thr Ser
        435                 440                 445
```

```
Ile Leu Lys Gln Leu Val Thr Ser Asp Leu Lys Lys Leu Leu Gly Val
    450                 455                 460

Gln Gly Gln Pro Thr Phe Val Lys His Ile Tyr Trp Gly Asn Ala Phe
465                 470                 475                 480

Pro Leu Tyr Gly His Asp Tyr Asn Ser Val Leu Glu Ala Ile Glu Lys
                485                 490                 495

Met Glu Lys Asn Leu Pro Gly Phe Phe Tyr Ala Gly Asn Asn Lys Asp
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Leu His
    530                 535                 540
```

<210> SEQ ID NO 31
<211> LENGTH: 1017
<212> TYPE: DNA
<213> ORGANISM: Chlorella sp

<400> SEQUENCE: 31

```
atggcctcca cagcaacact gcacggcgcg ccctgctgct cggcgcggcc cgtgggccgc    60
cggcatattg cagcaccgag catccagcac aatgggccgc gcctggcggc agggtgcag    120
cagcggaagg gggcagggga gcggcgctcg gcactgcgtg tgcaggccgt ccaggccct    180
cccgagaagg cggggcgag cacagggagc gcagcagacg acagcggcgt ttacgacgtt    240
gtggtcgtgg gcgccggcat ctccggcctc accaccgccc aggcgctgac cacgcagcac    300
agcggcgtgg cgcggcgggt gctggtgacc gagggccgcg accgcgtggg cggcaacatc    360
acctccgtgt ccaacaagga ggaggggctg ctgtgggagg aggggcccaa ctccttccag    420
ccaaacgact ccatcctgca ggccgcgtg gacgccggcg tggcggacca gctggtactg    480
ggcgacccca cggcgccgcg tttgtgtac tgggacaaga agctgcgccc cacgccctcc    540
ggccccgacg cgctcacgtt cgacctgatg agcatcgtgg gcaagatccg gcggggctg    600
ggcgcgctgg gcttcaaggc gcccatgcca gactatgagg agagcgtgga gcagtatgtg    660
cggcgcaacc tgggggccga ggtgtttgag cgcctgatcg agcccttctg cagcggcgtg    720
tacgccggcg acccccaagaa gctgtccatg aaggcggcct ttggcaaggt gtacgacctg    780
gagaagaagg cggcagcat cgtgggcggc gtgatcaagc tgattcagga gcggcgcgcc    840
aacccgccgc cgccgcgcag cccagcgctg ccgcccaagc cgcggggcca gacggtgggc    900
tccttccgct ccggcctgcg cacgctgccg gatgccatgg cggcgcggct gggagacgcg    960
gtgcgcacca gctggcagct caaggagctc agcaaggaag gggaggccta caagtga     1017
```

<210> SEQ ID NO 32
<211> LENGTH: 338
<212> TYPE: PRT
<213> ORGANISM: Chlorella

<400> SEQUENCE: 32

```
Met Ala Ser Thr Ala Thr Leu His Gly Ala Pro Cys Cys Ser Ala Arg
1               5                   10                  15

Pro Val Gly Arg Arg His Ile Ala Ala Pro Ser Ile Gln His Asn Gly
            20                  25                  30

Pro Arg Leu Ala Ala Arg Val Gln Gln Arg Lys Gly Ala Gly Glu Arg
        35                  40                  45

Arg Ser Ala Leu Arg Val Gln Ala Val Gln Ala Pro Pro Glu Lys Ala
```

```
                50                  55                  60
Gly Ala Ser Thr Gly Ser Ala Ala Asp Asp Ser Gly Val Tyr Asp Val
 65                  70                  75                  80

Val Val Val Gly Ala Gly Ile Ser Gly Leu Thr Thr Ala Gln Ala Leu
                 85                  90                  95

Thr Thr Gln His Ser Gly Val Ala Arg Arg Val Leu Val Thr Glu Gly
            100                 105                 110

Arg Asp Arg Val Gly Gly Asn Ile Thr Ser Val Ser Asn Lys Glu Glu
        115                 120                 125

Gly Leu Leu Trp Glu Glu Gly Pro Asn Ser Phe Gln Pro Asn Asp Ser
    130                 135                 140

Ile Leu Gln Ala Ala Val Asp Ala Gly Val Ala Asp Gln Leu Val Leu
145                 150                 155                 160

Gly Asp Pro Thr Ala Pro Arg Phe Val Tyr Trp Asp Lys Lys Leu Arg
                165                 170                 175

Pro Thr Pro Ser Gly Pro Asp Ala Leu Thr Phe Asp Leu Met Ser Ile
            180                 185                 190

Val Gly Lys Ile Arg Ala Gly Leu Gly Ala Leu Gly Phe Lys Ala Pro
        195                 200                 205

Met Pro Asp Tyr Glu Glu Ser Val Glu Gln Tyr Val Arg Arg Asn Leu
    210                 215                 220

Gly Ala Glu Val Phe Glu Arg Leu Ile Glu Pro Phe Cys Ser Gly Val
225                 230                 235                 240

Tyr Ala Gly Asp Pro Lys Lys Leu Ser Met Lys Ala Ala Phe Gly Lys
                245                 250                 255

Val Tyr Asp Leu Glu Lys Lys Gly Gly Ser Ile Val Gly Val Ile
            260                 265                 270

Lys Leu Ile Gln Glu Arg Arg Ala Asn Pro Pro Pro Arg Ser Pro
        275                 280                 285

Ala Leu Pro Pro Lys Pro Ala Gly Gln Thr Val Gly Ser Phe Arg Ser
    290                 295                 300

Gly Leu Arg Thr Leu Pro Asp Ala Met Ala Ala Arg Leu Gly Asp Ala
305                 310                 315                 320

Val Arg Thr Ser Trp Gln Leu Lys Glu Leu Ser Lys Glu Gly Glu Ala
                325                 330                 335

Tyr Lys

<210> SEQ ID NO 33
<211> LENGTH: 1611
<212> TYPE: DNA
<213> ORGANISM: Oryza sativa

<400> SEQUENCE: 33
atggccgccg ccgccgcagc catggccacc gccacctccg ccacggcagc gccgccgctc      60
cgcattcgcg acgccgcgag gaggacccgc cgacgcggcc acgttcgctg cgccgtcgcc     120
agcggcgcgg ccgaggcgcc ccggcgcccc ggggcgcggg tgtcggcgga ctgcgtcgtg     180
gtgggcggcg gcatcagcgg gctctgcacc gcgcaggcgc tggccacaaa gcacggcgtc     240
ggcgacgtgc tcgtcacgga ggcccgcgcc cgccccggcg caacatcac caccgccgag     300 cgcgccggcg agggctacct ctgggaggag gggcccaaca gcttccagcc ttccgacccc     360
gtcctcacca tggccgtgga cagcgggctc aaggacgatc tcgtgttcgg gaccccaac     420 gcgccgcggt tcgtgctgtg ggaggggaag ctaaggccgg tgccgtccaa gcccggcgac     480
```

```
ctgccgttct tcgacctcat gagcatcccc ggcaagctca gggccggcct tggcgcgctc    540
ggcgttcgag cgccacctcc agggcgtgag gagtcggtgg aggacttcgt gcggcgcaac    600
ctcggcgcgg aggtctttga gcgcctcatt gagcctttct gctcaggtgt gtatgctggt    660
gatccttcaa agctcagtat gaaggctgca tttgggaagg tgtggaggct ggaggatact    720
ggaggtagca ttattggtgg aaccatcaaa acaatccagg agagggggaa aaaccccaaa    780
ccgccgaggg atccccgcct tccaacgcca aggggcagac agttgcatct tttcaggaag    840
ggtctgacta tgctcccgga tgctattaca tctaggttgg gtagcaaagt caaactttca    900
tggaagttga caagcattac aaagtcagac aacaaaggat atgcattagt gtatgaaaca    960
ccagaagggg tggtctcggt gcaagctaaa actgttgtca tgaccatccc atcatatgtt   1020
gctagtgata tcttgcggcc actttcaagt gatgcagcag atgctctgtc aatattctat   1080
tatccaccag ttgctgctgt aactgtttca tatccaaaag aagcaattag aaaagaatgc   1140
ttaattgacg gagagctcca gggtttcggc cagctgcatc cgcgtagtca gggagttgag   1200
actttaggaa caatatatag ctcatcactc tttccaaatc gtgctccagc tggaagggtg   1260
ttacttctga actacatagg aggttctaca aatacaggga ttgtttccaa gactgaaagt   1320
gagctggtag aagcagttga ccgtgacctc aggaagatgc tgataaatcc taaagcagtg   1380 gacccttttgg tccttggcgt ccgggtatgg ccacaagcca taccacagtt cctcattggc   1440
catcttgatc atcttgaggc tgcaaaatct gccctgggca aggtggtta tgatggattg   1500 ttcctcggag ggaactatgt tgcaggagtt gccctgggcc gatgcgttga aggtgcatat   1560
gagagtgcct cacaaaatatc tgactacttg accaagtacg cctacaagtg a           1611
```

<210> SEQ ID NO 34
<211> LENGTH: 536
<212> TYPE: PRT
<213> ORGANISM: Oryza sativa

<400> SEQUENCE: 34

```
Met Ala Ala Ala Ala Ala Met Ala Thr Ala Thr Ser Ala Thr Ala
1               5                  10                  15

Ala Pro Pro Leu Arg Ile Arg Asp Ala Ala Arg Arg Thr Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175
```

| | | | | | | | | | | | |
|---|---|---|---|---|---|---|---|---|---|---|---|
|Leu|Gly|Ala|Leu|Gly|Val|Arg|Ala|Pro|Pro|Gly|Arg|Glu|Ser|
| | |180| | | |185| | | |190| |

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
        210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
        290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
        370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Leu Phe Pro Asn Arg Ala Pro
                405                 410                 415

Ala Gly Arg Val Leu Leu Leu Asn Tyr Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
        530                 535

<210> SEQ ID NO 35
<211> LENGTH: 1518
<212> TYPE: DNA
<213> ORGANISM: Amaranthus tuberculatus

<400> SEQUENCE: 35
atgggcaaca tttctgagcg ggatgaaccc acttctgcta aagggttgc tgttgttggt     60

```
gctggagtta gtggacttgc tgctgcatat aagctaaaat cccatggttt gaatgtgaca    120
ttgtttgaag ctgattctag agctggaggc aaacttaaaa ctgttaaaaa agatggtttt    180
atttgggatg aggggggcaaa tactatgaca gaaagtgagg cagaagtctc gagtttgatc    240
gatgatcttg gcttcgtga aagcaacag ttgccaattt cacaaaataa aagatacata    300
gctagagatg gtcttcctgt gctactacct tcaaatcccg ctgcactgct cacgagcaat    360
atcctttcag caaaatcaaa gctgcaaatt atgttggaac cattttctg gagaaaacac    420
aatgctactg agctttctga tgagcatgtt caggaaagcg ttggtgaatt ttttgagcga    480
cattttggga aagagtttgt tgattatgtt attgaccctt tgttgcggg tacatgtggt    540
ggagatcctc aatcgctttc tatgcaccat acatttccag aagtatggaa tattgaaaaa    600
aggtttggct ctgtgtttgc tggactaatt caatcaacat tgttatctaa gaaggaaaag    660
ggtggaggag gaaatgcttc tatcaagaag cctcgtgtac gtggttcatt tcattccat    720
ggtgaatgc agacacttgt tgacacaata tgcaaacagc ttggtgaaga tgaactcaaa    780
ctccagtgtg aggtgctgtc cttgtcatac aaccagaagg ggatcccttc attagggaat    840
tggtcagtct cttctatgtc aaataatacc agtgaagatc aatcttatga tgctgtggtt    900
gtcactgctc caattcgcaa tgtcaaagaa atgaagatta tgaaattcgg aaatccattt    960
tcacttgact ttattccaga ggtgagttac gtaccctct ctgttatgat tactgcattc   1020
aagaaggata aagtgaagag accactcgag ggctttggag ttcttatccc ctctaaagag   1080
caacataatg gactgaagac tcttggtact ttatttcct ccatgatgtt tcccgatcgt   1140
gctccatctg acatgtgtct ctttactaca tttgtcggag aagcagaaa tagaaaactt   1200
gcaaacgctt caacggatga attgaagcaa atagtttctt ctgaccttca gcagctgttg   1260
ggcactgagg acgaaccttc atttgtcaat catctctttt ggagcaacgc attcccgttg   1320
tatggacaca attacgattc tgttttgaga gccatagaca agatggaaaa ggatcttcct   1380
ggattttttt atgcaggtaa ccataagggt ggactttcag tgggaaaagc gatggcctcc   1440
ggatgcaagg ctgcggaact tgtaatatcc tatctggact ctcatatata tgtgaagatg   1500
gatgagaaga ccgcgtaa                                                1518
```

<210> SEQ ID NO 36
<211> LENGTH: 505
<212> TYPE: PRT
<213> ORGANISM: Amaranthus

<400> SEQUENCE: 36

```
Met Gly Asn Ile Ser Glu Arg Asp Glu Pro Thr Ser Ala Lys Arg Val
1               5                   10                  15

Ala Val Val Gly Ala Gly Val Ser Gly Leu Ala Ala Tyr Lys Leu
            20                  25                  30

Lys Ser His Gly Leu Asn Val Thr Leu Phe Glu Ala Asp Ser Arg Ala
        35                  40                  45

Gly Gly Lys Leu Lys Thr Val Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
            100                 105                 110
```

Pro Ala Ala Leu Leu Thr Ser Asn Ile Leu Ser Ala Lys Ser Lys Leu
                115                 120                 125

Gln Ile Met Leu Glu Pro Phe Phe Trp Arg Lys His Asn Ala Thr Glu
        130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
                180                 185                 190

Pro Glu Val Trp Asn Ile Glu Lys Arg Phe Gly Ser Val Phe Ala Gly
                195                 200                 205

Leu Ile Gln Ser Thr Leu Leu Ser Lys Lys Glu Lys Gly Gly Gly Gly
                210                 215                 220

Asn Ala Ser Ile Lys Lys Pro Arg Val Arg Gly Ser Phe Ser Phe His
225                 230                 235                 240

Gly Gly Met Gln Thr Leu Val Asp Thr Ile Cys Lys Gln Leu Gly Glu
                245                 250                 255

Asp Glu Leu Lys Leu Gln Cys Glu Val Leu Ser Leu Ser Tyr Asn Gln
                260                 265                 270

Lys Gly Ile Pro Ser Leu Gly Asn Trp Ser Val Ser Ser Met Ser Asn
                275                 280                 285

Asn Thr Ser Glu Asp Gln Ser Tyr Asp Ala Val Val Thr Ala Pro
290                 295                 300

Ile Arg Asn Val Lys Glu Met Lys Ile Met Lys Phe Gly Asn Pro Phe
305                 310                 315                 320

Ser Leu Asp Phe Ile Pro Glu Val Ser Tyr Val Pro Leu Ser Val Met
                325                 330                 335

Ile Thr Ala Phe Lys Lys Asp Lys Val Lys Arg Pro Leu Glu Gly Phe
                340                 345                 350

Gly Val Leu Ile Pro Ser Lys Glu Gln His Asn Gly Leu Lys Thr Leu
                355                 360                 365

Gly Thr Leu Phe Ser Ser Met Met Phe Pro Asp Arg Ala Pro Ser Asp
        370                 375                 380

Met Cys Leu Phe Thr Thr Phe Val Gly Gly Ser Arg Asn Arg Lys Leu
385                 390                 395                 400

Ala Asn Ala Ser Thr Asp Glu Leu Lys Gln Ile Val Ser Ser Asp Leu
                405                 410                 415

Gln Gln Leu Leu Gly Thr Glu Asp Glu Pro Ser Phe Val Asn His Leu
                420                 425                 430

Phe Trp Ser Asn Ala Phe Pro Leu Tyr Gly His Asn Tyr Asp Ser Val
435                 440                 445

Leu Arg Ala Ile Asp Lys Met Glu Lys Asp Leu Pro Gly Phe Phe Tyr
450                 455                 460

Ala Gly Asn His Lys Gly Gly Leu Ser Val Gly Lys Ala Met Ala Ser
465                 470                 475                 480

Gly Cys Lys Ala Ala Glu Leu Val Ile Ser Tyr Leu Asp Ser His Ile
                485                 490                 495

Tyr Val Lys Met Asp Glu Lys Thr Ala
                500                 505

<210> SEQ ID NO 37
<211> LENGTH: 1521
<212> TYPE: DNA

<213> ORGANISM: Arabidopsis thaliana

<400> SEQUENCE: 37

```
atggagttat ctcttctccg tccgacgact caatcgcttc ttccgtcgtt ttcgaagccc      60
aatctccgat taaatgttta taagcctctt agactccgtt gttcagtggc cggtggacca     120
accgtcggat cttcaaaaat cgaaggcgga ggaggcacca ccatcacgac ggattgtgtg     180
attgtcggcg gaggtattag tggtctttgc atcgctcagg cgcttgctac taagcatcct     240
gatgctgctc cgaatttaat tgtgaccgag gctaaggatc gtgttggagg caacattatc     300
actcgtgaag agaatggttt tctctgggaa gaaggtccca atagttttca accgtctgat     360
cctatgctca ctatggtggt agatagtggt ttgaaggatg atttggtgtt gggagatcct     420
actgcgccaa ggtttgtgtt gtggaatggg aaattgaggc cggttccatc gaagctaaca     480
gacttaccgt tctttgattt tgatgagtat tggtgggaaga ttagagctgg ttttggtgca    540
cttggcattc gaccgtcacc tccaggtcgt gaagaatctg tggaggagtt tgtacggcgt     600
aacctcggtg atgaggtttt tgagcgcctg attgaaccgt tttgttcagg tgtttatgct     660
ggtgatcctt caaaactgag catgaaagca gcgtttggga aggtttggaa actagagcaa     720
aatggtggaa gcataatagg tggtactttt aaggcaattc aggagaggaa aaacgctccc     780
aaggcagaac gagacccgcg cctgccaaaa ccacagggcc aaacagttgg ttctttcagg     840
aagggacttc gaatgttgcc agaagcaata tctgcaagat taggtagcaa agttaagttg     900
tcttggaagc tctcaggtat cactaagctg gagagcggag gatacaactt aacatatgag     960
actccagatg gtttagtttc cgtgcagagc aaaagtgttg taatgacggt gccatctcat    1020
gttgcaagtg gtctcttgcg ccctctttct gaatctgctg caaatgcact ctcaaaacta    1080
tattacccac cagttgcagc agtatctatc tcgtacccga agaagcaat ccgaacagaa     1140
tgtttgatag atggtgaact aaagggtttt gggcaattgc atccacgcac gcaaggagtt    1200
gaaacattag aactatcta cagctcctca ctctttccaa atcgcgcacc gcccggaaga     1260
attttgctgt tgaactacat tggcgggtct acaaacaccg gaattctgtc caagtctgaa    1320
ggtgagttag tggaagcatt tctagttggt cactttgata tccttgacac ggctaaatca    1380
tctctaacgt cttcgggcta cgaagggcta ttttgggtg gcaattacgt cgctggtgta    1440
gccttaggcc ggtgtgtaga aggcgcatat gaaaccgcga ttgaggtcaa caacttcatg    1500
tcacggtacg cttacaagta a                                              1521
```

<210> SEQ ID NO 38
<211> LENGTH: 506
<212> TYPE: PRT
<213> ORGANISM: Arabidopsis

<400> SEQUENCE: 38

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80
```

```
Asp Ala Ala Pro Asn Leu Ile Val Thr Glu Ala Lys Asp Arg Val Gly
                85                  90                  95
Gly Asn Ile Ile Thr Arg Glu Glu Asn Gly Phe Leu Trp Glu Glu Gly
            100                 105                 110
Pro Asn Ser Phe Gln Pro Ser Asp Pro Met Leu Thr Met Val Val Asp
            115                 120                 125
Ser Gly Leu Lys Asp Asp Leu Val Leu Gly Asp Pro Thr Ala Pro Arg
            130                 135                 140
Phe Val Leu Trp Asn Gly Lys Leu Arg Pro Val Pro Ser Lys Leu Thr
145                 150                 155                 160
Asp Leu Pro Phe Phe Asp Leu Met Ser Ile Gly Gly Lys Ile Arg Ala
                165                 170                 175
Gly Phe Gly Ala Leu Gly Ile Arg Pro Ser Pro Gly Arg Glu Glu
            180                 185                 190
Ser Val Glu Glu Phe Val Arg Arg Asn Leu Gly Asp Glu Val Phe Glu
            195                 200                 205
Arg Leu Ile Glu Pro Phe Cys Ser Gly Val Tyr Ala Gly Asp Pro Ser
            210                 215                 220
Lys Leu Ser Met Lys Ala Ala Phe Gly Lys Val Trp Lys Leu Glu Gln
225                 230                 235                 240
Asn Gly Gly Ser Ile Ile Gly Gly Thr Phe Lys Ala Ile Gln Glu Arg
                245                 250                 255
Lys Asn Ala Pro Lys Ala Glu Arg Asp Pro Arg Leu Pro Lys Pro Gln
            260                 265                 270
Gly Gln Thr Val Gly Ser Phe Arg Lys Gly Leu Arg Met Leu Pro Glu
            275                 280                 285
Ala Ile Ser Ala Arg Leu Gly Ser Lys Val Lys Leu Ser Trp Lys Leu
            290                 295                 300
Ser Gly Ile Thr Lys Leu Glu Ser Gly Gly Tyr Asn Leu Thr Tyr Glu
305                 310                 315                 320
Thr Pro Asp Gly Leu Val Ser Val Gln Ser Lys Ser Val Val Met Thr
                325                 330                 335
Val Pro Ser His Val Ala Ser Gly Leu Leu Arg Pro Leu Ser Glu Ser
                340                 345                 350
Ala Ala Asn Ala Leu Ser Lys Leu Tyr Tyr Pro Pro Val Ala Ala Val
            355                 360                 365
Ser Ile Ser Tyr Pro Lys Glu Ala Ile Arg Thr Glu Cys Leu Ile Asp
            370                 375                 380
Gly Glu Leu Lys Gly Phe Gly Gln Leu His Pro Arg Thr Gln Gly Val
385                 390                 395                 400
Glu Thr Leu Gly Thr Ile Tyr Ser Ser Leu Phe Pro Asn Arg Ala
                405                 410                 415
Pro Pro Gly Arg Ile Leu Leu Asn Tyr Ile Gly Gly Ser Thr Asn
            420                 425                 430
Thr Gly Ile Leu Ser Lys Ser Glu Gly Glu Leu Val Glu Ala Phe Leu
            435                 440                 445
Val Gly His Phe Asp Ile Leu Asp Thr Ala Lys Ser Ser Leu Thr Ser
            450                 455                 460
Ser Gly Tyr Glu Gly Leu Phe Leu Gly Gly Asn Tyr Val Ala Gly Val
465                 470                 475                 480
Ala Leu Gly Arg Cys Val Glu Gly Ala Tyr Glu Thr Ala Ile Glu Val
            485                 490                 495
Asn Asn Phe Met Ser Arg Tyr Ala Tyr Lys
```

<210> SEQ ID NO 39
<211> LENGTH: 1515
<212> TYPE: DNA
<213> ORGANISM: Nicotiana tabacum

<400> SEQUENCE: 39

```
atggctcctt ctgccggaga agataaacac agttctgcga agagagtcgc agtcattggt      60
gcaggcgtca gtgggcttgc tgcagcatac aagttgaaaa tccatggctt gaatgtgaca     120
gtatttgaag cagaagggaa agctggaggg aagttacgta gcgtgagcca agatggcctg     180
atatgggatg aaggggcaaa tactatgact gaaagtgaag gtgatgttac atttttgatt     240
gattctcttg gactccgaga aaagcaacaa tttccacttt cacaaaacaa gcgctacatt     300
gccagaaatg gtactcctgt actgttacct tcaaatccaa ttgatctgat caaaagcaat     360
tttcttttcca ctggatcaaa gcttcagatg cttctggaac caatattatg gaagaataaa     420
aagctctccc aggtgtctga ctcacatgaa agtgtcagtg gattcttcca gcgtcatttt     480
ggaaaggagg ttgttgacta tctaattgac cttttgttg ctggaacgtg tggtggtgat     540
cctgactcgc tttcaatgca ccattcattt ccagagttgt ggaatttaga gaaaaggttt     600
ggctcagtca tacttggagc tattcgatct aagttatccc ctaaaaatga aagaagcaa     660
gggccaccca aaacttcagc aaataagaag cgccagcggg gatcttttc ctttttgggc     720
ggaatgcaaa cacttactga tgcaatatgc aaagatctca gagaagatga acttagacta     780
aactctcagag ttctggaatt atcttgtagc tgtactgagg actctgcgat agatagctgg     840
tcaattattt ctgcctctcc acacaaaagg caatcagaag aagaatcatt tgatgctgta     900
attatgacgg ccccactctg tgatgttaag agtatgaaga ttgctaagag aggaaatcca     960
tttctactca actttattcc tgaggttgat tatgtaccgc tatctgttgt tataaccaca    1020
tttaagaggg aaaacgtaaa gtatcccctt gaggttttg gggttcttgt accttccaag    1080
gagcaacaac atggtctcaa gacactaggc accctcttct cttctatgat gtttccagat    1140
cgggcaccaa acaatgttta tctctatact actttgttg gtggaagccg aaatagagaa    1200
cttgcaaaag cctcaaggac tgagctgaaa gagatagtaa cttctgacct taagcagctg    1260
ttgggtgctg agggagagcc aacatatgtg aatcatctat actggagtaa agcatttcca    1320
ttgtacgggc ataactatga ttcagtccta gatgcaattg acaaaatgga gaaaaatctt    1380
cctggattat tctatgcagg taaccacagg ggggattgt cagttggcaa agcattatct    1440
tctggatgca atgcagctga tcttgttata tcatatcttg aatccgtctc aactgactcc    1500
aaaagacatt gctga                                                     1515
```

<210> SEQ ID NO 40
<211> LENGTH: 504
<212> TYPE: PRT
<213> ORGANISM: Nicotiana

<400> SEQUENCE: 40

```
Met Ala Pro Ser Ala Gly Glu Asp Lys His Ser Ser Ala Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asn Val Thr Val Phe Glu Ala Glu Gly Lys Ala
        35                  40                  45
```

-continued

Gly Gly Lys Leu Arg Ser Val Ser Gln Asp Gly Leu Ile Trp Asp Glu
50              55                  60
Gly Ala Asn Thr Met Thr Glu Ser Glu Gly Asp Val Thr Phe Leu Ile
65              70                  75                  80
Asp Ser Leu Gly Leu Arg Glu Lys Gln Gln Phe Pro Leu Ser Gln Asn
                85                  90                  95
Lys Arg Tyr Ile Ala Arg Asn Gly Thr Pro Val Leu Leu Pro Ser Asn
            100                 105                 110
Pro Ile Asp Leu Ile Lys Ser Asn Phe Leu Ser Thr Gly Ser Lys Leu
        115                 120                 125
Gln Met Leu Leu Glu Pro Ile Leu Trp Lys Asn Lys Lys Leu Ser Gln
130                 135                 140
Val Ser Asp Ser His Glu Ser Val Ser Gly Phe Phe Gln Arg His Phe
145                 150                 155                 160
Gly Lys Glu Val Val Asp Tyr Leu Ile Asp Pro Phe Val Ala Gly Thr
                165                 170                 175
Cys Gly Gly Asp Pro Asp Ser Leu Ser Met His His Ser Phe Pro Glu
            180                 185                 190
Leu Trp Asn Leu Glu Lys Arg Phe Gly Ser Val Ile Leu Gly Ala Ile
        195                 200                 205
Arg Ser Lys Leu Ser Pro Lys Asn Glu Lys Lys Gln Gly Pro Pro Lys
210                 215                 220
Thr Ser Ala Asn Lys Lys Arg Gln Arg Gly Ser Phe Ser Phe Leu Gly
225                 230                 235                 240
Gly Met Gln Thr Leu Thr Asp Ala Ile Cys Lys Asp Leu Arg Glu Asp
                245                 250                 255
Glu Leu Arg Leu Asn Ser Arg Val Leu Glu Leu Ser Cys Ser Cys Thr
            260                 265                 270
Glu Asp Ser Ala Ile Asp Ser Trp Ser Ile Ile Ser Ala Ser Pro His
        275                 280                 285
Lys Arg Gln Ser Glu Glu Glu Ser Phe Asp Ala Val Ile Met Thr Ala
290                 295                 300
Pro Leu Cys Asp Val Lys Ser Met Lys Ile Ala Lys Arg Gly Asn Pro
305                 310                 315                 320
Phe Leu Leu Asn Phe Ile Pro Glu Val Asp Tyr Val Pro Leu Ser Val
                325                 330                 335
Val Ile Thr Thr Phe Lys Arg Glu Asn Val Lys Tyr Pro Leu Glu Gly
            340                 345                 350
Phe Gly Val Leu Val Pro Ser Lys Glu Gln Gln His Gly Leu Lys Thr
        355                 360                 365
Leu Gly Thr Leu Phe Ser Ser Met Met Phe Pro Asp Arg Ala Pro Asn
370                 375                 380
Asn Val Tyr Leu Tyr Thr Thr Phe Val Gly Gly Ser Arg Asn Arg Glu
385                 390                 395                 400
Leu Ala Lys Ala Ser Arg Thr Glu Leu Lys Glu Ile Val Thr Ser Asp
                405                 410                 415
Leu Lys Gln Leu Leu Gly Ala Glu Gly Glu Pro Thr Tyr Val Asn His
            420                 425                 430
Leu Tyr Trp Ser Lys Ala Phe Pro Leu Tyr Gly His Asn Tyr Asp Ser
        435                 440                 445
Val Leu Asp Ala Ile Asp Lys Met Glu Lys Asn Leu Pro Gly Leu Phe
450                 455                 460
Tyr Ala Gly Asn His Arg Gly Gly Leu Ser Val Gly Lys Ala Leu Ser

```
                  465                 470                 475                 480
              Ser Gly Cys Asn Ala Ala Asp Leu Val Ile Ser Tyr Leu Glu Ser Val
                              485                 490                 495

Ser Thr Asp Ser Lys Arg His Cys
                              500

<210> SEQ ID NO 41
<211> LENGTH: 1509
<212> TYPE: DNA
<213> ORGANISM: Glycine max

<400> SEQUENCE: 41
atggcttcct ctgcaacaga cgataaccca agatctgtaa aaagagtagc tgttgttggt      60
gctggggtaa gtgggcttgc tgcggcttac aaattgaaat cacatggtct ggatgtcact     120
gtatttgaag ctgagggaag agctggaggg aggttgagaa gtgtttctca ggatggtcta     180
atttgggatg agggagctaa tacaatgact gaaagtgaaa ttgaggttaa aggtttgatt     240
gatgctcttg gacttcaaga aaagcagcag tttccaatat cacagcataa gcgctatatt     300
gtgaaaaatg gggcaccact tctggtaccc acaaatcctg ctgcactact gaagagtaaa     360
ctgctttctg cacaatcaaa gatccatctc atttttgaac catttatgtg aaaagaagt     420 gacccctcta atgtgtgtga tgaaaattct gtggaaagtg taggcaggtt ctttgaacgt     480 catttttggaa aagaggttgt ggactatctg attgatcctt tgttgggggg cactagtgca     540
gcagatcctg aatctctctc tatgcgccat tctttcccag agctatggaa tttggagaaa     600
aggtttggct ccattatagc cggggcattg caatctaagt tattcgccaa agggaaaaa      660 actggagaaa ataggactgc actaagaaaa acaaacaca agcgtggttc gttttctttc      720
cagggtggga tgcagacact gacagataca ttgtgcaaag agcttggcaa agacgacctt     780
aaattaaatg aaaaggtttt gacattagct tatggtcatg atggaagttc ctcttcacaa     840
aactggtcta ttactagtgc ttctaaccaa agtacacaag atgttgatgc agtaatcatg     900
acggctcctc tatataatgt caaggacatc aagatcacaa aaggggaac tccctttcca     960 cttaattttc ttcccgaggt aagctacgtg ccaatctcag tcatgattac taccttcaaa    1020
aaggagaatg taaagagacc tttggaggga tttggagttc ttgttccttc taaagagcaa    1080
aaaaatggtt taaaaccct tggtacactt ttttcctcta tgatgttccc agatcgtgca     1140
cctagtgatt tatatctcta taccaccttc attggcggaa ctcaaaacag ggaacttgct    1200
caagcttcaa ctgacgagct taggaaaatt gttacttctg acctgagaaa gttgttggga    1260
gcagaggggg aaccaacatt tgttaaccat ttctattgga gtaaaggctt tcctttgtat    1320
ggacgtaact atgggtcagt tcttcaagca attgataaga tagaaaaaga tcttcccgga    1380 ttttttcttttg caggtaacta caaaggtgga ctctcagttg gcaaagcaat agcctcaggc    1440
tgcaaagcag ctgatcttgt gatatcctac ctcaactctg cttcagacaa cacagtgcct    1500
gataaatga                                                             1509

<210> SEQ ID NO 42
<211> LENGTH: 502
<212> TYPE: PRT
<213> ORGANISM: Glycine

<400> SEQUENCE: 42

Met Ala Ser Ser Ala Thr Asp Asp Asn Pro Arg Ser Val Lys Arg Val
1               5                   10                  15
```

```
Ala Val Val Gly Ala Gly Val Ser Gly Leu Ala Ala Tyr Lys Leu
             20                  25                  30

Lys Ser His Gly Leu Asp Val Thr Val Phe Glu Ala Glu Gly Arg Ala
             35                  40              45

Gly Gly Arg Leu Arg Ser Val Ser Gln Asp Gly Leu Ile Trp Asp Glu
         50                  55                  60

Gly Ala Asn Thr Met Thr Glu Ser Glu Ile Glu Val Lys Gly Leu Ile
65                  70                  75                  80

Asp Ala Leu Gly Leu Gln Glu Lys Gln Gln Phe Pro Ile Ser Gln His
                 85                  90                  95

Lys Arg Tyr Ile Val Lys Asn Gly Ala Pro Leu Leu Val Pro Thr Asn
                100                 105             110

Pro Ala Ala Leu Leu Lys Ser Lys Leu Leu Ser Ala Gln Ser Lys Ile
             115                 120                 125

His Leu Ile Phe Glu Pro Phe Met Trp Lys Arg Ser Asp Pro Ser Asn
             130                 135             140

Val Cys Asp Glu Asn Ser Val Glu Ser Val Gly Arg Phe Phe Glu Arg
145                 150                 155                 160

His Phe Gly Lys Glu Val Val Asp Tyr Leu Ile Asp Pro Phe Val Gly
                 165                 170                 175

Gly Thr Ser Ala Ala Asp Pro Glu Ser Leu Ser Met Arg His Ser Phe
             180                 185                 190

Pro Glu Leu Trp Asn Leu Glu Lys Arg Phe Gly Ser Ile Ile Ala Gly
             195                 200                 205

Ala Leu Gln Ser Lys Leu Phe Ala Lys Arg Glu Lys Thr Gly Glu Asn
             210                 215                 220

Arg Thr Ala Leu Arg Lys Asn Lys His Lys Arg Gly Ser Phe Ser Phe
225                 230                 235                 240

Gln Gly Gly Met Gln Thr Leu Thr Asp Thr Leu Cys Lys Glu Leu Gly
                 245                 250             255

Lys Asp Asp Leu Lys Leu Asn Glu Lys Val Leu Thr Leu Ala Tyr Gly
             260                 265                 270

His Asp Gly Ser Ser Ser Ser Gln Asn Trp Ser Ile Thr Ser Ala Ser
             275                 280                 285

Asn Gln Ser Thr Gln Asp Val Asp Ala Val Ile Met Thr Ala Pro Leu
290                 295                 300

Tyr Asn Val Lys Asp Ile Lys Ile Thr Lys Arg Gly Thr Pro Phe Pro
305                 310                 315                 320

Leu Asn Phe Leu Pro Glu Val Ser Tyr Val Pro Ile Ser Val Met Ile
                 325                 330                 335

Thr Thr Phe Lys Lys Glu Asn Val Lys Arg Pro Leu Glu Gly Phe Gly
             340                 345                 350

Val Leu Val Pro Ser Lys Glu Gln Lys Asn Gly Leu Lys Thr Leu Gly
             355                 360                 365

Thr Leu Phe Ser Ser Met Met Phe Pro Asp Arg Ala Pro Ser Asp Leu
             370                 375                 380

Tyr Leu Tyr Thr Thr Phe Ile Gly Gly Thr Gln Asn Arg Glu Leu Ala
385                 390                 395                 400

Gln Ala Ser Thr Asp Glu Leu Arg Lys Ile Val Thr Ser Asp Leu Arg
                 405                 410                 415

Lys Leu Leu Gly Ala Glu Gly Glu Pro Thr Phe Val Asn His Phe Tyr
             420                 425                 430

Trp Ser Lys Gly Phe Pro Leu Tyr Gly Arg Asn Tyr Gly Ser Val Leu
```

```
        435              440               445
Gln Ala Ile Asp Lys Ile Glu Lys Asp Leu Pro Gly Phe Phe Ala
    450                 455                 460
Gly Asn Tyr Lys Gly Gly Leu Ser Val Gly Lys Ala Ile Ala Ser Gly
465                 470                 475                 480
Cys Lys Ala Ala Asp Leu Val Ile Ser Tyr Leu Asn Ser Ala Ser Asp
                485                 490                 495
Asn Thr Val Pro Asp Lys
            500
```

<210> SEQ ID NO 43
<211> LENGTH: 1205
<212> TYPE: DNA
<213> ORGANISM: Cucumis sativus

<400> SEQUENCE: 43

```
agcttccaac cttccgatcc tattctcacc atggtggtgg atagtggctt aaaagatgat      60
ttagttctgg gagacccaga tgcacctcga tttgtattgt ggaatggaaa gctcagacca     120
gtgcctgcga aacctaatga tctacctttc tttgacctga tgagcattgg tggaaaaatc     180
agagcaggct tggtgccct gggcattcgc cctcctcctc caggtcgaga ggaatcagtt     240
gaagaatttg tccgtcggaa ccttggcaat gaagttttg aacgtttgat agagccattt     300
tgttctggtg tatacgctgg tgacccttca agctaagca tgaaagcagc ttttggtaag     360
gtttggaggc tagagcaaaa tggtggtagt attattggtg ggactttcaa agcacttcaa     420
gaaaggaata aaactaccaa accaccaaga gatccgcgtc taccaaagcc taagggccaa     480
actgttggat cttttcggaa aggacttacc atgttgccaa atgctatttc tacttgtttg     540
gggagtaaag taaagtatc ttggaagcta tctagtatca gtaaagtgga tgacggaggt     600
tatagtttga catacgaaac accagaagga ctagtctcca tactaagcag aagtgtcatc     660
atgacggttc cttcttatat tgctggcact ctgttgcgtc caatctcggg gaaagctgca     720
gatgcacttt caaaatttta ttatccacca gttgcatcag tgaccatatc atatccaaaa     780
ggagcaatta ggaaagaatg cttgattgat ggtgaactaa aggggtttgg tcaattgcac     840
cctcgtagcc aggggggtgac tactttggga actatataca gctcatcact ttttcctaat     900
cgagcgccag atgaagggt attgctcttg aactacattg gaggggctac taatactgga     960
attctttctc agacagagag cgagctcata gaagtagttg atcgggattt aagaaaaatc    1020
ctcataaacc caaacgcaga ggatcctcta ccattgagcg tgagggtgtg ccacaagcc    1080
attccacagt tcttgattgg ccatctcgat gttctagaca ccgccaaggc cggactgaga    1140
gaggctggaa tggagggct attttaggt ggaaactatg tatgcggtgt ggccttgggg    1200
agatg                                                             1205
```

<210> SEQ ID NO 44
<211> LENGTH: 401
<212> TYPE: PRT
<213> ORGANISM: Cucumis

<400> SEQUENCE: 44

```
Ser Phe Gln Pro Ser Asp Pro Ile Leu Thr Met Val Val Asp Ser Gly
1               5                   10                  15
Leu Lys Asp Asp Leu Val Leu Gly Asp Pro Asp Ala Pro Arg Phe Val
            20                  25                  30
Leu Trp Asn Gly Lys Leu Arg Pro Val Pro Ala Lys Pro Asn Asp Leu
```

```
                35                  40                  45
        Pro Phe Phe Asp Leu Met Ser Ile Gly Gly Lys Ile Arg Ala Gly Phe
         50                  55                  60

Gly Ala Leu Gly Ile Arg Pro Pro Pro Gly Arg Glu Glu Ser Val
         65                  70                  75                  80

Glu Glu Phe Val Arg Asn Leu Gly Asn Glu Val Phe Glu Arg Leu
                         85                  90                  95

Ile Glu Pro Phe Cys Ser Gly Val Tyr Ala Gly Asp Pro Ser Lys Leu
                        100                 105                 110

Ser Met Lys Ala Ala Phe Gly Lys Val Trp Arg Leu Glu Gln Asn Gly
                        115                 120                 125

Gly Ser Ile Ile Gly Gly Thr Phe Lys Ala Leu Gln Glu Arg Asn Lys
                        130                 135                 140

Thr Thr Lys Pro Pro Arg Asp Pro Arg Leu Pro Lys Pro Lys Gly Gln
        145                 150                 155                 160

Thr Val Gly Ser Phe Arg Lys Gly Leu Thr Met Leu Pro Asn Ala Ile
                        165                 170                 175

Ser Thr Cys Leu Gly Ser Lys Val Lys Val Ser Trp Lys Leu Ser Ser
                        180                 185                 190

Ile Ser Lys Val Asp Asp Gly Gly Tyr Ser Leu Thr Tyr Glu Thr Pro
                        195                 200                 205

Glu Gly Leu Val Ser Ile Leu Ser Arg Ser Val Ile Met Thr Val Pro
        210                 215                 220

Ser Tyr Ile Ala Gly Thr Leu Leu Arg Pro Ile Ser Gly Lys Ala Ala
        225                 230                 235                 240

Asp Ala Leu Ser Lys Phe Tyr Tyr Pro Pro Val Ala Ser Val Thr Ile
                        245                 250                 255

Ser Tyr Pro Lys Gly Ala Ile Arg Lys Glu Cys Leu Ile Asp Gly Glu
                        260                 265                 270

Leu Lys Gly Phe Gly Gln Leu His Pro Arg Ser Gln Gly Val Thr Thr
                        275                 280                 285

Leu Gly Thr Ile Tyr Ser Ser Ser Leu Phe Pro Asn Arg Ala Pro Asp
        290                 295                 300

Gly Arg Val Leu Leu Leu Asn Tyr Ile Gly Gly Ala Thr Asn Thr Gly
        305                 310                 315                 320

Ile Leu Ser Gln Thr Glu Ser Glu Leu Ile Glu Val Val Asp Arg Asp
                        325                 330                 335

Leu Arg Lys Ile Leu Ile Asn Pro Asn Ala Glu Asp Pro Leu Pro Leu
                        340                 345                 350

Ser Val Arg Val Trp Pro Gln Ala Ile Pro Gln Phe Leu Ile Gly His
                        355                 360                 365

Leu Asp Val Leu Asp Thr Ala Lys Ala Gly Leu Arg Glu Ala Gly Met
        370                 375                 380

Glu Gly Leu Phe Leu Gly Gly Asn Tyr Val Cys Gly Val Ala Leu Gly
        385                 390                 395                 400

Arg
```

<210> SEQ ID NO 45
<211> LENGTH: 1521
<212> TYPE: DNA
<213> ORGANISM: Oryza sativa

<400> SEQUENCE: 45
atggccgcct ccgacgaccc ccgcggcggg aggtccgtcg ccgtcgtcgg cgccggcgtc    60

```
agtgggctcg cggcggcgta caggctgagg aagcgcggcg tgcaggtgac ggtgttcgag    120
gcggccgaca gggcgggtgg gaagatacga accaactccg agggcgggtt catctgggac    180
gaagggccca acaccatgac agagagtgaa ttggaggcaa gcaggcttat tgacgatctt    240
ggcctacaag gcaaacagca gtatcctaac tcacaacaca agcgttacat tgtcaaagat    300
ggagcaccaa cactgattcc ctcagatccc attgcgctca tgaaaagcac tgttctttct    360
acaaaatcaa agctcaagct atttctggaa ccatttctct atgagaaatc tagcagaagg    420
acctcgggaa aagtgtctga tgaacattta agtgagagtg tgattttttct gtgtatatgt    480
agagataatc aggttgttga ttatcttatt gatccatttg tggctggaac aagcggagga    540
gatcctgagt cattatcaat tcgtcatgca tttccagcat tatggaattt ggagaataag    600
tatggctctg tcattgctgg tgccatcttg tccaaactat ccactaaggg tgattcagtg    660
aagacaggag gtgcttcgcc agggaaagga aggaataaac gtgtgtcatt ttcatttcat    720
ggtggaatgc agtcactaat agatgcactt cacaatgaag ttggagatgg taacgtgaag    780
cttggtacag aagtgttgtc attggcatgt tgctgtgatg gagtctcttc ttctggtggt    840
tggtcaattt ctgttgattc aaaagatgct aaagggaaag atctcagaaa gaaccaatct    900
ttcgatgctg ttataatgac tgctccattg tctaatgtcc agaggatgaa gtttacaaaa    960
ggtggagttc cctttgtgct agactttctt cctaaggtcg attatctacc actatctctc   1020
atggtaacag cttttaagaa ggaagatgtc aaaaaaccat tggaaggatt tggtgccttg   1080
atacccctata aggaacagca aaagcatggt ctcaaaaccc ttgggaccct cttctcctcg   1140
atgatgtttc cagatcgagc tcctaatgat caatatctat atacatcttt cattgggggg   1200
agccataata gagacctcgc tggggctcca acggctattc tgaaacaact tgtgacctct   1260
gacctaagaa agctcttggg tgttgaggga caacctactt ttgtgaagca tgtacattgg   1320
agaaatgctt ttcctttata tggccagaat tatgatctgg tactgaagc tatagcaaaa   1380
atggagaaca atcttccagg gttcttttac gcaggaaata caaggatgg gttggctgtt   1440
ggaaatgtta tagcttcagg aagcaaggct gctgaccttg tgatctctta tcttgaatct   1500
tgcacagatc aggacaatta g                                             1521
```

<210> SEQ ID NO 46
<211> LENGTH: 506
<212> TYPE: PRT
<213> ORGANISM: Oryza sativa

<400> SEQUENCE: 46

```
Met Ala Ala Ser Asp Asp Pro Arg Gly Gly Arg Ser Val Ala Val Val
1               5                   10                  15

Gly Ala Gly Val Ser Gly Leu Ala Ala Ala Tyr Arg Leu Arg Lys Arg
            20                  25                  30

Gly Val Gln Val Thr Val Phe Glu Ala Ala Asp Arg Ala Gly Gly Lys
        35                  40                  45

Ile Arg Thr Asn Ser Glu Gly Gly Phe Ile Trp Asp Glu Gly Ala Asn
    50                  55                  60

Thr Met Thr Glu Ser Glu Leu Glu Ala Ser Arg Leu Ile Asp Asp Leu
65                  70                  75                  80

Gly Leu Gln Gly Lys Gln Gln Tyr Pro Asn Ser Gln His Lys Arg Tyr
                85                  90                  95

Ile Val Lys Asp Gly Ala Pro Thr Leu Ile Pro Ser Asp Pro Ile Ala
            100                 105                 110
```

```
Leu Met Lys Ser Thr Val Leu Ser Thr Lys Ser Lys Leu Lys Leu Phe
            115                 120                 125

Leu Glu Pro Phe Leu Tyr Glu Lys Ser Ser Arg Arg Thr Ser Gly Lys
        130                 135                 140

Val Ser Asp Glu His Leu Ser Glu Ser Val Ile Phe Leu Cys Ile Cys
145                 150                 155                 160

Arg Asp Asn Gln Val Val Asp Tyr Leu Ile Asp Pro Phe Val Ala Gly
                165                 170                 175

Thr Ser Gly Gly Asp Pro Glu Ser Leu Ser Ile Arg His Ala Phe Pro
            180                 185                 190

Ala Leu Trp Asn Leu Glu Asn Lys Tyr Gly Ser Val Ile Ala Gly Ala
        195                 200                 205

Ile Leu Ser Lys Leu Ser Thr Lys Gly Asp Ser Val Lys Thr Gly Gly
    210                 215                 220

Ala Ser Pro Gly Lys Gly Arg Asn Lys Arg Val Ser Phe Ser Phe His
225                 230                 235                 240

Gly Gly Met Gln Ser Leu Ile Asp Ala Leu His Asn Glu Val Gly Asp
                245                 250                 255

Gly Asn Val Lys Leu Gly Thr Glu Val Leu Ser Leu Ala Cys Cys Cys
            260                 265                 270

Asp Gly Val Ser Ser Gly Gly Trp Ser Ile Ser Val Asp Ser Lys
        275                 280                 285

Asp Ala Lys Gly Lys Asp Leu Arg Lys Asn Gln Ser Phe Asp Ala Val
    290                 295                 300

Ile Met Thr Ala Pro Leu Ser Asn Val Gln Arg Met Lys Phe Thr Lys
305                 310                 315                 320

Gly Gly Val Pro Phe Val Leu Asp Phe Leu Pro Lys Val Asp Tyr Leu
                325                 330                 335

Pro Leu Ser Leu Met Val Thr Ala Phe Lys Lys Glu Asp Val Lys Lys
            340                 345                 350

Pro Leu Glu Gly Phe Gly Ala Leu Ile Pro Tyr Lys Glu Gln Gln Lys
        355                 360                 365

His Gly Leu Lys Thr Leu Gly Thr Leu Phe Ser Ser Met Met Phe Pro
    370                 375                 380

Asp Arg Ala Pro Asn Asp Gln Tyr Leu Tyr Thr Ser Phe Ile Gly Gly
385                 390                 395                 400

Ser His Asn Arg Asp Leu Ala Gly Ala Pro Thr Ala Ile Leu Lys Gln
                405                 410                 415

Leu Val Thr Ser Asp Leu Arg Lys Leu Gly Val Glu Gln Pro
            420                 425                 430

Thr Phe Val Lys His Val His Trp Arg Asn Ala Phe Pro Leu Tyr Gly
        435                 440                 445

Gln Asn Tyr Asp Leu Val Leu Glu Ala Ile Ala Lys Met Glu Asn Asn
    450                 455                 460

Leu Pro Gly Phe Phe Tyr Ala Gly Asn Asn Lys Asp Gly Leu Ala Val
465                 470                 475                 480

Gly Asn Val Ile Ala Ser Gly Ser Lys Ala Ala Asp Leu Val Ile Ser
                485                 490                 495

Tyr Leu Glu Ser Cys Thr Asp Gln Asp Asn
            500                 505

<210> SEQ ID NO 47
<211> LENGTH: 26
```

```
<212> TYPE: DNA
<213> ORGANISM: Artificial Sequence
<220> FEATURE:
<223> OTHER INFORMATION: Forward primer; Cr_PPO1_Fw

<400> SEQUENCE: 47
atgatgttga cccagactcc tgggac                                          26

<210> SEQ ID NO 48
<211> LENGTH: 25
<212> TYPE: DNA
<213> ORGANISM: Artificial Sequence
<220> FEATURE:
<223> OTHER INFORMATION: Reverse primer; Cr_PPO1_Rv

<400> SEQUENCE: 48
ttaggccttg actgcggcct tggac                                           25
```

PLANTS HAVING INCREASED TOLERANCE TO HERBICIDES

This application claims the benefit of U.S. Provisional Application No. 61/661,364, filed Jun. 19, 2012, the entire contents of which are hereby incorporated by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_Listing.txt" created on Jun. 12, 2013, and is 153,475 bytes in size. The sequence listing contained in this .txt file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to "benzoxazinone-derivative" herbicides. More specifically, the present invention relates to methods and plants obtained by mutagenesis and cross-breeding and transformation that have an increased tolerance to "benzoxazinone-derivative" herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260:231). PPO-inhibiting herbicides include many different structural classes of molecules (Duke et al. 1991. Weed Sci. 39:465; Nandihalli et al. 1992. Pesticide Biochem. Physiol. 43:193; Matringe et al. 1989. FEBS Lett. 245:35; Yanase and Andoh. 1989. Pesticide Biochem. Physiol. 35:70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorphthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102:881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39:1155; Dailey et al. 1994. J. Biol. Chem. 269:813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15:449; Shibata et al. 1992. In Research in Photosynthesis, Vol. III, N. Murata, ed. Kluwer: Netherlands. pp. 567-70).

At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPOs.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or U.S. Pat. No. 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

To date, the prior art has not described benzoxazinone-derivative herbicide tolerant plants containing at least one wild-type or mutated PPO nucleic acid. Nor has the prior art described benzoxazinone-derivative herbicide tolerant crop plants containing mutations on genomes other than the genome from which the PPO gene is derived. Therefore, what is needed in the art is the identification of benzoxazinone-derivative herbicide tolerance genes from additional genomes and species. What are also needed in the art are crop plants and crop plants having increased tolerance to herbicides such as benzoxazinone-derivative herbicide and containing at least one wildtype and/or mutated PPO nucleic acid. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

The problem is solved by the present invention which refers to a method for controlling undesired vegetation at a plant cultivation site, the method comprising the steps of:

a) providing, at said site, a plant that comprises at least one nucleic acid comprising a nucleotide sequence encoding a wild type protoporphyrinogen oxidase (PPO) or a mutated protoporphyrinogen oxidase (mut-PPO) which is resistant or tolerant to a benzoxazinone-derivative herbicide, b) applying to said site an effective amount of said herbicide.

In addition, the present invention refers to a method for identifying a benzoxazinone-derivative herbicide by using a wild-type or mut-PPO encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, or 45, or a variant thereof.

Said method comprises the steps of:
a) generating a transgenic cell or plant comprising a nucleic acid encoding a mut-PPO, wherein the mut-PPO is expressed;
b) applying a benzoxazinone-derivative herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a mut-PPO which is resistant or tolerant to a benzoxazinone-derivative herbicide, the method comprising:
a) generating a library of mut-PPO-encoding nucleic acids,
b) screening a population of the resulting mut-PPO-encoding nucleic acids by expressing each of said nucleic acids in a cell or plant and treating said cell or plant with a benzoxazinone-derivative herbicide,
c) comparing the benzoxazinone-derivative herbicide-tolerance levels provided by said population of mut-PPO encoding nucleic acids with the benzoxazinone-derivative herbicide-tolerance level provided by a control PPO-encoding nucleic acid,
d) selecting at least one mut-PPO-encoding nucleic acid that provides a significantly increased level of tolerance to a benzoxazinone-derivative herbicide as compared to that provided by the control PPO-encoding nucleic acid.

In a preferred embodiment, the mut-PPO-encoding nucleic acid selected in step d) provides at least 2-fold as much tolerance to a benzoxazinone-derivative herbicide as compared to that provided by the control PPO-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mut-PPO which is resistant or tolerant to a benzoxazinone-derivative herbicide, the method comprising:
a) identifying an effective amount of a benzoxazinone-derivative herbicide in a culture of plant cells or green algae.
b) treating said plant cells or green algae with a mutagenizing agent,
c) contacting said mutagenized cells population with an effective amount of benzoxazinone-derivative herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, the mutagenizing agent is ethylmethanesulfonate.

Another object refers to an isolated nucleic acid encoding a mut-PPO, the nucleic acid comprising the sequence of SEQ ID NO: 1, 3, 5, 7, 9, 11, 13, 15, 17, 19, 21, 23, 25, 27, 29, 31, 33, 35, 37, 39, 41, 43, or 45, or a variant thereof, as defined hereinafter.

Another object refers to an isolated mut-PPO polypeptide, the polypeptide comprising the sequence set forth in SEQ ID NO: 2, 4, 6, 8, 10, 12, 14, 16, 18, 20, 22, 24, 26, 28, 30, 32, 34, 36, 38, 40, 42, 44, or 46, a variant, derivative, orthologue, paralogue or homologue thereof, as defined hereinafter.

In a preferred embodiment, the nucleic acid being identifiable by a method as defined above.

In another embodiment, the invention refers to a plant cell transformed by a wild-type or a mut-PPO nucleic acid or a plant which has been mutated to obtain a plant expressing, preferably over-expressing a wild-type or a mut-PPO nucleic acid, wherein expression of the nucleic acid in the plant cell results in increased resistance or tolerance to a benzoxazinone-derivative herbicide as compared to a wild type variety of the plant cell.

In another embodiment, the invention refers to a plant comprising a plant cell according to the present invention, wherein expression of the nucleic acid in the plant results in the plant's increased resistance to benzoxazinone-derivative herbicide as compared to a wild type variety of the plant.

The plants of the present invention can be transgenic or non-transgenic.

Preferably, the expression of the nucleic acid of the invention in the plant results in the plant's increased resistance to benzoxazinone-derivative herbicide as compared to a wild type variety of the plant.

In another embodiment, the invention refers to a seed produced by a transgenic plant comprising a plant cell of the present invention, wherein the seed is true breeding for an increased resistance to a benzoxazinone-derivative herbicide as compared to a wild type variety of the seed.

In another embodiment, the invention refers to a method of producing a transgenic plant cell with an increased resistance to a benzoxazinone-derivative herbicide as compared to a wild type variety of the plant cell comprising, transforming the plant cell with an expression cassette comprising a wild-type or a mut-PPO nucleic acid.

In another embodiment, the invention refers to a method of producing a transgenic plant comprising, (a) transforming a plant cell with an expression cassette comprising a wild-type or a mut-PPO nucleic acid, and (b) generating a plant with an increased resistance to benzoxazinone-derivative herbicide from the plant cell.

Preferably, the expression cassette further comprises a transcription initiation regulatory region and a translation initiation regulatory region that are functional in the plant.

In another embodiment, the invention relates to using the mut-PPO of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mut-PPO polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one benzoxazinone-derivative inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mut-PPO proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

BRIEF DESCRIPTION OF THE DRAWINGS

Figure 1:
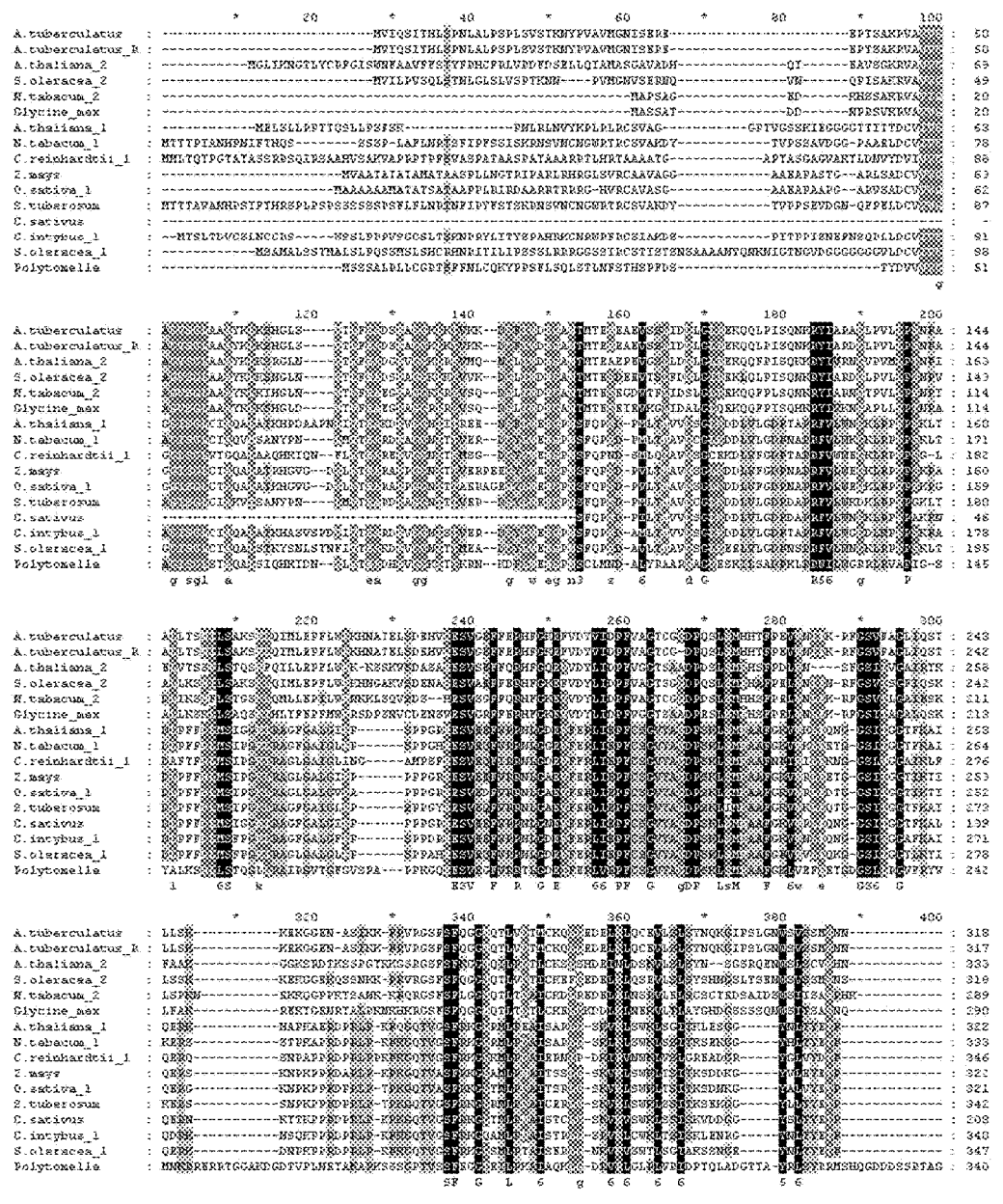
Figure 1:
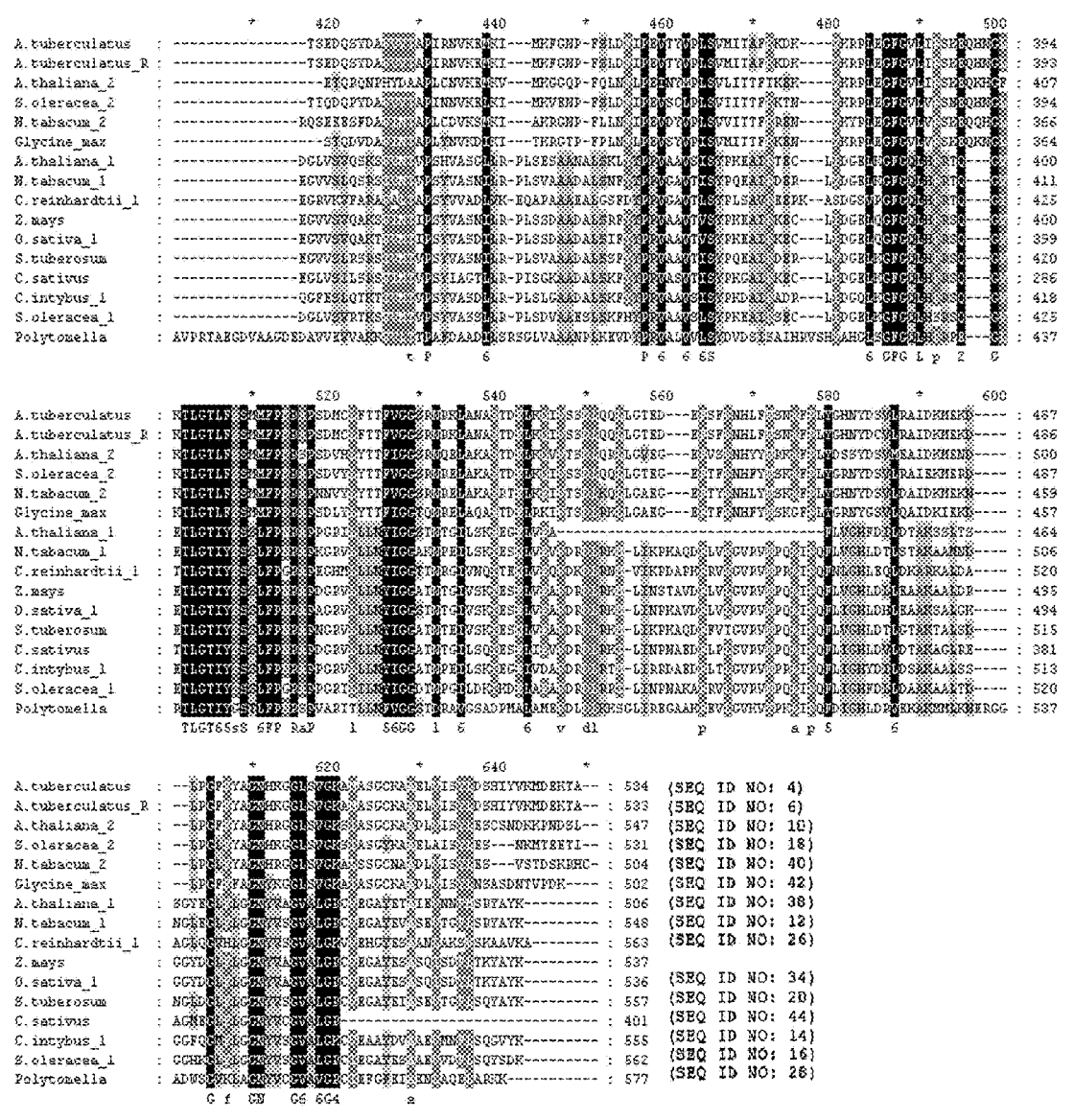

FIG. 1 shows an amino acid sequence alignment of *Amaranthus tuberculatus* (*A. tuberculatus*), *Amaranthus tuberculatus* resistant (*A. tuberculatus*_R), *Arabidopsis thaliana* long (*A. thaliana*_2), *Spinacia oleracea* short (*S. oleracea*_2), *Nicotiana tabacum* short (*N. tabacum*_2), *Glycine* max (*Glycine*_max), *Arabidopsis thaliana* short (*A. thaliana*_1), *Nicotiana tabacum* long (*N. tabacum*_1), *Chlamydomonas reinhardtii* long (*C. reinhardtii*_1), *Zea mays* (*Z. mays*), *Oryza sativa* (*O. sativa*_1), *Solanum tuberosum* (*S. tuberosum*), *Cucumis sativus* (*C. sativus*), *Cichorium intybus* (*C. intybus*_1), *Spinacia oleracea* long (*S. oleracea*_1), *Polytomella* sp. *Pringsheim* 198.80 (*Polytomella*) PPO sequences. Conserved regions are indicated in light grey, grey and black.

SEQUENCE LISTING

TABLE 1

Figure 2:
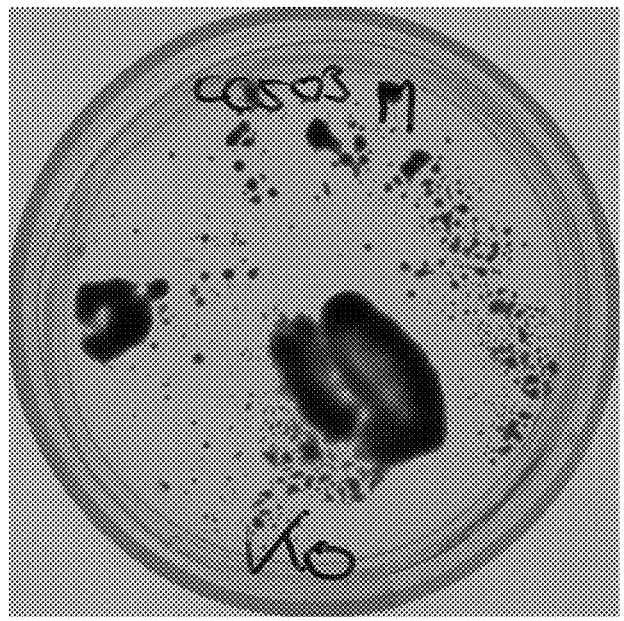
FIG. 2 shows the selection of *Chlamydomonas reinhardtii* strains resistant to benzoxazinone-derivative 1.a.35 herbicide. (A) Mutagenized cells plated on solid medium without a selecting agent. (B) Mutagenized cells plated on solid medium containing $1 \times 10^{-7}$ M benzoxazinone-derivative I.a.35. Cells which are resistant to the benzoxazinone-derivative herbicide form colonies (circled and numbered 31 and 32), while susceptible cells do not grow. The higher number of colonies on plate A as compared to B, indicate that the colonies on plate B are resistant to benzoxazinone-derivative I.a.35.
Figure 2:
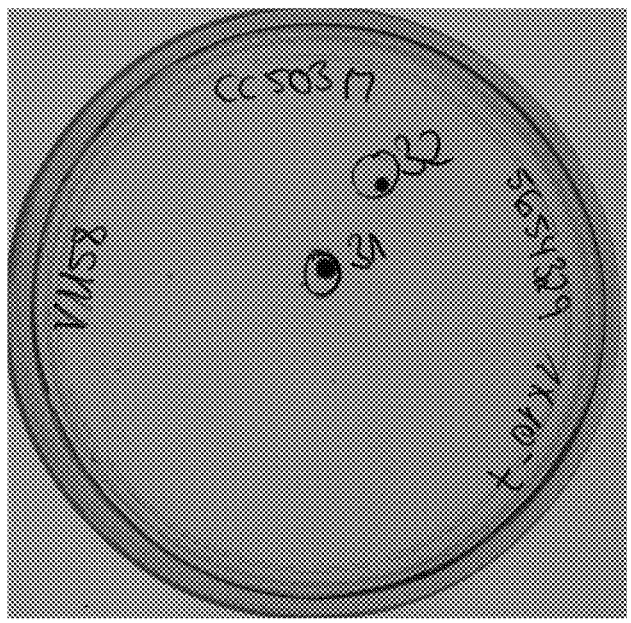
Figure 3:
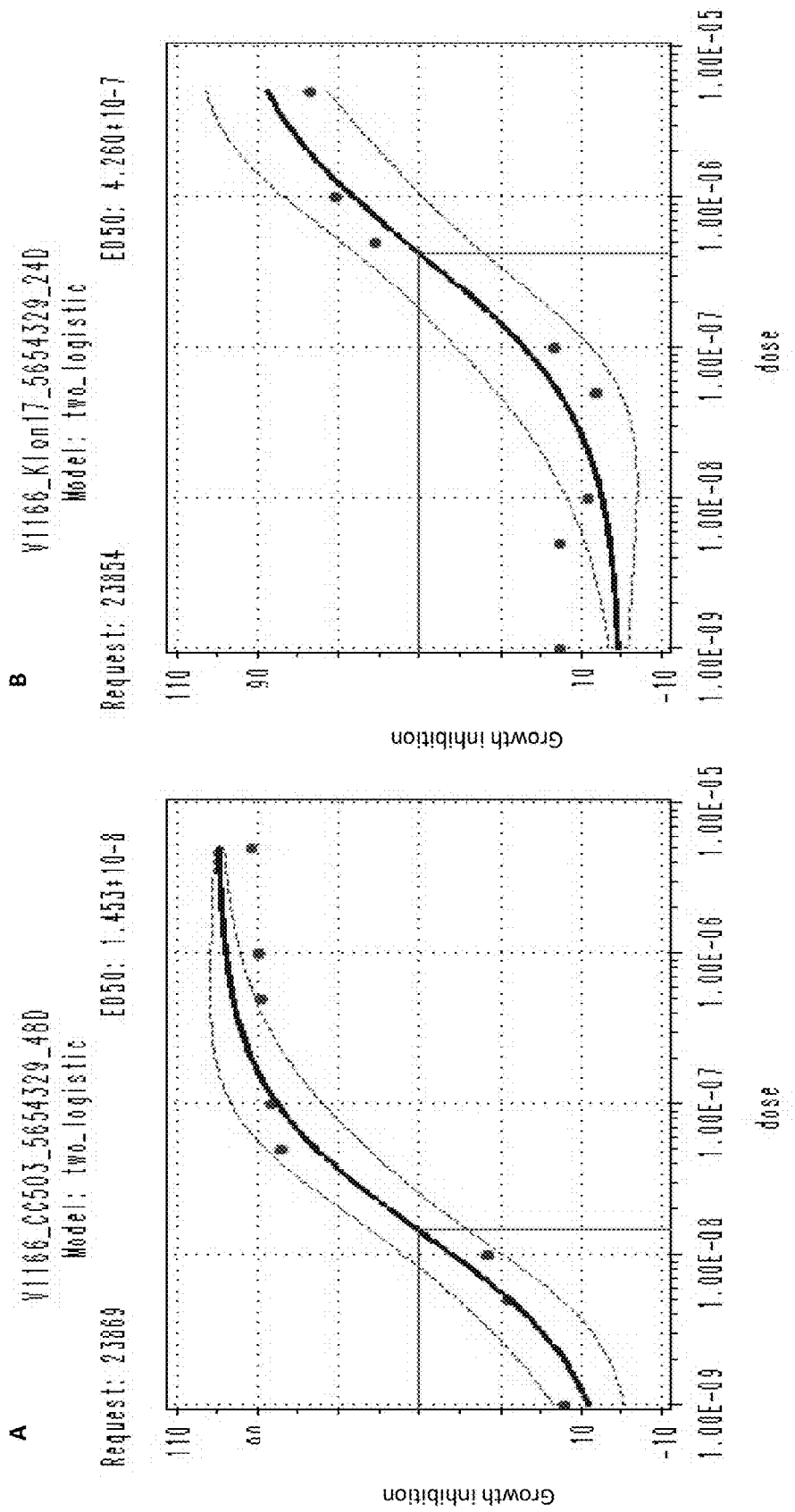
FIG. 3 shows growth-characteristics of selected *Chlamydomonas reinhardtii* strains as seen in FIG. 2, resistant to benzoxazinone-derivative 1.a.35 herbicide. (A) Dose-reponse curve of Wild-type cells treated with benzoxazinone-derivative I.a.35 with respective $IC_{50}$. (B) Dose-reponse curve of mutagenized cells (strain 17) treated with benzoxazinone-derivative I.a.35 with respective $IC_{50}$. Strain 17 (B), resistant to the benzoxazinone-derivative 1.a.35 herbicide, shows much lower $IC_{50}$, compared to Wild-type cells.

| SEQ. ID NO: | Description | Organism | Gene | Accession No: |
|---|---|---|---|---|
| 1 | PPO nucleic acid | *Amaranthus* | PPX2L_WC | DQ386114 |
| 2 | PPO amino acid | *Amaranthus* |  | ABD52326 |
| 3 | PPO nucleic acid | *Amaranthus* | PPX2L_AC | DQ386117 |
| 4 | PPO amino acid | *Amaranthus* |  | ABD52329 |
| 5 | PPO nucleic acid | *Amaranthus* | PPX2L_CC_R | DQ386118 |
| 6 | PPO amino acid | *Amaranthus* |  | ABD52330 |
| 7 | PPO nucleic acid | *Amaranthus* | PPX2L_AC_R | DQ386116 |
| 8 | PPO amino acid | *Amaranthus* |  | ABD52328 |
| 9 | PPO nucleic acid | *Arabidopsis* | PPX | AB007650 |
| 10 | PPO amino acid | *Arabidopsis* |  | BAB08301 |
| 11 | PPO nucleic acid | *Nicotiana* | ppxI | AF044128 |
| 12 | PPO amino acid | *Nicotiana* |  | AAD02290 |
| 13 | PPO nucleic acid | *Cichorium* | PPX1 | AF160961 |
| 14 | PPO amino acid | *Cichorium* |  | AF160961_1 |
| 15 | PPO nucleic acid | *Spinacia* | SO-POX1 | AB029492 |
| 16 | PPO amino acid | *Spinacia* |  | BAA96808 |
| 17 | PPO nucleic acid | *Spinacia* | SO-POX2 | AB046993 |
| 18 | PPO amino acid | *Spinacia* |  | BAB60710 |
| 19 | PPO nucleic acid | *Solanum* | PPOX | AJ225107 |
| 20 | PPO amino acid | *Solanum* |  | CAA12400 |
| 21 | PPO nucleic acid | *Zea* | AF218052 | AF218052 |
| 22 | PPO amino acid | *Zea* | AF218052 | AAF26417 |
| 23 | PPO nucleic acid | *Zea* | prpo2 | NM_001111534 |
| 24 | PPO amino acid | *Zea* |  | NP_001105004 |
| 25 | PPO nucleic acid | *Chlamydomonas* | Ppx1 | AF068635 |
| 26 | PPO amino acid | *Chlamydomonas* |  | AAC79685 |
| 27 | PPO nucleic acid | *Polytomella* | PPO | AF332964 |
| 28 | PPO amino acid | *Polytomella* |  | AF332964_1 |
| 29 | PPO nucleic acid | *Sorghum* | Hyp. Protein | XM_002446665 |
| 30 | PPO amino acid | *Sorghum* |  | XP_002446710 |
| 31 | PPO nucleic acid | *Chlorella* |  |  |
| 32 | PPO amino acid | *Chlorella* |  | 51538 |
| 33 | PPO nucleic acid | *Oryza* | PPOX1 | AB057771 |
| 34 | PPO amino acid | *Oryza* |  | BAB39760 |
| 35 | PPO nucleic acid | *Amaranthus* | PPX2 | DQ386113 |
| 36 | PPO amino acid | *Amaranthus* |  | ABD52325 |
| 37 | PPO nucleic acid | *Arabidopsis* | PPOX | NM_178952 |
| 38 | PPO amino acid | *Arabidopsis* |  | NP_849283 |
| 39 | PPO nucleic acid | *Nicotiana* | ppxII | AF044129 |

TABLE 1-continued

| SEQ. ID NO: | Description | Organism | Gene | Accession No: |
|---|---|---|---|---|
| 40 | PPO amino acid | Nicotiana | | AAD02291 |
| 41 | PPO nucleic acid | Glycine | hemG | AB025102 |
| 42 | PPO amino acid | Glycine | | BAA76348 |
| 43 | PPO nucleic acid | Cucumis | CsPPO | AB512426 |
| 44 | PPO amino acid | Cucumis | | BAH84864.1 |
| 45 | PPO nucleic acid | Oryza | Hyp. Protein | AL606613 |
| 46 | PPO amino acid | Oryza | | CAE01661 |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The present invention refers to a method for controlling undesired vegetation at a plant cultivation site, the method comprising the steps of:
a) providing, at said site, a plant that comprises at least one nucleic acid comprising a nucleotide sequence encoding a wild-type protoporphyrinogen oxidase or a mutated protoporphyrinogen oxidase (mut-PPO) which is resistant or tolerant to a benzoxazinone-derivative herbicide,
b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine* max, *Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum,*

*Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

In a preferred embodiment, the plant has been previously produced by a process comprising recombinantly preparing a plant by introducing and over-expressing a wild-type or mut-PPO transgene, as described in greater detail hereinfter.

In another preferred embodiment, the plant has been previously produced by a process comprising in situ mutagenizing plant cells, to obtain plant cells which express a mut-PPO.

As disclosed herein, the nucleic acids of the invention find use in enhancing the herbicide tolerance of plants that comprise in their genomes a gene encoding a herbicide-tolerant wild-type or mut-PPO protein. Such a gene may be an endogenous gene or a transgene, as described hereinafter. Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48:109). The combinations generated can also include multiple copies of any one of the polynucleotides of interest.

In a particularly preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyl-transferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD) and dicamba degrading enzymes as disclosed in WO 02/068607, or phenoxyaceticacid- and phenoxypropionicacid-derivative degrading enzymes as disclosed in WO 2008141154 or WO 2005107437.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by benzoxazinone-derivative herbicide of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the benzoxazinone-derivative herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant mut-PPO protein" or "herbicide-resistant mut-PPO protein", it is intended that such a mut-PPO protein displays higher PPO activity, relative to the PPO activity of a wild-type mut-PPO protein, when in the presence of at least one herbicide that is known to interfere with PPO activity and at a concentration or level of the herbicide that is known to inhibit the PPO activity of the wild-type mut-PPO protein. Furthermore, the PPO activity of such a herbicide-tolerant or herbicide-resistant mut-PPO protein may be referred to herein as "herbicide-tolerant" or "herbicide-resistant" PPO activity.

The "benzoxazinone-derivative herbicide" that are useful to carry out the present invention encompasses the benzoxazinones of formula I as depicted in the following:

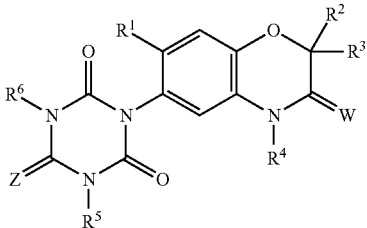

wherein
R¹ is hydrogen or halogen;
R² is halogen;
R³ is hydrogen or halogen;
R⁴ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
R⁵ is hydrogen, $NH_2$, $C_1$-$C_6$-alkyl or $C_3$-$C_6$-alkynyl;
R⁶ is hydrogen or $C_1$-$C_6$-alkyl; and
W is O or S;
Z is O or S.

In another preferred embodiment, the "benzoxazinone-derivative herbicide" that are useful to carry out the present invention encompasses the benzoxazinones of formula I as depicted in the following:
A) at least one benzoxazinone of the formula I

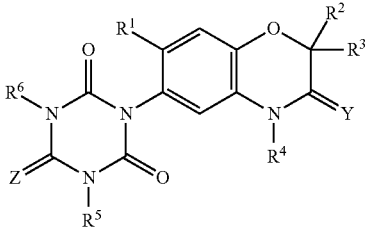

wherein
is hydrogen or halogen;
R² is halogen;
R³ is hydrogen or halogen;
R⁴ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
R⁵ is hydrogen, $NH_2$, $C_1$-$C_6$-alkyl or $C_3$-$C_6$-alkynyl;
R⁶ is hydrogen or $C_1$-$C_6$-alkyl; and
X is O or S;
Y is O or S;
and at least one further active compound selected from
B) herbicides of class b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors,
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitose inhibitors;
  b10) inhibitors of the synthesis of very long chain fatty acids (VLCFA inhibitors);
  b11) cellulose biosynthesis inhibitors;
  b12) decoupler herbicides;
  b13) auxin herbicides;
  b14) auxin transport inhibitors; and
  b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
and
C) safeners.

The benzoxazinone-derivative herbicide that are useful for the present invention can also be compositions in the form of herbicidally active crop protection compositions comprising a herbicidally effective amount of an active compound combination comprising at least one benzoxazinone of formula I and at least one further compound selected from the herbicides B and the safeners C, as defined above, and also at least one liquid and/or solid carrier and/or one or more surfactants and, if desired, one or more further auxiliaries customary for crop protection compositions.

Further, benzoxazinone-derivative herbicide that are useful for the present invention can also be compositions in the form of a crop protection composition formulated as a 1-component composition comprising an active compound combination comprising at least one benzoxazinone of formula I and at least one further active compound selected from the herbicides B and the safeners C, and at least one solid or liquid carrier and/or one or more surfactants and, if desired, one or more further auxiliaries customary for crop protection compositions.

Further, benzoxazinone-derivative herbicide that are useful for the present invention can also be compositions in the form of a crop protection composition formulated as a 2-component composition comprising a first component comprising at least one benzoxazinone of formula I, a solid or liquid carrier and/or one or more surfactants, and a second component comprising at least one further active compound selected from the herbicides B and safeners C, a solid or liquid carrier and/or one or more surfactants, where additionally both components may also comprise further auxiliaries customary for crop protection compositions.

If the benzoxazinones of formula I as described herein are capable of forming geometrical isomers, for example E/Z isomers, it is possible to use both, the pure isomers and mixtures thereof, in the compositions according to the invention.

If the benzoxazinones of formula I as described herein have one or more centers of chirality and, as a consequence, are present as enantiomers or diastereomers, it is possible to use both, the pure enantiomers and diastereomers and their mixtures, in the compositions according to the invention.

The organic moieties mentioned in the definition of the variables R¹ to R⁶, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxycarbonyl-$C_1$-$C_4$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

According to a preferred embodiment of the invention preference is also given to those benzoxazinone-derivative of formula I, wherein the variables, either independently of one another or in combination with one another, have the following meanings:

$R^1$ is hydrogen;
  is also preferably halogen, particularly preferred F or Cl, especially preferred F;
$R^2$ is F;
$R^3$ is hydrogen or F, preferably hydrogen;
  is also preferably F;
$R^4$ is $C_3$-$C_6$-alkynyl or $C_3$-$C_6$-halolkynyl, preferably $C_3$-alkynyl or $C_3$-halolkynyl, particularly preferred $CH_2C\equiv CH$, $CH_2C\equiv CCl$ or $CH_2C\equiv CBr$;
  is also preferably $C_3$-$C_6$-alkynyl or $C_3$-$C_6$-cycloalkyl-$C_1$-$C_6$-alkyl, particularly preferred propargyl or cyclopropylmethyl;
  is also preferably $C_3$-$C_6$-alkynyl, preferably $C_3$-alkynyl; particularly preferred $CH_2C\equiv CH$;
  is also preferably $C_3$-$C_6$-halolkynyl, preferably $C_3$-halolkynyl, particularly preferred $CH_2C\equiv CCl$ or $CH_2C\equiv CBr$;
$R^5$ is $NH_2$, $C_1$-$C_6$-Alkyl or $C_3$-$C_6$-alkynyl; preferably $C_1$-$C_6$-alkyl; more preferably $C_1$-$C_4$-alkyl; most preferably $CH_3$;
$R^6$ is $C_1$-$C_6$-alkyl; preferably $C_1$-$C_4$-alkyl; most preferably $CH_3$;
W is O,
  is also preferably S;
Z is O,
  is also preferably S.

Particular preference is given to benzoxazinones of the formula I.a (corresponds to formula I wherein $R^2$ is F, $R^5$ and $R^6$ are $CH_3$, W is O and Z is S),

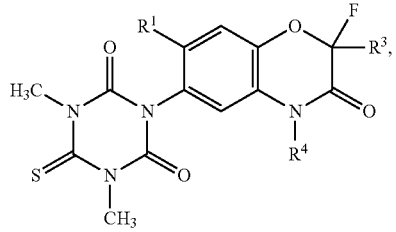

I.a wherein the variables $R^1$, $R^3$, and $R^4$ have the meanings, in particular the preferred meanings, as defined above.

Most preference to the benzoxazinone-derivatives of the formulae I.a.1 to I.a.48 of Table A listed below, in which the variables $R^1$, $R^3$ and $R^4$ together have the meanings given in one row of Table A (benzoxazinones I.a.1 to I.a.54); and where the definitions of the variables $R^1$, $R^2$, $R^3$ and $R^4$ are of particular importance for the compounds according to the invention not only in combination with one another but in each case also on their own.

TABLE A

| No. | $R^1$ | $R^3$ | $R^4$ |
|---|---|---|---|
| I.a.1. | H | H | H |
| I.a.2. | H | H | $CH_3$ |
| I.a.3. | H | H | $C_2H_5$ |
| I.a.4. | H | H | $CH_2$—$C_2H_5$ |
| I.a.5. | H | H | $CH(CH_3)_2$ |
| I.a.6. | H | H | $CH_2$—$CH_2$—$(CH_3)_2$ |
| I.a.7. | H | H | $CH_2$—$CH=CH_2$ |

TABLE A-continued

| No. | $R^1$ | $R^3$ | $R^4$ |
|---|---|---|---|
| I.a.8. | H | H | $CH_2C\equiv CH$ |
| I.a.9. | H | H | $CH_2C\equiv C$—Br |
| I.a.10. | H | F | H |
| I.a.11. | H | F | $CH_3$ |
| I.a.12. | H | F | $C_2H_5$ |
| I.a.13. | H | F | $CH_2$—$C_2H_5$ |
| I.a.14. | H | F | $CH(CH_3)_2$ |
| I.a.15. | H | F | $CH_2$—$CH_2$—$(CH_3)_2$ |
| I.a.16. | H | F | $CH_2$—$CH=CH_2$ |
| I.a.17. | H | F | $CH_2C\equiv CH$ |
| I.a.18. | H | F | $CH_2C\equiv C$—Br |
| I.a.19. | F | H | H |
| I.a.20. | F | H | $CH_3$ |
| I.a.21. | F | H | $C_2H_5$ |
| I.a.22. | F | H | $CH_2$—$C_2H_5$ |
| I.a.23. | F | H | $CH(CH_3)_2$ |
| I.a.24. | F | H | $CH_2$—$CH_2$—$(CH_3)_2$ |
| I.a.25. | F | H | $CH_2$—$CH=CH_2$ |
| I.a.26. | F | H | $CH_2C\equiv CH$ |
| I.a.27. | F | H | $CH_2C\equiv C$—Br |
| I.a.28. | F | F | H |
| I.a.29. | F | F | $CH_3$ |
| I.a.30. | F | F | $C_2H_5$ |
| I.a.31. | F | F | $CH_2$—$C_2H_5$ |
| I.a.32. | F | F | $CH(CH_3)_2$ |
| I.a.33. | F | F | $CH_2$—$CH_2$—$(CH_3)_2$ |
| I.a.34. | F | F | $CH_2$—$CH=CH_2$ |
| I.a.35. | F | F | $CH_2C\equiv CH$ |
| I.a.36. | F | F | $CH_2C\equiv C$—Br |
| I.a.37. | Cl | H | H |
| I.a.38. | Cl | H | $CH_3$ |
| I.a.39. | Cl | H | $C_2H_5$ |
| I.a.40. | Cl | H | $CH_2$—$C_2H_5$ |
| I.a.41. | Cl | H | $CH(CH_3)_2$ |
| I.a.42. | Cl | H | $CH_2$—$CH_2$—$(CH_3)_2$ |
| I.a.43. | Cl | H | $CH_2$—$CH=CH_2$ |
| I.a.44. | Cl | H | $CH_2C\equiv CH$ |
| I.a.45. | Cl | H | $CH_2C\equiv C$—Br |
| I.a.46. | Cl | F | H |
| I.a.47. | Cl | F | $CH_3$ |
| I.a.48. | Cl | F | $C_2H_5$ |
| I.a.49. | Cl | F | $CH_2$—$C_2H_5$ |
| I.a.50. | Cl | F | $CH(CH_3)_2$ |
| I.a.51. | Cl | F | $CH_2$—$CH_2$—$(CH_3)_2$ |
| I.a.52. | Cl | F | $CH_2$—$CH=CH_2$ |
| I.a.53. | Cl | F | $CH_2C\equiv CH$ |
| I.a.54. | Cl | F | $CH_2C\equiv C$—Br |

An especially preferred benzoxazinone of the formula I which, as component A, is part of the composition according to the invention, is the benzoxazinone of formula I.a.35 as defined above According to a particular preferred embodiment of the invention the composition useful for the method of the present invention contains as component A the benzoxazinone of formula I.a.35.

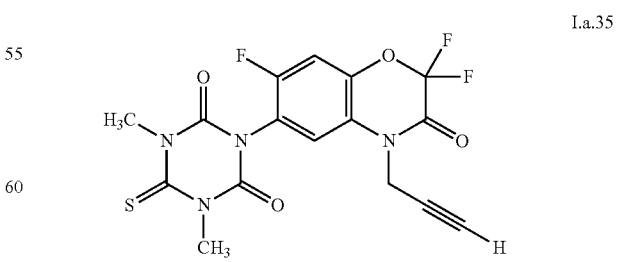

I.a.35

The above described benzoxazinone-derivatives and compositions are disclosed in detail in the European patent application 09163242.2, in particular the disclosures on pages 1 to 7 referring to the benzoxazinone-derivatives and their possible substitutents are entirely incorporated by reference.

The benzoxazinone-derivatives that are useful to carry out the present invention are often best applied in conjunction with one or more other herbicides to obtain control of a wider variety of undesirable vegetation. When used in conjunction with other targeting herbicides, the presently claimed compounds can be formulated with the other herbicide or herbicides, tank mixed with the other herbicide or herbicides, or applied sequentially with the other herbicide or herbicides.

The herbicidal compounds that are useful to carry out the present invention may further be used in conjunction with additional herbicides to which the crop plant is naturally tolerant, or to which it is resistant via expression of one or more additional transgenes as mentioned supra. Some of the herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, ima-zethapyr, imzapyr, imazamethabenz and imazamox, phenoxyalkanoic acids such as 2,4-D, MCPA, dichlorpropand mecoprop, pyridinyloxyacetic acids such as triclopyr and fluoroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxapropand other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione.

For example, the benzoxazinone-derivative herbicides that are useful to carry out the present invention can be used in conjunction with glyphosate and glufosinate on glyphosate-tolerant or glufosinate-tolerant crops.

Unless already included in the disclosure above, the benzoxazinone-derivative herbicides that are useful to carry out the present invention can, further, be used in conjunction with compounds:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propy-risulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyl-triazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridatre, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione;

b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitose inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and
isoxazoline compounds of the formula II,

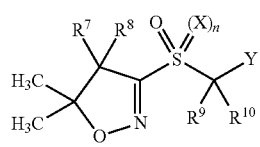

(II)

wherein $R^7$, $R^8$, $R^9$, $R^{10}$, W, Z and n have the following meanings:

$R^7$, $R^8$, $R^9$, $R^{10}$ independently of one another hydrogen, halogen or $C_1$-$C_4$-alkyl;

X oxygen or NH;

Y phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;

preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$; and n zero or one;

among the isoxazoline compounds of the formula II, preference is given to isoxazoline compounds of the formula II, wherein $R^7$, $R^8$, $R^9$, $R^{10}$ independently of one another are H, F, Cl or methyl;

X is oxygen;

n is 0 or 1; and

Y is phenyl, pyrazolyl or 1,2,3-triazolyl, wherein the three last-mentioned radicals are unsubstituted or carry one, two or three substituents $R^{yy}$, especially one of the following radicals

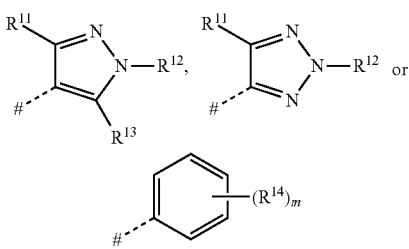

wherein $R^{11}$ is halogen, $C_1$-$C_4$-alkyl or $C_1$-$C_4$-haloalkyl;

$R^{12}$ is $C_1$-$C_4$-alkyl;

$R^{13}$ is halogen, $C_1$-$C_4$-alkoxy or $C_1$-$C_4$-haloalkoxy;

$R^{14}$ is halogen, $C_1$-$C_4$-alkyl, $C_1$-$C_4$-haloalkyl or $C_1$-$C_4$-haloalkoxy;

m is 0, 1, 2 or 3; and # denotes the point of attachment to the group $CR^{13}R^{14}$;

among the isoxazoline compounds of the formula II, particular preference is given to those isoxazoline compounds of the formula II, wherein $R^7$ is hydrogen;

$R^8$ is fluorine;

$R^9$ is hydrogen or fluorine;

$R^{10}$ is hydrogen or fluorine;
X is oxygen;
Y is one of the radicals of the formulae $Y^1$, $Y^2$, $Y^3$ or $Y^4$

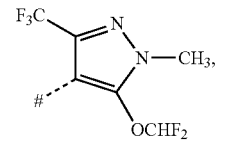
$Y^1$

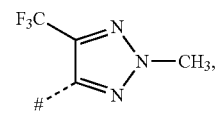
$Y^2$

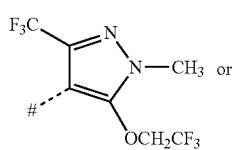
$Y^3$

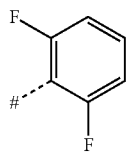
$Y^4$ wherein # denotes the point of attachment to the group $CR^9R^{10}$;
n is zero or 1, in particular 1; and
among these, especially preferred are the isoxazoline compounds of the formulae II.1, II.2, II.3, II.4, II.5, II.6, II.7, II.8 and II.9

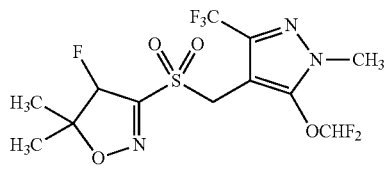
II.1

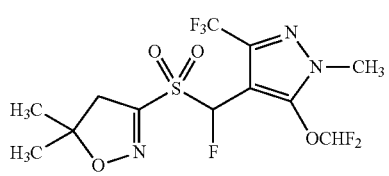
II.2

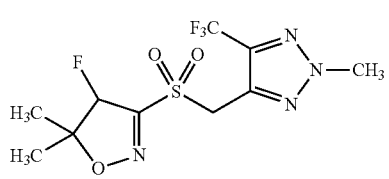
II.3

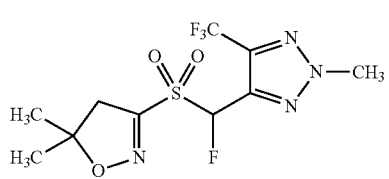
II.4

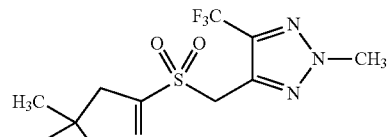
II.5

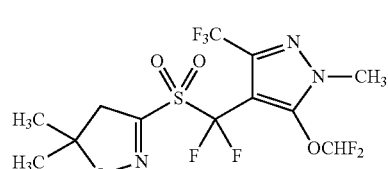
II.6

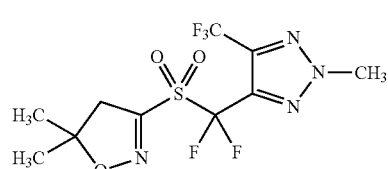
II.7

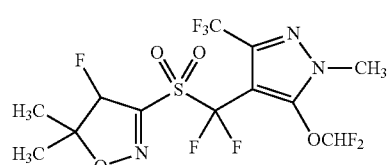
II.8

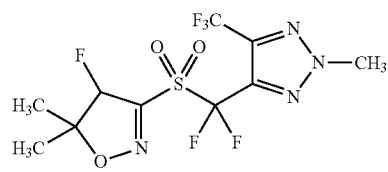
II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides, especially to pyroxasulfone;

b11) from the group of the cellulose biosynthesis inhibitors: chlorthiamid, dichlobenil, flupoxam, isoxaben, 1-Cyclohexyl-5-pentafluorphenyloxy-1⁴-[1,2,4,6]thiatriazin-3-ylamine and piperazine compounds of formula III,

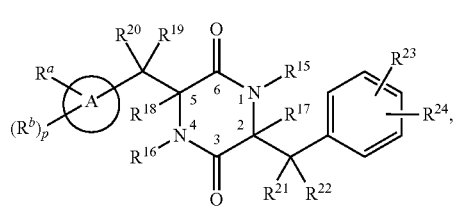
III in which
A is phenyl or pyridyl where $R^a$ is attached in the ortho-position to the point of attachment of A to a carbon atom;
$R^a$ is CN, $NO_2$, $C_1$-$C_4$-alkyl, D-$C_3$-$C_6$-cycloalkyl, $C_1$-$C_4$-haloalkyl, $C_1$-$C_4$-alkoxy, $C_1$-$C_4$-haloalkoxy, O-D-$C_3$-$C_6$-cycloalkyl, $S(O)_qR^y$, $C_2$-$C_6$-alkenyl, D-$C_3$-$C_6$-cycloalkenyl, $C_3$-$C_6$-alkenyloxy, $C_2$-$C_6$-alkynyl, $C_3$-$C_6$- alkynyloxy, $NR^AR^B$, tri-$C_1$-$C_4$-alkylsilyl, D-C(=O)—$R^{a1}$ D-P(=O)($R^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups $R^{aa}$ and/or $R^{a1}$, and, if $R^a$ is attached to a carbon atom, additionally halogen;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond, $C_1$-$C_4$-alkylene, $C_2$-$C_6$-alkenyl or $C_2$-$C_6$-alkynyl;

$R^{a1}$ is hydrogen, OH, $C_1$-$C_8$-Alkyl, $C_1$-$C_4$-haloalkyl, $C_3$-$C_6$-cycloalkyl, $C_2$-$C_8$-alkenyl, $C_5$-$C_6$-cycloalkenyl, $C_2$-$C_8$-alkynyl, $C_1$-$C_6$-alkoxy, $C_1$-$C_4$-haloalkoxy, $C_3$-$C_8$-alkenyloxy, $C_3$-$C_8$-alkynyloxy, $NR^AR^B$, $C_1$-$C_6$-alkoxyamino, $C_1$-$C_6$-alkylsulfonylamino, $C_1$-$C_6$-alkylaminosulfonylamino, [di-($C_1$-$C_6$)alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-haloalkyl, $C_1$-$C_4$-alkoxy, $C_1$-$C_4$-haloalkoxy, $S(O)_qR^y$, D-C(=O)—$R^{a1}$ and tri-$C_1$-$C_4$-alkylsilyl;

Rb independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{15}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, C(=O)$R^{25}$, CON—$R^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, C(=O)$R^{25}$, CON-$R^AR^B$;

preferably is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, C(=O)$R^{25}$, CONR$^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl and $C_3$-$C_4$-alkynyl;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl, $C_3$-$C_4$-alkenyl or $C_3$-$C_4$-alkynyl;

$R^{17}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or C(=O)$R^{25}$;

$R^{18}$ is hydrogen, halogen, $C_1$-$C_4$-alkyl or $C_1$-$C_4$-haloalkyl, or $R^{18}$ and $R^{19}$ together are a covalent bond;

$R^{19}$, $R^{20}$, $R^{21}$, $R^{21}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{23}$, $R^{24}$ independently of one another are hydrogen, halogen, OH, haloalkyl, $NR^AR^B$, $NR^AC(O)R^{26}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{26}$, phenoxy or benzyloxy, where in groups $R^{23}$ and $R^{24}$ the carbon chains and/or the cyclic groups may carry 1, 2, 3 or 4 substituents $R^{aa}$;

$R^{26}$ is $C_1$-$C_4$-alkyl or $NR^AR^B$;

among the isoxazoline compounds of the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-haloalkyl, $C_1$-$C_4$-alkoxy, $C_1$-$C_4$-haloalkoxy, $S(O)_qR^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{15}$ is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{25}$, which can be partially or fully substituted by $R^{aa}$-groups;

preferably is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{25}$;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl;

$R^{17}$ is OH, $NH_2$, $C_1$-$C_4$-alkyl, $C_3$-$C_6$-cycloalkyl, $C_1$-$C_4$-haloalkyl or $C(=O)R^{25}$;

$R^{18}$ is hydrogen, or $R^{18}$ and $R^{19}$ together are a covalent bond;

$R^{19}$, $R^{20}$, $R^{21}$, $R^{21}$ independently of one another are hydrogen;

$R^{23}$, $R^{24}$ independently of one another are hydrogen, halogen or OH;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the benzoxazinones of the formula I in combination with safeners. Safeners are chemical compounds which prevent or reduce damage on useful plants without having a major impact on the herbicidal action of the benzoxazinones of the formula I towards unwanted plants. They can be applied either before sowings (e.g. on seed treatments, shoots or seedlings) or in the pre-emergence application or post-emergence application of the useful plant.

Furthermore, the safeners C, the benzoxazinones I and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro-[4.5]decane (MON4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Particularly preferred safeners C, which, as component C, are constituent of the composition according to the invention are the safeners C as defined above; in particular the safeners C.1-C.13 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloro-acetyl)-1,3-oxazolidine (R-29148, CAS 52836-31-4) |

TABLE C-continued

Safener C

C.13 N-(2-Methoxybenzoyl)-4-[(methylaminocarbonyl)amino]
benzenesulfonamide (CAS 129531-12-0)

The active compounds B of groups b1) to b15) and the active compounds C are known herbicides and safeners, see, for example, The Compendium of Pesticide Common Names (World Wide Web at alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660. Further herbicidally active compounds are known from WO 96/26202, WO 97/41116, WO 97/41117, WO 97/41118 and WO 01/83459 and also from W. Kramer et al. (ed.) "Modern Crop Protection Compounds", Vol. 1, Wiley VCH, 2007 and the literature cited therein.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

It is recognized that the polynucleotide molecules and polypeptides of the invention encompass polynucleotide molecules and polypeptides comprising a nucleotide or an amino acid sequence that is sufficiently identical to nucleotide sequences set forth in SEQ ID Nos: 1, 3, 5, 7, 9, 11, 13, 15, 17, 19, 21, 23, 25, 27, 29, 31, 33, 35, 37, 39, 41, 43, or 45, or to the amino acid sequences set forth in SEQ ID Nos: 2, 4, 6, 8, 10, 12, 14, 16, 18, 20, 22, 24, 26, 28, 30, 32, 34, 36, 38, 40, 42, 44, or 46. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mut-PPO nucleic acid" refers to a PPO nucleic acid having a sequence that is mutated from a wild-type PPO nucleic acid and that confers increased benzoxazinone-derivative herbicide tolerance to a plant in which it is expressed. Furthermore, the term "mutated protoporphyrinogen oxidase (mut-PPO)" refers to the replacement of an amino acid of the wild-type primary sequences SEQ ID NO: 2, 4, 6, 8, 10, 12, 14, 16, 18, 20, 22, 24, 26, 28, 30, 32, 34, 36, 38, 40, 42, 44, or 46, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the PPO nucleotide sequence comprises the sequence of SEQ ID NO: 1, 25, 37 or 39 or a variant or derivative thereof.

Furthermore, it will be understood by the person skilled in the art that the PPO nucleotide sequences encompasse homologues, paralogues and orthologues of SEQ ID NO: 1, 25, 37 or 39 as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: SEQ ID NO: 1, 3, 5, 7, 9, 11, 13, 15, 17, 19, 21, 23, 25, 27, 29, 31, 33, 35, 37, 39, 41, 43, or 45. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 2, 4, 6, 8, 10, 12, 14, 16, 18, 20, 22, 24, 26, 28, 30, 32, 34, 36, 38, 40, 42, 44, or 46.

By "variant" polypeptide is intended a polypeptide derived from the protein of SEQ ID NO: 2, 4, 6, 8, 10, 12, 14, 16, 18, 20, 22, 24, 26, 28, 30, 32, 34, 36, 38, 40, 42, 44, or 46 by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intrasequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 2

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues are shown in Table 1.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have found that by substituting one or more of the key amino acid residues the herbicide tolerance or resistance could be remarkably increased as compared to the activity of the wild type PPO enzymes with SEQ ID NO: 2, 4, 6, 8, 10, 12, 14, 16, 18, 20, 22, 24, 26, 28, 30, 32, 34, 36, 38, 40, 42, 44, or 46. Preferred substitutions of mut-PPO are those that increase the herbicide tolerance of the plant, but leave the biological activity of the oxidase activity substantially unaffected.

Accordingly, in another object of the present invention the key amino acid residues of a PPO enzyme, a variant, derivative, orthologue, paralogue or homologue thereof, is substituted by any other amino acid.

In a preferred embodiment, the key amino acid residues of a PPO enzyme, a variant, derivative, orthologue, paralogue or homologue thereof, is substituted by a conserved amino acid as depicted in Table 2.

It will be understood by the person skilled in the art that amino acids located in a close proximity to the positions of amino acids mentioned below may also be substituted. Thus, in another embodiment the variant of SEQ ID NO: 2, 4, 6, 8, 10, 12, 14, 16, 18, 20, 22, 24, 26, 28, 30, 32, 34, 36, 38, 40, 42, 44, or 46, a variant, derivative, orthologue, paralogue or homologue thereof comprises a mut-PPO, wherein an amino acid ±3, ±2 or ±1 amino acid positions from a key amino acid is substituted by any other amino acid.

Based on techniques well-known in the art, a highly characteristic sequence pattern can be developed, by means of which further of mut-PPO candidates with the desired activity may be searched.

Searching for further mut-PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, the inventors of the present invention have identified specific combinations of mutations, which combination refers to a substitution of the Phenylalanine residue at position 420 in SEQ ID NO:2 or 4, combined with a second substitution of the Leucin at position 397 in SEQ ID NO:2 or 4.

Thus, in a particularly preferred embodiment, the variant or derivative of the mut-PPO of SEQ ID NO: 2 or SEQ ID NO: 4 is selected from the combined amino acid substitutions of the following Table 3a.

TABLE 3a

SEQ ID NO: 2 or SEQ ID NO: 4 (combined amino acid substitutions obtained by site directed mutagenesis.)

| Combination Number | SEQ ID NO: | Key amino acid position combination | Preferred Substitution |
|---|---|---|---|
| 1 | 2 or 4 | Leu397 | Gly |
|  |  | Phe420 | Met |
| 2 | 2 or 4 | Leu397 | Ala |
|  |  | Phe420 | Met |
| 3 | 2 or 4 | Leu397 | Ser |
|  |  | Phe420 | Met |
| 4 | 2 or 4 | Leu397 | Thr |
|  |  | Phe420 | Met |
| 5 | 2 or 4 | Leu397 | Cys |
|  |  | Phe420 | Met |
| 6 | 2 or 4 | Leu397 | Val |
|  |  | Phe420 | Met |
| 7 | 2 or 4 | Leu397 | Ile |
|  |  | Phe420 | Met |
| 8 | 2 or 4 | Leu397 | Met |
|  |  | Phe420 | Met |
| 9 | 2 or 4 | Leu397 | Pro |
|  |  | Phe420 | Met |
| 10 | 2 or 4 | Leu397 | Phe |
|  |  | Phe420 | Met |
| 11 | 2 or 4 | Leu397 | Tyr |
|  |  | Phe420 | Met |
| 12 | 2 or 4 | Leu397 | Trp |
|  |  | Phe420 | Met |
| 13 | 2 or 4 | Leu397 | Asp |
|  |  | Phe420 | Met |
| 14 | 2 or 4 | Leu397 | Glu |
|  |  | Phe420 | Met |
| 15 | 2 or 4 | Leu397 | Asn |
|  |  | Phe420 | Met |
| 16 | 2 or 4 | Leu397 | Gln |
|  |  | Phe420 | Met |
| 17 | 2 or 4 | Leu397 | His |
|  |  | Phe420 | Met |
| 18 | 2 or 4 | Leu397 | Lys |
|  |  | Phe420 | Met |
| 19 | 2 or 4 | Leu397 | Arg |
|  |  | Phe420 | Met |
| 20 | 2 or 4 | Leu397 | Gly |
|  |  | Phe420 | Val |
| 21 | 2 or 4 | Leu397 | Ala |
|  |  | Phe420 | Val |
| 22 | 2 or 4 | Leu397 | Ser |
|  |  | Phe420 | Val |
| 23 | 2 or 4 | Leu397 | Thr |
|  |  | Phe420 | Val |
| 24 | 2 or 4 | Leu397 | Cys |
|  |  | Phe420 | Val |
| 25 | 2 or 4 | Leu397 | Val |
|  |  | Phe420 | Val |
| 26 | 2 or 4 | Leu397 | Ile |
|  |  | Phe420 | Val |
| 27 | 2 or 4 | Leu397 | Met |
|  |  | Phe420 | Val |
| 28 | 2 or 4 | Leu397 | Pro |
|  |  | Phe420 | Val |
| 29 | 2 or 4 | Leu397 | Phe |
|  |  | Phe420 | Val |
| 30 | 2 or 4 | Leu397 | Tyr |
|  |  | Phe420 | Val |
| 31 | 2 or 4 | Leu397 | Trp |
|  |  | Phe420 | Val |
| 32 | 2 or 4 | Leu397 | Asp |
|  |  | Phe420 | Val |
| 33 | 2 or 4 | Leu397 | Glu |
|  |  | Phe420 | Val |
| 34 | 2 or 4 | Leu397 | Asn |
|  |  | Phe420 | Val |
| 35 | 2 or 4 | Leu397 | Gln |
|  |  | Phe420 | Val |
| 36 | 2 or 4 | Leu397 | His |
|  |  | Phe420 | Val |
| 37 | 2 or 4 | Leu397 | Lys |
|  |  | Phe420 | Val |
| 38 | 2 or 4 | Leu397 | Arg |
|  |  | Phe420 | Val |

In a further particularly preferred embodiment, the variant or derivative of the mut-PPO of SEQ ID NO: 2 or SEQ ID NO: 4 is selected from the combined amino acid substitutions of the following Table 3b.

TABLE 3b

SEQ ID NO: 2 or SEQ ID NO: 4
(combined amino acid substitutions)

| Combination Number | SEQ ID NO: | Key amino acid position combination | Preferred Substitution |
|---|---|---|---|
| 39 | 2 or 4 | Leu397 | Asp, Glu, Gln, Asn |
|  |  | Leu400 | Ala, Ile, Val, Met |
| 40 | 2 or 4 | Leu397 | Asp, Glu, Gln, Asn |
|  |  | Phe457 | Met, Ala, Leu, Ile, Val |
| 41 | 2 or 4 | Phe204 | Ala, Leu, Ile, Val |
|  |  | Leu397 | Asp, Glu, Gln, Asn |
| 42 | 2 or 4 | Thr208 | Ser |
|  |  | Leu400 | Ala, Ile, Val, Met |
| 43 | 2 or 4 | Leu400 | Ala |
|  |  | Phe457 | Met, Ala, Leu, Ile, Val |
| 44 | 2 or 4 | Phe204 | Ile |
|  |  | Leu400 | Ala, Ile, Val, Met |
| 45 | 2 or 4 | The208 | Ser |
|  |  | Phe457 | Met, Ala, Leu, Ile, Val |
| 46 | 2 or 4 | Phe204 | Ile |
|  |  | Thr208 | Ser |
| 47 | 2 or 4 | Phe204 | Ile |
|  |  | Phe457 | Met, Ala, Leu, Ile, Val |
| 48 | 2 or 4 | Leu400 | Ala, Ile, Val, Met |
|  |  | Phe420 | Val, Met, Ala, Ile, Leu |
| 49 | 2 or 4 | Phe204 | Ile |
|  |  | Phe420 | Val, Met, Ala, Ile, Leu |
| 50 | 2 or 4 | Phe420 | Val, Met, Ala, Ile, Leu |
|  |  | Phe457 | Met, Ala, Leu, Ile, Val |
| 51 | 2 or 4 | Arg128 | Ala, Leu, Ile, Val |
|  |  | Leu397 | Asp, Glu, Gln, Asn |
| 52 | 2 or 4 | Thr208 | Ser |
|  |  | Leu397 | Asp, Glu, Gln, Asn |
|  |  | Phe457 | Met, Ala, Leu, Ile, Val |
| 53 | 2 or 4 | Phe204 | Ile |
|  |  | The208 | Ser |
|  |  | Leu397 | Asp, Glu, Gln, Asn |
| 54 | 2 or 4 | Phe204 | Ile |
|  |  | Leu397 | Asp, Glu, Gln, Asn |
|  |  | Phe457 | Met, Ala, Leu, Ile, Val |
| 55 | 2 or 4 | Thr208 | Ser |
|  |  | Leu400 | Ala, Ile, Val, Met |
|  |  | Phe457 | Met, Ala, Leu, Ile, Val |
| 56 | 2 or 4 | Phe204 | Ile |
|  |  | Thr208 | Ser |
|  |  | Leu400 | Ala, Ile, Val, Met |
| 57 | 2 or 4 | Phe204 | Ile |
|  |  | Leu400 | Ala, Ile, Val, Met |
|  |  | Phe457 | Met, Ala, Leu, Ile, Val |
| 58 | 2 or 4 | Thr208 | Ser |
|  |  | Leu397 | Asp, Glu, Gln, Asn |
|  |  | Leu400 | Ala, Ile, Val, Met |
| 59 | 2 or 4 | Leu397 | Asp, Glu, Gln, Asn |
|  |  | Leu400 | Ala, Ile, Val, Met |
|  |  | Phe457 | Met, Ala, Leu, Ile, Val |
| 60 | 2 or 4 | Phe204 | Ile |
|  |  | Leu397 | Asp, Glu, Gln, Asn |
|  |  | Leu400 | Ala, Ile, Val, Met |
| 61 | 2 or 4 | Phe204 | Ile |
|  |  | Thr208 | Ser |
|  |  | Phe457 | Met, Ala, Leu, Ile, Val |
| 62 | 2 or 4 | Leu397 | Asp, Glu, Gln, Asn |
|  |  | Leu400 | Ala, Ile, Val, Met |
|  |  | Phe420 | Met, Ala, Leu, Ile, Val |
| 63 | 2 or 4 | Leu397 | Asp, Glu, Gln, Asn |
|  |  | Phe420 | Met, Ala, Leu, Ile, Val |
|  |  | Phe457 | Met, Ala, Leu, Ile, Val |
| 64 | 2 or 4 | Phe204 | Ile |
|  |  | Leu397 | Asp, Glu, Gln, Asn |
|  |  | Phe420 | Met, Ala, Leu, Ile, Val |
| 65 | 2 or 4 | Phe204 | Ile |
|  |  | Thr208 | Ser |
|  |  | Phe420 | Met, Ala, Leu, Ile, Val |
| 66 | 2 or 4 | Thr208 | Ser |
|  |  | Phe420 | Met, Ala, Leu, Ile, Val |
|  |  | Phe457 | Met, Ala, Leu, Ile, Val |
| 67 | 2 or 4 | Phe204 | Ile |
|  |  | Phe420 | Met, Ala, Leu, Ile, Val |
|  |  | Phe457 | Met, Ala, Leu, Ile, Val |
| 68 | 2 or 4 | Arg128 | Ala, Leu, Ile, Val |
|  |  | Leu400 | Ala, Ile, Val, Met |
|  |  | Phe420 | Met, Ala, Leu, Ile, Val |
| 69 | 2 or 4 | Arg128 | Ala, Leu, Ile, Val |
|  |  | Leu397 | Asp, Glu, Gln, Asn |
|  |  | Phe420 | Met, Ala, Leu, Ile, Val |
| 70 | 2 or 4 | Arg128 | Ala, Leu, Ile, Val |
|  |  | Phe204 | Ile |
|  |  | Phe420 | Met, Ala, Leu, Ile, Val |
| 71 | 2 or 4 | Arg128 | Ala, Leu, Ile, Val |
|  |  | Phe420 | Met, Ala, Leu, Ile, Val |
|  |  | Phe457 | Met, Ala, Leu, Ile, Val |
| 72 | 2 or 4 | Thr208 | Ser |
|  |  | Leu400 | Ala, Ile, Val, Met |
|  |  | Phe420 | Met, Ala, Leu, Ile, Val |
| 73 | 2 or 4 | Leu400 | Ala, Ile, Val, Met |
|  |  | Phe420 | Met, Ala, Leu, Ile, Val |
|  |  | Phe457 | Met, Ala, Leu, Ile, Val |
| 74 | 2 or 4 | Phe204 | Ile |
|  |  | Leu400 | Ala, Ile, Val, Met |
|  |  | Phe420 | Met, Ala, Leu, Ile, Val |
| 75 | 2 or 4 | Phe204 | Ile |
|  |  | Thr208 | Ser |
|  |  | Leu400 | Ala, Ile, Val, Met |
|  |  | Phe457 | Met, Ala, Leu, Ile, Val |
| 76 | 2 or 4 | Phe204 | Ile |
|  |  | Thr208 | Ser |
|  |  | Phe420 | Met, Ala, Leu, Ile, Val |
|  |  | Phe457 | Met, Ala, Leu, Ile, Val |
| 77 | 2 or 4 | Arg128 | Ala, Leu, Ile, Val |
|  |  | Phe204 | Ile |
|  |  | Phe420 | Met, Ala, Leu, Ile, Val |
|  |  | Phe457 | Met, Ala, Leu, Ile, Val |
| 78 | 2 or 4 | Phe204 | Ile |
|  |  | Leu400 | Ala, Ile, Val, Met |
|  |  | Phe420 | Met, Ala, Leu, Ile, Val |
|  |  | Phe457 | Met, Ala, Leu, Ile, Val |
| 79 | 2 or 4 | Phe204 | Ile |
|  |  | Thr208 | Ser |
|  |  | Leu397 | Asp, Glu, Gln, Asn |
|  |  | Leu400 | Ala, Ile, Val, Met |
| 80 | 2 or 4 | Phe204 | Ile |
|  |  | Thr208 | Ser |
|  |  | Leu400 | Ala, Ile, Val, Met |
|  |  | Phe420 | Met, Ala, Leu, Ile, Val |
|  |  | Phe457 | Met, Ala, Leu, Ile, Val |
| 81 | 2 or 4 | Arg128 | Ala, Leu, Ile, Val |
|  |  | Phe204 | Ile |
|  |  | Leu400 | Ala, Ile, Val, Met |
|  |  | Phe420 | Met, Ala, Leu, Ile, Val |
|  |  | Phe457 | Met, Ala, Leu, Ile, Val |

It is to be understood that any amino acid besides the ones mentioned in the above tables 3 could be used as a substitutent. Assays to test for the functionality of such mutants are readily available in the art, and respectively, described in the Example section of the present invention.

In a preferred embodiment, the amino acid sequence differs from an amino acid sequence of a PPO of SEQ ID NO: 2 or SEQ ID NO: 4 at one or more of the following positions: 128, 204, 208, 397, 400, 420, 457.

Examples of differences at these amino acid positions include, but are not limited to, one or more of the following:
the amino acid at position 128 is other than Arginine;
the amino acid at position 204 is other than Phenylalanine;
the amino acid at position 208 is other than Threonine;
the amino acid at position 397 is other than Leucine,
the amino acid at position 400 is other than Leucine,
the amino acid at position 420 is other than Phenylalanine,
the amino acid at position 457 is other than Phenylalanine.

In some embodiments, the mut-PPO enzyme of SEQ ID NO: 2 or SEQ ID NO: 4 comprises one or more of the following:
the amino acid at position 128 is Leu, Ala, Val, or Ile;
the amino acid at position 204 is Ala, Leu, Ile, or Val;
the amino acid at position 208 is Ser;
the amino acid at position 397 is Gly, Ala, Ser, Thr, Cys, Val, Ile, Met, Pro, Phe, Tyr, Trp, His, Lys, Arg, Asn, Asp, Glu, or Gln;
the amino acid at position 400 is Ala, Ile, Val, or Met;
the amino acid at position 420 is Val, Met, Ala, Ile, or Leu;
the amino acid at position 457 is Met, Ala, Leu, Ile, Val;

In a preferred embodiment, the mut-PPO comprises a sequence of SEQ ID NO: 2 or SEQ ID NO:4, a variant, derivative, orthologue, paralogue or homologue thereof, in which:
the amino acid at position 420 is Met, and the amino acid at position 397 is Gly, Ala, Ser, Thr, Cys, Val, Ile, Met, Pro, Phe, Tyr, Trp, His, Lys, Arg, Asn, Asp, Glu, or Gln.

In another preferred embodiment, the mut-PPO comprises a sequence of SEQ ID NO: 2 or SEQ ID NO:4, a variant, derivative, orthologue, paralogue or homologue thereof, in which:
the amino acid at position 420 is Val, and the amino acid at position 397 is Gly, Ala, Ser, Thr, Cys, Val, Ile, Met, Pro, Phe, Tyr, Trp, His, Lys, Arg, Asn, Asp, Glu, or Gln.

In another preferred embodiment, the mut-PPO comprises a sequence of SEQ ID NO: 2 or SEQ ID NO:4, a variant, derivative, orthologue, paralogue or homologue thereof, in which:
the amino acid at position 397 is Asn, Asp, Glu, or Gln, and the amino acid at position 400 is Ala, Ile, Val, or Met.

In another preferred embodiment, the mut-PPO comprises a sequence of SEQ ID NO: 2 or SEQ ID NO:4, a variant, derivative, orthologue, paralogue or homologue thereof, in which:
the amino acid at position 397 is Asn, Asp, Glu, or Gln, and the amino acid at position 457 is Met, Ala, Leu, Ile, or Val.

In another preferred embodiment, the mut-PPO comprises a sequence of SEQ ID NO: 2 or SEQ ID NO:4, a variant, derivative, orthologue, paralogue or homologue thereof, in which:
the amino acid at position 204 is Ala, Leu, Ile, or Val, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 400 is Ala, Ile, Val, or Met, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, and the amino acid at position 208 is Ser.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 400 is Ala, Ile, Val, or Met, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, the amino acid at position 397 is Asn, Asp, Glu, or Gln, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which:

the amino acid at position 204 is Ala, Leu, Ile, or Val, the amino acid at position 397 is Asn, Asp, Glu, or Gln, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, the amino acid at position 400 is Ala, Ile, Val, or Met, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 400 is Ala, Ile, Val, or Met, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, the amino acid at position 397 is Asn, Asp, Glu, or Gln, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 397 is Asn, Asp, Glu, or Gln, the amino acid at position 400 is Ala, Ile, Val, or Met, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 397 is Asn, Asp, Glu, or Gln, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 397 is Asn, Asp, Glu, or Gln, the amino acid at position 400 is Ala, Ile, Val, or Met, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 397 is Asn, Asp, Glu, or Gln, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 397 is Asn, Asp, Glu, or Gln, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 400 is Ala, Ile, Val, or Met, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 397 is Asn, Asp, Glu, or Gln, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 204 is Ala, Leu, Ile, or Val, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 208 is Ser, the amino acid at position 400 is Ala, Ile, Val, or Met, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:

the amino acid at position 400 is Ala, Ile, Val, or Met, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 400 is Ala, Ile, Val, or Met, and the amino acid at position 420 is Val, Met, Ala, Ile, or Leu.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, the amino acid at position 400 is Ala, Ile, Val, or Met, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 204 is Ala, Leu, Ile, or Val, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 400 is Ala, Ile, Val, or Met, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, the amino acid at position 397 is Asn, Asp, Glu, or Gln, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which:
the amino acid at position 204 is Ala, Leu, Ile, or Val, the amino acid at position 208 is Ser, the amino acid at position 400 is Ala, Ile, Val, or Met, the amino acid at position 420 is Val, Met, Ala, Ile, or Leu, and the amino acid at position 457 is Met, Ala, Leu, Ile, or Val.

In another preferred embodiment, the mut-PPO comprises a sequence of SEQ ID NO: 2 or SEQ ID NO:4 a variant, derivative, orthologue, paralogue or homologue thereof, in which:
the amino acid at position 128 is Leu, Ala, Val, or Ile, the amino acid at position 204 is Ala, Leu, Ile, or Val, the amino acid at position 400 is Ala, Ile, Val, or Met, the amino acid at position 420 is Val, Met, Ala, Ile, or Leu, and the amino acid at position 457 is Met, Ala, Leu, Ile, or Val.

It will be within the knowledge of the skilled artisan to identify conserved regions and motifs shared between the homologues, orthologues and paralogues encoded by SEQ ID NO: 1, 3, 5, 7, 9, 11, 13, 15, 17, 19, 21, 23, 25, 27, 29, 31, 33, 35, 37, 39, 41, 43, or 45, such as those depicted in Table 1. Having identified such conserved regions that may represent suitable binding motifs, amino acids corresponding to the amino acids listed in Table 3a and 3b, can be chosen to be substituted by any other amino acid, preferably by conserved amino acids as shown in table 2, and more preferably by the amino acids of tables 3a and 3b.

In addition, the present invention refers to a method for identifying a benzoxazinone-derivative herbicide by using a mut-PPO encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof.

Said method comprises the steps of:
a) generating a transgenic cell or plant comprising a nucleic acid encoding a mut-PPO, wherein the mut-PPO is expressed;
b) applying a benzoxazinone-derivative herbicide to the transgenic cell or plant of a) and to a control cell or plant of the same variety;
c) determining the growth or the viability of the transgenic cell or plant and the control cell or plant after application of said benzoxazinone-derivative herbicide, and
d) selecting "benzoxazinone-derivative herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mut-PPO which is resistant or tolerant to a benzoxazinone-derivative herbicide, the method comprising:
a) generating a library of mut-PPO-encoding nucleic acids,
b) screening a population of the resulting mut-PPO-encoding nucleic acids by expressing each of said nucleic acids in a cell or plant and treating said cell or plant with a benzoxazinone-derivative herbicide,
c) comparing the benzoxazinone-derivative herbicide-tolerance levels provided by said population of mut-PPO encoding nucleic acids with the benzoxazinone-derivative herbicide-tolerance level provided by a control PPO-encoding nucleic acid,
d) selecting at least one mut-PPO-encoding nucleic acid that provides a significantly increased level of tolerance to a benzoxazinone-derivative herbicide as compared to that provided by the control PPO-encoding nucleic acid.

In a preferred embodiment, the mut-PPO-encoding nucleic acid selected in step d) provides at least 2-fold as much resistance or tolerance of a cell or plant to a benzoxazinone-derivative herbicide as compared to that provided by the control PPO-encoding nucleic acid.

In a further preferred embodiment, the mut-PPO-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a benzoxazinone-derivative herbicide as compared to that provided by the control PPO-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wild-type or mut-PPO which is resistant or tolerant to a benzoxazinone-derivative herbicide, the method comprising:
a) identifying an effective amount of a benzoxazinone-derivative herbicide in a culture of plant cells or green algae that leads to death of said cells.
b) treating said plant cells or green algae with a mutagenizing agent,
c) contacting said mutagenized cells population with an effective amount of benzoxazinone-derivative herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mut-PPO from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mut-PPO-encoding sequences.

Nucleic acids comprising candidate and control PPO encoding sequences can be expressed in yeast, in a bacterial host strain, in an alga or in a higher plant such as tobacco or *Arabidopsis* and the relative levels of inherent tolerance of the PPO encoding sequences screened according to a visible indicator phenotype of the transformed strain or plant in the presence of different concentrations of the selected benzoxazinone-derivative herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed PPO. For example, in a relatively rapid assay system based upon transformation of a bacterium such as *E. coli*, each mut-PPO encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different PPO sequences. Such strains expressing nucleic acids comprising alternative candidate PPO sequences may be plated out on different concentrations of the selected benzoxazinone-derivative herbicide in, optionally, a tyrosine supplemented medium and the relative levels of inherent tolerance of the expressed PPO enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected benzoxazinone-derivative herbicides. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control PPO. Alternatively, an untransformed dicot plant such as *Arabidopsis* or Tobacco can be used as a control since this, in any case, expresses its own endogenous PPO. The average, and distribution, of herbicide tolerance levels of a range of primary plant transformation events or their progeny to benzoxazinone-derivative described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed PPO. Herbicides can suitably be applied pre-emergence or post-emergence.

Another object refers to an isolated nucleic acid encoding a mut-PPO, wherein the nucleic acid is identifiable by a method as defined above.

In another embodiment, the invention refers to a plant cell transformed by a wild-type or a mut-PPO nucleic acid or a plant cell which has been mutated to obtain a plant expressing a wild-type or a mut-PPO nucleic acid, wherein expression of the nucleic acid in the plant cell results in increased resistance or tolerance to a benzoxazinone-derivative herbicide as compared to a wild type variety of the plant cell.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the benzoxazinone-derivative herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327:70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the *agrobacteria* to act on plant seeds or to inoculate the plant meristem with *agrobacteria*. It has proved particularly expedient in accordance with the invention to allow a suspension of transformed *agrobacteria* to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mut-PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, or 46, or a variant or derivative thereof; c) a polynucleotide comprising at least 60 consecutive nucleotides of any of a) or b); and d) a polynucleotide complementary to the polynucleotide of any of a) through c).

Preferably, the expression of the nucleic acid in the plant results in the plant's increased resistance to benzoxazinone-derivative herbicide as compared to a wild type variety of the plant.

In another embodiment, the invention refers to a plant, preferably a transgenic plant, comprising a plant cell according to the present invention, wherein expression of the nucleic acid in the plant results in the plant's increased resistance to benzoxazinone-derivative herbicide as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mut-PPO nucleic acids, the nucleic acids can be derived from different genomes or from the same genome. Alternatively, in embodiments wherein the plant is non-transgenic and comprises multiple mut-PPO nucleic acids, the nucleic acids are located on different genomes or on the same genome.

In certain embodiments, the present invention involves herbidicide-resistant plants that are produced by mutation breeding. Such plants comprise a polynucleotide encoding a mut-PPO and are tolerant to one or more "benzoxazinone-derivative herbicides". Such methods can involve, for example, exposing the plants or seeds to a mutagen, particularly a chemical mutagen such as, for example, ethyl methanesulfonate (EMS) and selecting for plants that have enhanced tolerance to at least one or more benzoxazinone-derivative herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radio-isotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mut-PPO nucleic acid or over-expressed wild-type PPO nucleic acid, and has increased tolerance to a benzoxazinone-derivative herbicide as compared to a wild-type variety of the plant. It is possible for the plants of the present invention to have multiple wild-type or mut-PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mut-PPO alleles, wherein the plant has increased tolerance to a benzoxazinone-derivative herbicide as compared to a wild-type variety of the plant. The mut-PPO alleles can comprise a nucleotide sequence selected from the group consisting of a polynucleotide as defined in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof, a polynucleotide encoding a polypeptide as defined in SEQ ID NO: 2, 4, 6, 8, 10, 12, 14, 16, 18, 20, 22, 24, 26, 28, 30, 32, 34, 36, 38, 40, 42, 44, or 46, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

The herbicide-resistant plants of the invention that comprise polynucleotides encoding mut-PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mut-PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

It is to be understood that the plant of the present invention can comprise a wild type PPO nucleic acid in addition to a mut-PPO nucleic acid. It is contemplated that the benzoxazinone-derivative herbicide tolerant lines may contain a mutation in only one of multiple PPO isoenzymes. Therefore, the present invention includes a plant comprising one or more mut-PPO nucleic acids in addition to one or more wild type PPO nucleic acids.

In another embodiment, the invention refers to a seed produced by a transgenic plant comprising a plant cell of the present invention, wherein the seed is true breeding for an increased resistance to a benzoxazinone-derivative herbicide as compared to a wild type variety of the seed.

In another embodiment, the invention refers to a method of producing a transgenic plant cell with an increased resistance to a benzoxazinone-derivative herbicide as compared to a wild type variety of the plant cell comprising, transforming the plant cell with an expression cassette comprising a mut-PPO nucleic acid.

In another embodiment, the invention refers to a method of producing a transgenic plant comprising, (a) transforming a plant cell with an expression cassette comprising a mut-PPO nucleic acid, and (b) generating a plant with an increased resistance to benzoxazinone-derivative herbicide from the plant cell.

Consequently, mut-PPO nucleic acids of the invention are provided in expression cassettes for expression in the plant of interest. The cassette will include regulatory sequences operably linked to a mut-PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mut-PPO nucleic acid sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a mut-PPO nucleic acid sequence of the invention, and a transcriptional and translational termination region (i.e., termination region) functional in plants. The promoter may be native or analogous, or foreign or heterologous, to the plant host and/or to the mut-PPO nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mut-PPO nucleic acid sequence of the invention, it is intended that the promoter is not the native or naturally occurring promoter for the operably linked mut-PPO nucleic acid sequence of the invention. As used herein, a chimeric gene comprises a coding sequence operably linked to a transcription initiation region that is heterologous to the coding sequence.

While it may be preferable to express the mut-PPO nucleic acids of the invention using heterologous promoters, the native promoter sequences may be used. Such constructs would change expression levels of the mut-PPO protein in the plant or plant cell. Thus, the phenotype of the plant or plant cell is altered.

The termination region may be native with the transcriptional initiation region, may be native with the operably linked mut-PPO sequence of interest, may be native with the plant host, or may be derived from another source (i.e., foreign or heterologous to the promoter, the mut-PPO nucleic acid sequence of interest, the plant host, or any combination thereof). Convenient termination regions are available from the Ti-plasmid of A. tumefaciens, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize AdhI, intron1 gene (Callis et al. Genes and Development 1: 1183-1200, 1987), and leader sequences, (W— sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mut-PPO gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced mut-PPO expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka e/[alpha]/. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the mut-PPO nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the mut-PPO proteins of the invention include a native chloroplast transit peptide, any chloroplast transit peptide known in the art can be fused to the amino acid sequence of a mature mut-PPO protein of the invention by operably linking a choloroplast-targeting sequence to the 5'-end of a nucleotide sequence encoding a mature mut-PPO protein of the invention. Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the mut-PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, or 46, or a variant or derivative thereof; c) a polynucleotide comprising at least 60 consecutive nucleotides of any of a) or c); and d) a polynucleotide complementary to the polynucleotide of any of a) through c)

Preferably, the expression cassette further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl. Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl. Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a mut-PPO nucleic acid as described above, wherein expression of the vector in a host cell results in increased tolerance to a benzoxazinone-derivative herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mut-PPO polypeptides, fusion polypeptides, etc.).

In a preferred embodiment of the present invention, the mut-PPO polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A mut-PPO polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased tolerance to benzoxazinone-derivative herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mut-PPO polynucleotide into a plant is achieved by Agrobacterium mediated gene transfer. One transformation method known to those of skill in the art is the dipping of a flowering plant into an Agrobacteria solution, wherein the Agrobacteria contains the mut-PPO nucleic acid, followed by breeding of the transformed gametes. Agrobacterium mediated plant transformation can be performed using for example the GV3101(pMP90) (Koncz and Schell, 1986, Mol. Gen. Genet. 204:383-396) or LBA4404 (Clontech) Agrobacterium tumefaciens strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced mut-PPO polynucleotide may be maintained in the plant cell stably if it is incorporated into a non-chromosomal autonomous replicon or integrated into the plant chromosomes. Alternatively, the introduced mut-PPO polynucleotide may be present on an extra-chromosomal non-replicating vector and be transiently expressed or transiently active. In one embodiment, a homologous recombinant microorganism can be created wherein the mut-PPO polynucleotide is integrated into a chromosome, a vector is prepared which contains at least a portion of an PPO gene into which a deletion, addition, or substitution has been introduced to thereby alter, e.g., functionally disrupt, the endogenous PPO gene and to create a mut-PPO gene. To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene therapy American Scientist 87(3):240-247). Other homologous recombination procedures in Triticum species are also well known in the art and are contemplated for use herein.

In the homologous recombination vector, the mut-PPO gene can be flanked at its 5' and 3' ends by an additional nucleic acid molecule of the PPO gene to allow for homologous recombination to occur between the exogenous mut-PPO gene carried by the vector and an endogenous PPO gene, in a microorganism or plant. The additional flanking PPO nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the mut-PPO gene normally differs from the PPO gene at very few amino acids, a flanking sequence is not always necessary. The homologous recombination vector is introduced into a microorganism or plant cell (e.g., via polyethylene glycol mediated DNA), and cells in which the introduced mut-PPO gene has homologously recombined with the endogenous PPO gene are selected using art-known techniques.

In another embodiment, recombinant microorganisms can be produced that contain selected systems that allow for regulated expression of the introduced gene. For example, inclusion of a mut-PPO gene on a vector placing it under control of the lac operon permits expression of the mut-PPO gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mut-PPO polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mut-PPO polynucleotide. Accordingly, the invention further provides methods for producing mut-PPO polypeptides using the host cells of the invention. In one embodiment, the method comprises culturing the host cell of invention (into which a recombinant expression vector encoding a mut-PPO polypeptide has been introduced, or into which genome has been introduced a gene encoding a wild-type or mut-PPO polypeptide) in a suitable medium until mut-PPO polypeptide is produced. In another embodiment, the method further comprises isolating mut-PPO polypeptides from the medium or the host cell. Another aspect of the invention pertains to isolated mut-PPO polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mut-PPO polypeptide in which the polypeptide is separated from some of the cellular components of the cells in which it is naturally or recombinantly produced. In one embodiment, the language "substantially free of cellular material" includes preparations of a mut-PPO polypeptide having less than about 30% (by dry weight) of non-mut-PPO material (also referred to herein as a "contaminating polypeptide"), more preferably less than about 20% of non-mut-PPO material, still more preferably less than about 10% of non-mut-PPO material, and most preferably less than about 5% non-mut-PPO material.

When the mut-PPO polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mut-PPO polypeptide in which the polypeptide is separated from chemical precursors or other chemicals that are involved in the synthesis of the polypeptide. In one embodiment, the language "substantially free of chemical precursors or other chemicals" includes preparations of a mut-PPO polypeptide having less than about 30% (by dry weight) of chemical precursors or non-mut-PPO chemicals, more preferably less than about 20% chemical precursors or non-mut-PPO chemicals, still more preferably less than about 10% chemical precursors or non-mut-PPO chemicals, and most preferably less than about 5% chemical precursors or non-mut-PPO chemicals. In preferred embodiments, isolated polypeptides, or biologically active portions thereof, lack contaminating polypeptides from the same organism from which the mut-PPO polypeptide is derived. Typically, such polypeptides are produced by recombinant expression of, for example, a mut-PPO polypeptide in plants other than, or in microorganisms such as *C. glutamicum*, ciliates, algae, or fungi.

As described above, the present invention teaches compositions and methods for increasing the benzoxazinone-derivative tolerance of a crop plant or seed as compared to a wild-type variety of the plant or seed. In a preferred embodiment, the benzoxazinone-derivative tolerance of a crop plant or seed is increased such that the plant or seed can withstand a benzoxazinone-derivative herbicide application of preferably approximately 1-1000 g ai ha$^{-1}$, more preferably 20-160 g ai ha$^{-1}$, and most preferably 40-80 g ai ha$^{-1}$. As used herein, to "withstand" a benzoxazinone-derivative herbicide application means that the plant is either not killed or not injured by such application.

Furthermore, the present invention provides methods that involve the use of at least one benzoxazinone-derivative herbicide as described in detail supra.

In these methods, the benzoxazinone-derivative herbicide can be applied by any method known in the art including, but not limited to, seed treatment, soil treatment, and foliar treatment. Prior to application, the benzoxazinone-derivative herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to benzoxazinone-derivative herbicide, a wide variety of formulations can be employed for protecting plants from weeds, so as to enhance plant growth and reduce competition for nutrients. A benzoxazinone-derivative herbicide can be used by itself for pre-emergence, post-emergence, pre-planting, and at-planting control of weeds in areas surrounding the crop plants described herein, or a benzoxazinone-derivative herbicide formulation can be used that contains other additives. The benzoxazinone-derivative herbicide can also be used as a seed treatment. Additives found in a benzoxazinone-derivative herbicide formulation include other herbicides, detergents, adjuvants, spreading agents, sticking agents, stabilizing agents, or the like. The benzoxazinone-derivative herbicide formulation can be a wet or dry preparation and can include, but is not limited to, flowable powders, emulsifiable concentrates, and liquid concentrates. The benzoxazinone-derivative herbicide and herbicide formulations can be applied in accordance with conventional methods, for example, by spraying, irrigation, dusting, or the like.

Suitable formulations are describe in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Site-Directed Mutagenesis of *Amaranthus* PPO

Cloning of *Aramanthus* PPO

The *Amaranthus tuberculatus* coding sequence for PPO-susceptible and -resistant isoforms, and all mutant combinations and multiple mutations, (SEQ ID No: 1, 3, 5, 7) were synthesized and cloned by Geneart (Geneart A G, Regensburg, Germany).

Plasmids were isolated from *E. coli* TOP10 by performing a plasmid minpreparation and confirmed by DNA sequencing.

Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a *glycine* deletion in the α-8 helix of protoporphyrinogen oxidase. Biochimica et Biophysica Acta 1804 (2010), 1548-56)

Clones in pRSET vector were transformed into BL21 (DE3)-pLysS strain of *E. coli*. Cells were grown in 250 mL of LB with 100 μgmL-1 of carbenicillin, shaking overnight at 37° C. Cultures were diluted in 1 L of LB with antibiotic and grown at 37° C. shaking for 2 h, induced with 1 mM IPTG and grown at 25° C. shaking for 5 more hours. The cells were harvested by centrifugation at 1600×g, washed with 0.09% NaCl, and stored at −80° C.

Cells were lysed using a French press at 140 MPa in 50 mM sodium phosphate pH 7.5, 1 M NaCl, 5 mM imidazole, 5% glycerol, and 1 μg mL-1 leupeptin. Following lysis, 0.5 U of benzonase (Novagen, EMD Chemicals, Inc., Gibbstown, N.J.) and PMSF (final concentration of 1 mM) were added. Cell debris was removed by centrifugation at 3000×g. His-tagged PPO proteins were purified on a nickel activated Hitrap Chelating HP column (GE Healthcare Bio-Sciences Corp., Piscataway, N.J.) equilibrated with 20 mM sodium phosphate pH 8.0, 50 mM NaCl, 5 mM imidazole, 5 mM MgCl2, 0.1 mM EDTA, and 17% glycerol.

PPO eluted with 250 mM imidazole. The active protein was desalted on a PD-10 column (GE Healthcare Bio-Sciences Corp., Piscataway, N.J.) equilibrated with a 20 mM sodium phosphate buffer, pH 7.5, 5 mM MgCl2, 1 mM EDTA and 17% glycerol. Each liter of culture provided approximately 10 mg of pure PPO, which was stored at −20° C. until being used in assays.

PPO Activity Assay

PPO Enzyme Assay (Non-Recombinant).

PPO protein (EC 1.3.3.4) was extracted from coleoptiles or shoots (150 g fresh weight) of dark-grown corn, black nightshade, morning glory, and velvetleaf seedlings as described previously (Grossmann et al. 2010). Before harvesting, the seedlings were allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials were homogenized in the cold with a Braun blender using a fresh-weight-to-volume ratio of 1:4. Homogenization buffer consisted of tris(hydroxymethyl) aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations were obtained after centrifugation at 10 000×g for 5 min and resuspension in homogenization buffer before centrifugation at 150×g for 2 min to remove crude cell debris. The supernatant was centrifuged at 4000×g for 15 min and the pellet fraction was resuspended in 1 ml of a buffer containing Tris-HCl (50 mM; pH 7.3), EDTA (2 mM), leupeptin (2 μM), pepstatin (2 μM) and glycerol (200 ml $L^{-1}$) and stored at −80° C. until use. Protein was determined in the enzyme extract with bovine serum albumin as a standard. PPO activity was assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 μM), and 40 μg extracted protein in a total volume of 200 μl. The reaction was initiated by addition of substrate protoporphyrinogen IX at 22° C. saflufenacil, benzoxazinone-derivative herbicide, flumioxazin, butafenacil, acifluorfen, lactofen, bifenox, diuron, sulfentrazone were prepared in dimethyl sulfoxide (DMSO) solution (0.1 mM concentration of DMSO in the assay) and added to the assay mixture in concentrations of 0.005 μM to 5 μM before incubation. Fluorescence was monitored directly from the assay mixture using a POLARstar Optima/Galaxy (BMG) with excitation at 405 nm and emission monitored at 630 nm. Non-enzymatic activity in the presence of heat-inactivated extract was negligible. Inhibition of enzyme activity induced by the herbicide was expressed as percentage inhibition relative to untreated controls. Molar concentrations of compound required for 50% enzyme inhibition ($IC_{50}$ values) were calculated by fitting the values to the dose-response equation using non-linear regression analysis.

PPO Enzyme Assay (Recombinant)

Proto was purchased from Sigma-Aldrich (Milwaukee, Wis.). Protogen was prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays were conducted in 100 mM sodium phosphate pH 7.4 with 0.1 mM EDTA, 0.1% Tween 20, 5 μM FAD, and 500 mM imidazole. Dose-response curves with the PPO inhibitors saflufenacil, benzoxazinone-derivative herbicide, flumioxazin, butafenacil, acifluorfen, lactofen, bifenox, diuron, sulfentrazone, and MC-15608 were obtained in the presence of 150 µM Protogen. The excitation and emission bandwidths were set at 1.5 and 30 nm, respectively. All assays were made in duplicates or triplicates and measured using a POLARstar Optima/Galaxy (BMG) with excitation at 405 nm and emission monitored at 630 nm. Molar concentrations of compound required for 50% enzyme inhibition ($IC_{50}$ values) were calculated by fitting the values to the dose-response equation using non-linear regression analysis.

Example 2. Engineering PPO-Derivative Herbicide Tolerant Plants Having Wildtype or Mutated PPO Sequences PPO-derivative herbicide tolerant soybean (*Glycine max*) or corn (*Zea mays*) plants are produced by a method as described by Olhoft et al. (US patent 2009/0049567). For transformation of soybean or *Arabidopsis thaliana*, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with *Agrobacteria*, the explants are transferred to shoot introduction media without selection for one week. The explants were subsequently transferred to a shoot induction medium with 1-3 µM imazapyr (Arsenal) for 3 weeks to select for transformed cells. Explants with healthy callus/shoot pads at the primary node are then transferred to shoot elongation medium containing 1-3 µM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via *Agrobacterium*-mediated transformation.

Transformed cells were selected in selection media supplemented with 0.5-1.5 µM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with wildtype or mutated PPO sequences by floral dip method as described by McElver and Singh (WO 2008/124495). Transgenic *Arabidopsis* plants were subjected to TaqMan analysis for analysis of the number of integration loci. Transformation of *Oryza sativa* (rice) are done by protoplast transformation as described by Peng et al. (U.S. Pat. No. 6,653,529) T0 or T1 transgenic plant of soybean, corn, and rice containing mutated PPO sequences are tested for improved tolerance to PPO-derived herbicides in greenhouse studies and mini-plot studies with the following PPO-inhibiting herbicides: saflufenacil, benzoxazinone-derivative herbicide, flumioxazin, butafenacil, acifluorfen, lactofen, bifenox, diuron, sulfentrazone.

Transgenic *Arabidopsis thaliana* plants were assayed for improved tolerance to saflufenacil, benzoxazine-derivative herbicide, flumioxazin, butafenacil, acifluorfen, lactofen, bifenox, diuron, sulfentrazon in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*$m^{-2}$*$s^{-1}$ with 14:10 h light:dark photoperiod. Growth inhibition is evaluated seven to ten days after seeding in comparison to wild type plants. Additionally, transgenic T1 *Arabidopsis* plants were tested for improved tolerance to PPO-inhibiting herbicides in greenhouse studies with the following PPO-inhibiting herbicides: saflufenacil, benzoxazinone.derivative herbicide, flumioxazin, butafenacil, acifluorfen, lactofen, bifenox, diuron, sulfentrazone.

Example 3. Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, (saflufenacil, benzoxazinone-derivative herbicide, flumioxazin, butafenacil, acifluorfen, lactofen, bifenox, diuron, sulfentrazone). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli were initiated from 4 different maize or rice cultivars encompassing *Zea mays* and Japonica (Taipei 309, Nipponbare, Koshihikari) and Indica (Indica 1) varieties, respectively. Seeds were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 4.

TABLE 4

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 μg/L | |
| 2,4-D | Sigma | 2.0 mg/L | | | | | 1.0 mg/L |
| MgCl$_2$•6H$_2$O | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 4. Selection of Herbicide-Tolerant Calli

Once tissue culture conditions were determined, further establishment of selection conditions were established through the analysis of tissue survival in kill curves with saflufenacil, benzoxazinone-derivative herbicide, flumioxazin, butafenacil, acifluorfen, lactofen, bifenox, diuron, sulfentrazone. Careful consideration of accumulation of the herbicide in the tissue, as well as its persistence and stability in the cells and the culture media was performed. Through these experiments, a sub-lethal dose has been established for the initial selection of mutated material.

After the establishment of the starting dose of saflufenacil, benzoxazinone-derivative herbicide, flumioxazin, butafenacil, acifluorfen, lactofen, bifenox, diuron, sulfentrazone in selection media, the tissues were selected in a step-wise fashion by increasing the concentration of the PPO inhibitor with each transfer until cells are recovered that grew vigorously in the presence of toxic doses. The resulting calli were further subcultured every 3-4 weeks to R001M with selective agent. Over 26,000 calli were subjected to selection for 4-5 subcultures until the selective pressure was above toxic levels as determined by kill curves and observations of continued culture.

Alternatively, liquid cultures initiated from calli in MS711R with slow shaking and weekly subcultures. Once liquid cultures were established, selection agent was added directly to the flask at each subculture. Following 2-4 rounds of liquid selection, cultures were transferred to filters on solid R001M media for further growth.

Example 5. Regeneration of Plants

Tolerant tissue was regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways were also sequenced to characterize mutations. Finally, enzymes that change the fate (e.g. metabolism, translocation, transportaion) were also sequence to characterized mutations.

Following herbicide selection, calli were regenerated using a media regime of R025M for 10-14 days, R026M for ca. 2 weeks, R327M until well formed shoots were developed, and R008S until shoots were well rooted for transfer to the greenhouse. Regeneration was carried out in the light. No selection agent was included during regeneration.

Once strong roots were established, M0 regenerants were transplant to the greenhouse in square or round pots. Transplants were maintained under a clear plastic cup until they were adapted to greenhouse conditions. The greenhouse was set to a day/night cycle of 27° C./21° C. (80° F./70° F.) with 600 W high pressure sodium lights supplementing light to maintain a 14 hour day length. Plants were watered according to need, depending in the weather and fertilized daily.

Example 6. Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer.

PCR amplification was performed using Hotstar Taq DNA Polymerase (Qiagen) using touchdown thermocycling program as follows: 96° C. for 15 min, followed by 35 cycles (96° C., 30 sec; 58° C.–0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

Example 7. Demonstration of Herbicide-Tolerance

Selected mutants and escapes were transferred to small pots. Wild-type cultivars were germinated from seed to serve as controls.

After ca. 3 weeks post-transplant, M0 regenerants were sprayed using a track sprayer with saflufenacil, benzoxazinone-derivative herbicide, flumioxazin, butafenacil, acifluorfen, lactofen, bifenox, diuron, sulfentrazone supplemented with 0.1% methylated seed oil. After the plants had adapted to greenhouse conditions, a subset were sprayed with additional saflufenacil or benzoxazinone-derivative herbicide. Once sprayed, plants were kept on drought conditions for 24 hours before being watered and fertilized again. Sprayed plants were photographed and rated for herbicide injury at 1 and 3 weeks after treatment. No injury was observed on plants containing the heterozygous mutation while control plants and tissue culture escapes (regenerated plants negative for the sequenced mutations) were heavily damaged after treatment.

Example 8. Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media.

Mutant lines were selected using saflufenacil, benzoxazinone-derivative herbicide, flumioxazin, butafenacil, acifluorfen, lactofen, bifenox, diuron, sulfentrazone. Efficiencies of obtaining mutants was high either based on a percentage of calli that gave rise to a regenerable, mutant line or the number of lines as determined by the gram of tissue utilized.

Example 9 Screening of Mutagenized Algae Cells to Identify Herbicide Tolerant Clones and Identification of Causative Mutations in PPO Genes To generate mutations in PPO genes conferring "PPO-inhibiting herbicides" resistance, screening with chemical or UV mutagenized cell populations can be used. Especially unicellular organisms like *Chlamydomonas reinhardtii* are useful for identifying dominant mutations conferring herbicide resistance (Kataoka M, et al.; 1990; J. of Pest. Sci. 15: 449-451; Oshio H, et al.; 1993; Zeitschrift für Naturforschung 48: 339-344).

Algae cells of *Chlamydomonas reinhardtii* strains CC-503 and CC-1691 (Duke University, Durham, USA) were propagated in TAP medium (Gorman and Levine; 1965; PNAS 54: 1665-1669) by constant shaking at 100 rpm, 22° C. and 30 µmol Phot*$m^{-2}$*$s^{-2}$ light illumination. Compound screening was performed at 450 µmol Phot*$m^{-2}$*$s^{-2}$ illumination.

Sensitive strains of *Chlamydomonas reinhardtii* were mutagenized with 0.14 M ethylmethanesulfonate (EMS) for 1 h as described by Loppes (1969, Mol Gen Genet. 104: 172-177). Tolerant strains are identified by screening of mutagenized cells on solid TAP medium plates containing "PPO-inhibiting herbicide" like saflufenacil or benzoxazinone-derivative herbicide at wildype-lethal concentrations depending on compound activity in CC-503 or CC-1691 strain. Standard techniques were used for isolation of RNA and cDNA synthesis as described by Sambrock et al. (Molecular cloning (2001) Cold Spring Harbor Laboratory Press). Amplification of PPO genes from wild-type and resistant *Chlamydomonas reinhardii* from genomic DNA or copy DNA as template were performed by standard PCR techniques with DNA oligonucleotides as listed in Table 5. The resulting DNA molecules were cloned in standard sequencing vector (pJET1) and sequenced by standard sequencing techniques. Mutations were identified by comparing wildtype and mutant PPO sequences by sequence alignment tool Align X (Vector NTI Advance Software Version 10.3, Invitrogen, Carlsbad, Calif., USA).

TABLE 5

| PCR primer for amplification of CrPPO | |
|---|---|
| Primer name | Primer sequence (5'-3') |
| Cr_PPO1_Fw | ATGATGTTGACCCAGACTCCTGGGAC (SEQ ID NO: 47) |
| Cr_PPO1_Rv | TTAGGCCTTGACTGCGGCCTTGGAC (SEQ ID NO: 48) |

The invention claimed is:

1. A method for controlling undesired vegetation at a plant cultivation site, the method comprising the steps of:
   a) providing, at said site, a plant that comprises at least one nucleic acid comprising a nucleotide sequence encoding a herbicide-tolerant mutant protoporphyrinogen oxidase (PPO) enzyme comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine; and
   b) applying to said site an effective amount of a benzoxazinone-derivative herbicide.

2. The method of claim 1, wherein the plant comprises at least one additional heterologous nucleic acid comprising a nucleotide sequence encoding a herbicide tolerance enzyme.

3. An isolated nucleic acid encoding a herbicide-tolerant mutant PPO polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine.

4. A herbicide-tolerant mutant PPO enzyme comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine.

5. A transgenic plant cell transformed by the nucleic acid of claim 3.

6. A transgenic plant comprising the plant cell of claim 5, wherein expression of the nucleic acid in the plant results in the plant's increased tolerance to benzoxazinone-derivative herbicide as compared to a wild type plant.

7. A plant that expresses a mutagenized or recombinant herbicide-tolerant mutant PPO polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine.

8. A seed produced by a transgenic plant comprising the plant cell of claim 5, wherein the seed is true breeding for an increased tolerance to a benzoxazinone-derivative herbicide as compared to a wild type variety of the seed, and wherein the seed comprises said nucleic acid.

9. A method of producing a transgenic plant cell with an increased tolerance to a benzoxazinone-derivative herbicide as compared to a wild type variety of the plant cell comprising transforming the plant cell with an expression cassette comprising a nucleic acid encoding a herbicide-tolerant mutant PPO polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine.

10. A method of producing a transgenic plant comprising (a) transforming a plant cell with an expression cassette comprising a nucleic acid encoding a herbicide-tolerant mutant PPO polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine, and (b) generating a plant with an increased resistance to benzoxazinone-derivative herbicide from the plant cell.

11. The method of claim 9, wherein the expression cassette further comprises a transcription initiation regulatory region and a translation initiation regulatory region that are functional in the plant.

12. A method of identifying or selecting a transformed plant cell, plant tissue, plant or part thereof comprising: i) providing a transformed plant cell, plant tissue, plant or part thereof, wherein said transformed plant cell, plant tissue, plant or part thereof comprises a polynucleotide encoding a herbicide-tolerant mutant PPO enzyme that is used as a selection marker, wherein the herbicide-tolerant mutant PPO enzyme comprises an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, wherein the amino acid corresponding to position Phe420 of SEQ ID NO:2 is substituted with valine or methionine, and wherein said transformed plant cell, plant tissue, plant or part thereof may comprise a further isolated polynucleotide; ii) contacting the transformed plant cell, plant tissue, plant or part thereof with at least one benzoxazinine-derivative compound; iii) determining whether the plant cell, plant tissue, plant or part thereof is affected by the inhibiting compound; and iv) identifying or selecting the transformed plant cell, plant tissue, plant or part thereof.

13. The method of claim 1, wherein the amino acid corresponding to position Leu397 of SEQ ID NO:2 is substituted with aspartate and the amino acid corresponding to position Phe420 of SEQ ID NO:2 is substituted with valine.

14. The method of claim 1, wherein the amino acid corresponding to position Leu397 of SEQ ID NO:2 is substituted with glutamate and the amino acid corresponding to position Phe420 of SEQ ID NO:2 is substituted with methionine.

15. The method of claim 1, wherein the amino acid corresponding to position Leu397 of SEQ ID NO:2 is substituted with glutamine and the amino acid corresponding to position Phe420 of SEQ ID NO:2 is substituted with valine.

16. The method of claim 1, wherein the amino acid corresponding to position Leu397 of SEQ ID NO:2 is substituted with aspartate and the amino acid corresponding to position Phe420 of SEQ ID NO:2 is substituted with methionine.

17. The method of claim 1, wherein the amino acid corresponding to position Leu397 of SEQ ID NO:2 is substituted with glutamate and the amino acid corresponding to position Phe420 of SEQ ID NO:2 is substituted with valine.

18. The method of claim 1, wherein the amino acid corresponding to position Leu397 of SEQ ID NO:2 is substituted with glutamine and the amino acid corresponding to position Phe420 of SEQ ID NO:2 is substituted with methionine.

19. The method of claim 1, wherein the enzyme comprises the amino acid sequence of SEQ ID NO:2 with the following amino acid substitutions: Leu397Asp and Phe420Val.

20. The method of claim 1, wherein the enzyme comprises the amino acid sequence of SEQ ID NO:2 with the following amino acid substitutions: Leu397Asp and Phe420Met.

21. The method of claim 1, wherein the enzyme comprises the amino acid sequence of SEQ ID NO:2 with the following amino acid substitutions: Leu397Glu and Phe420Val.

22. The method of claim 1, wherein the enzyme comprises the amino acid sequence of SEQ ID NO:2 with the following amino acid substitutions: Leu397Glu and Phe420Met.

23. The method of claim 1, wherein the enzyme comprises the amino acid sequence of SEQ ID NO:2 with the following amino acid substitutions: Leu397Gln and Phe420Val.

24. The method of claim 1, wherein the enzyme comprises the amino acid sequence of SEQ ID NO:2 with the following amino acid substitutions: Leu397Glu and Phe420Met.

25. The nucleic acid of claim 3, wherein the amino acid corresponding to position Leu397 of SEQ ID NO:2 is substituted with aspartate and the amino acid corresponding to position Phe420 of SEQ ID NO:2 is substituted with valine.

26. The nucleic acid of claim 3, wherein the amino acid corresponding to position Leu397 of SEQ ID NO:2 is substituted with glutamate and the amino acid corresponding to position Phe420 of SEQ ID NO:2 is substituted with methionine.

27. The nucleic acid of claim 3, wherein the amino acid corresponding to position Leu397 of SEQ ID NO:2 is substituted with glutamine and the amino acid corresponding to position Phe420 of SEQ ID NO:2 is substituted with valine.

28. The nucleic acid of claim 3, wherein the amino acid corresponding to position Leu397 of SEQ ID NO:2 is substituted with aspartate and the amino acid corresponding to position Phe420 of SEQ ID NO:2 is substituted with methionine.

29. The nucleic acid of claim 3, wherein the amino acid corresponding to position Leu397 of SEQ ID NO:2 is substituted with glutamate and the amino acid corresponding to position Phe420 of SEQ ID NO:2 is substituted with valine.

30. The nucleic acid of claim 3, wherein the amino acid corresponding to position Leu397 of SEQ ID NO:2 is substituted with glutamine and the amino acid corresponding to position Phe420 of SEQ ID NO:2 is substituted with methionine.

31. The nucleic acid of claim 3, wherein the polypeptide comprises the amino acid sequence of SEQ ID NO:2 with the following amino acid substitutions: Leu397Asp and Phe420Val.

32. The nucleic acid of claim 3, wherein the polypeptide comprises the amino acid sequence of SEQ ID NO:2 with the following amino acid substitutions: Leu397Asp and Phe420Met.

33. The nucleic acid of claim 3, wherein the polypeptide comprises the amino acid sequence of SEQ ID NO:2 with the following amino acid substitutions: Leu397Glu and Phe420Val.

34. The nucleic acid of claim 3, wherein the polypeptide comprises the amino acid sequence of SEQ ID NO:2 with the following amino acid substitutions: Leu397Glu and Phe420Met.

35. The nucleic acid of claim 3, wherein the polypeptide comprises the amino acid sequence of SEQ ID NO:2 with the following amino acid substitutions: Leu397Gln and Phe420Val.

36. The nucleic acid of claim 3, wherein the polypeptide comprises the amino acid sequence of SEQ ID NO:2 with the following amino acid substitutions: Leu397Glu and Phe420Met.

37. The herbicide-tolerant mutant PPO enzyme of claim 4, wherein the amino acid corresponding to position Leu397 of SEQ ID NO:2 is substituted with aspartate and the amino acid corresponding to position Phe420 of SEQ ID NO:2 is substituted with valine.

38. The herbicide-tolerant mutant PPO enzyme of claim 4, wherein the amino acid corresponding to position Leu397 of SEQ ID NO:2 is substituted with glutamate and the amino acid corresponding to position Phe420 of SEQ ID NO:2 is substituted with methionine.

39. The herbicide-tolerant mutant PPO enzyme of claim 4, wherein the amino acid corresponding to position Leu397 of SEQ ID NO:2 is substituted with glutamine and the amino acid corresponding to position Phe420 of SEQ ID NO:2 is substituted with valine.

40. The herbicide-tolerant mutant PPO enzyme of claim 4, wherein the amino acid corresponding to position Leu397 of SEQ ID NO:2 is substituted with aspartate and the amino acid corresponding to position Phe420 of SEQ ID NO:2 is substituted with methionine.

41. The herbicide-tolerant mutant PPO enzyme of claim 4, wherein the amino acid corresponding to position Leu397 of SEQ ID NO:2 is substituted with glutamate and the amino acid corresponding to position Phe420 of SEQ ID NO:2 is substituted with valine.

42. The herbicide-tolerant mutant PPO enzyme of claim 4, wherein the amino acid corresponding to position Leu397 of SEQ ID NO:2 is substituted with glutamine and the amino acid corresponding to position Phe420 of SEQ ID NO:2 is substituted with methionine.

43. The herbicide-tolerant mutant PPO enzyme of claim 4, wherein the enzyme comprises the amino acid sequence of SEQ ID NO:2 with the following amino acid substitutions: Leu397Asp and Phe420Val.

44. The herbicide-tolerant mutant PPO enzyme of claim 4, wherein the enzyme comprises the amino acid sequence of SEQ ID NO:2 with the following amino acid substitutions: Leu397Asp and Phe420Met.

45. The herbicide-tolerant mutant PPO enzyme of claim 4, wherein the enzyme comprises the amino acid sequence of SEQ ID NO:2 with the following amino acid substitutions: Leu397Glu and Phe420Val.

46. The herbicide-tolerant mutant PPO enzyme of claim 4, wherein the enzyme comprises the amino acid sequence of SEQ ID NO:2 with the following amino acid substitutions: Leu397Glu and Phe420Met.

47. The herbicide-tolerant mutant PPO enzyme of claim 4, wherein the enzyme comprises the amino acid sequence of SEQ ID NO:2 with the following amino acid substitutions: Leu397Gln and Phe420Val.

48. The herbicide-tolerant mutant PPO enzyme of claim 4, wherein the enzyme comprises the amino acid sequence of SEQ ID NO:2 with the following amino acid substitutions: Leu397Glu and Phe420Met.

* * * * *